(12) United States Patent
Choi et al.

(10) Patent No.: US 11,524,047 B2
(45) Date of Patent: Dec. 13, 2022

(54) PHARMACEUTICAL COMPOSITIONS FOR PREVENTING OR TREATING PULMONARY METASTASIS OF CANCER INCLUDING CHI3L1 INHIBITOR AS ACTIVE INGREDIENT

(71) Applicant: Industry-University Cooperation Foundation Hanyang University, Seoul (KR)

(72) Inventors: Je-Min Choi, Seoul (KR); Do-Hyun Kim, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 232 days.

(21) Appl. No.: 16/957,249

(22) PCT Filed: Dec. 27, 2018

(86) PCT No.: PCT/KR2018/016776
§ 371 (c)(1),
(2) Date: Jun. 23, 2020

(87) PCT Pub. No.: WO2019/132547
PCT Pub. Date: Jul. 4, 2019

(65) Prior Publication Data
US 2021/0046151 A1   Feb. 18, 2021

(30) Foreign Application Priority Data

Dec. 28, 2017   (KR) .................. 10-2017-0182538

(51) Int. Cl.
| | | |
|---|---|---|
| *A61K 38/16* | (2006.01) | |
| *A61P 35/04* | (2006.01) | |
| *C12N 15/113* | (2010.01) | |
| *A61K 9/00* | (2006.01) | |
| *C12N 15/63* | (2006.01) | |
| *C12N 15/86* | (2006.01) | |
| *C12N 15/861* | (2006.01) | |
| *C12N 15/864* | (2006.01) | |

(52) U.S. Cl.
CPC .............. *A61K 38/16* (2013.01); *A61P 35/04* (2018.01); *C12N 15/1135* (2013.01); *C12N 15/1136* (2013.01); *C12N 15/63* (2013.01); *C12N 15/86* (2013.01); *C12N 15/861* (2013.01); *C12N 15/8645* (2013.01); *A61K 9/0043* (2013.01); *A61K 9/0073* (2013.01)

(58) Field of Classification Search
CPC .. A61P 35/04; C12N 15/1135; C12N 15/1136
See application file for complete search history.

(56) References Cited

U.S. PATENT DOCUMENTS

| 7,427,605 B2 * | 9/2008 | Davis ....................... A61K 9/14 536/24.5 |
| 2008/0311081 A1 * | 12/2008 | Fruehauf ................. A61P 37/08 435/320.1 |
| 2009/0175870 A1 | 7/2009 | Bonnichsen et al. |

FOREIGN PATENT DOCUMENTS

WO   2010/057009 A1   5/2010

OTHER PUBLICATIONS

Libreros et al (Frontiers Phys 4:392, 2013, 13 pages), (Year: 2013).*
Bitko et al (Methods Mol Biol. 2008;442:75-82) (Year: 2008).*
Lim et al. (Nat Commun (2015) 6, 8244) (Year: 2015).*
Loughran et al. (Eur. J. Nanomed. 2015; 7(2): 85-96) (Year: 2015).*
Bing MA, et al., "Role of Chitinase 3-like-1 and Semaphorin 7a in Pulmonary Melanoma Metastasis", Cancer Research, Feb. 1, 2015, pp. 487-496, vol. 75, No. 3.
Stephania Libreros, et al., "Induction of proinflammatory mediators by CHI3L1 is reduced by chitin treatment: decreased tumor metastasis in a breast cancer model", International Journal of Cancer, 2012, pp. 377-386, vol. 131.
Wanyi Tai, et al., "Functional peptides for siRNA delivery", Advanced Drug Delivery Reviews, 2017, pp. 157-168, vols. 110-111.
Do-Hyun Kim, et al., :"Regulation of chitinase-3-like-1 in T cell elicits Th1 and cytotoxic responses to inhibit lung metastasis", Nature Communications, Feb. 5, 2018, pp. 1-14, vol. 9, thesis No. 503.
International Search Report for PCT/KR2018/016776 dated Apr. 2, 2019 (PCT/ISA/210).
Sangho Lim, et al., "Cell Type Preference of a Novel Human Derived Cell-Permeable Peptide dNP2 and TAT in Murine Splenic Immune Cells"; PLOS One, published May 17, 2016, pp. 1-17.

* cited by examiner

*Primary Examiner* — Richard A Schnizer
(74) *Attorney, Agent, or Firm* — Sughrue Mion, PLLC

(57) ABSTRACT

The present invention relates to pharmaceutical compositions for preventing or treating pulmonary metastasis of cancer. More specifically, the present invention relates to compositions that enhance anti-cancer immunity of the lung rather than induce death of advanced cancer, thus being effective in inhibiting, preventing or treating pulmonary metastasis of cancer.

4 Claims, 63 Drawing Sheets
Specification includes a Sequence Listing.

WT-Th1 / WT-NA    KO-TH1 / KO-NA

PHARMACEUTICAL COMPOSITIONS FOR PREVENTING OR TREATING PULMONARY METASTASIS OF CANCER INCLUDING CHI3L1 INHIBITOR AS ACTIVE INGREDIENT

CROSS REFERENCE TO RELATED APPLICATIONS

This application is a National Stage of International Application No. PCT/KR2018/016776 filed Dec. 27, 2018, claiming priority based on Korean Patent Application No. 10-2017-0182538 filed Dec. 28, 2017.

TECHNICAL FIELD

The present invention relates to pharmaceutical compositions for preventing or treating pulmonary metastasis of cancer, and more specifically to compositions that enhance anti-cancer immunity of the lung rather than induce death of advanced cancer, thus being effective in inhibiting, preventing or treating pulmonary metastasis of cancer.

BACKGROUND ART

Cancer is a leading cause of death among modern people and still remains incurable despite continuous efforts over the past decades. Cancer is the most serious disease threatening to human health and is caused when a cell proliferates in an unlimited and uncontrolled way via a mutation process and becomes immortal. Carcinogenesis mechanisms and many therapeutic agents based on these mechanisms have been developed as a result of extensive research, but basic therapies for cancer have not been found yet.

The majority of cancer-related deaths has been attributed to cancer metastasis, particularly pulmonary metastatic recurrence. Metastasis refers to the spread of cancer cells within the primary organ or from the primary organ to another organ or its surrounding part. Usually, only malignant cancer cells have the ability to metastasize. Cancer cells escape from the primary cancer, migrate through the lymph or vascular system, circulate through the blood vessels, and grow in normal tissues of another part of the body. Cancer metastasis is a typical characterization of malignant cancer and accounts for 90% of all cancer-related deaths.

According to a report by the Korea Central Cancer Registry, Ministry of Health and Welfare, Korea, in December, 2014, the 5-year survival rate of breast cancer patients after treatment was 97% when the cancer lesion was localized to the primary site, 90% when it spread to the surrounding parts, and considerably reduced to 35% when it metastasized from the primary site to distant sites.

Some genes were found to regulate metastatic stages of cancer. However, since cancer metastasis is a very complicated process resulted from various genetic or epigenetic mutations, increased or decreased expression levels of specific genes do not lead to direct results in practical applications.

DETAILED DESCRIPTION OF THE INVENTION

Problems to be Solved by the Invention

The present invention has been made in view of the above-mentioned problems and intends to provide pharmaceutical compositions that can induce differentiation into Th1 cells to effectively inhibit pulmonary metastasis of cancer.

Means for Solving the Problems

One aspect of the present invention provides a pharmaceutical composition for preventing or treating pulmonary metastasis of cancer including, as an active ingredient, a Chi3l1 siRNA having the sequence set forth in SEQ ID NO: 1.

The Chi3l1 siRNA increases IFNγ-STAT1 signaling, induces differentiation into Th1 cells, and reduces the expression of the Twist1 gene.

The cancer is melanoma and the pharmaceutical composition inhibits pulmonary metastasis of melanoma.

A further aspect of the present invention provides a pharmaceutical composition for preventing or treating pulmonary metastasis of cancer including, as an active ingredient, a vector carrying a Chi3l1 siRNA having the sequence set forth in SEQ ID NO: 1, cells containing the vector or a culture medium of the cells.

The Chi3l1 siRNA increases IFNγ-STAT1 signaling, induces differentiation into Th1 cells, and reduces the expression of the Twist1 gene.

The cancer is melanoma and the pharmaceutical composition inhibits pulmonary metastasis of melanoma.

The vector may be selected from the group consisting of linear DNA, plasmid DNA, and recombinant viral vectors.

The recombinant virus may be selected from the group consisting of retroviruses, adenoviruses, adeno-associated viruses, herpes simplex viruses, and lentiviruses.

The cells may be selected from the group consisting of hematopoietic stem cells, dendritic cells, autologous tumor cells, and established tumor cells.

Another aspect of the present invention provides a pharmaceutical composition for preventing or treating pulmonary metastasis of cancer including, as an active ingredient, a complex of a cell-penetrating peptide having the sequence set forth in SEQ ID NO: 2 and a Chi3l1 siRNA having the sequence set forth in SEQ ID NO: 1.

The pharmaceutical composition may be administered to the lung via an intranasal route.

The pharmaceutical composition may be administered by inhalation of a spray or powder.

The pharmaceutical composition may have the ability to penetrate the nasal mucosa, the bronchial mucosa or pulmonary epithelial cells.

Yet another aspect of the present invention provides a method for preventing or treating pulmonary metastasis of cancer in a non-human animal, including administering of any of the pharmaceutical compositions described herein to the subject via an intranasal route.

Effects of the Invention

The pharmaceutical compositions and method of the present invention are effective in preventing or treating pulmonary metastasis of advanced cancer, recurrent cancer or cancer during treatment. That is, the pharmaceutical compositions and method of the present invention are based on a new immune function of Chi3l1 in lung cells to inhibit pulmonary metastasis of cancer and can be used to effectively treat cancer that has metastasized to the lung.

In addition, the pharmaceutical compositions of the present invention are much safer than conventional therapeutic agents for cancer because of their ability to improve the immune function of lung cells based on enhanced Th1 and CTL responses in lung cells rather than based on the induction of cancer apoptosis.

Furthermore, the pharmaceutical compositions of the present invention can be administered via an internasal route and enter the respiratory organ, which could not be achieved by conventional therapeutic agents for cancer. This internasal administration is advantageous in that the active ingredient penetrates and is delivered into lung cells. Therefore, the pharmaceutical compositions of the present invention are very effective in preventing and inhibiting pulmonary metastasis of cancer, achieving rapid, prompt, and efficient therapeutic or prophylactic effects.

BRIEF DESCRIPTION OF THE DRAWINGS

FIG. 5A shows the percentages of $CD4^+CD8^+$ cells, CD4+ cells, and CD8+ cells in the thymus, which were analyzed by flow cytometry, FIGS. 5B and 5C show the percentages of dendritic cells ($CD11c^+MHCII^+$) and macrophages ($CD11b^+$) in the spleen, which were analyzed by flow cytometry, FIGS. 5D to 5F show the results of flow cytometry for immune cells in the spleen, peripheral lymph node, and mesenteric lymph node, and FIG. 5G shows the Foxp3 expression in CD4 T cells, which was analyzed by flow cytometry. Data are mean±SD of at least five independent experiments.

FIG. 10A shows the differentiation patterns of WT and Chi3l1 KO naïve CD4 T cells into Th1, Th2, and Th17 under specific cytokine-skewing condition. Intracellular cytokine staining was performed to analyze lineage-specific cytokine expression. FIG. 10B shows the percentages of cytokines corresponding to subsets of the results of FIG. 10A. The top graph represents the results for Th1 cells, the middle graph represents the results for Th2 cells, and the bottom graph represents the results for Th17. Data are mean±SD of a total of three independent experiments. n.s., not significant; *p<0.05, **p<0.01. FIG. 10C shows the results of ELISA assay for IFNγ, TNFα, IL-4, and IL-17 production in the culture supernatants of FIG. 10A. Data are mean±SD of a total of three independent experiments. n.s., not significant; *p<0.05, **p<0.01. FIG. 10D shows the RNA expression levels of cytokines and transcription factors of differentiated T cells in FIG. 10A, which were analyzed by quantitative real-time PCR. Data are mean±SD of a total of three independent experiments. n.s., not significant; *p<0.05, **p<0.01. FIG. 10E shows the STAT phosphorylation of WT and Chi3l1 KO Th1 and Th2 cells measured by Western blotting (left) and the total STAT quantified by relative densitometric analysis of Western blotting (right). Data are mean±SD of a total of three independent experiments. n.s., not significant; *p<0.05, **p<0.01. FIG. 10F shows the IFNγ and IL-4 expression assessed by intracellular staining after WT and Chi3l1 KO naïve CD4 T cells were differentiated into Th1 cells with the indicated concentrations of IFNγ neutralizing antibodies and cells were harvested 3 days after the differentiation. FIG. 10G shows the percentages of IFNγ expression relative to IFNγ expression in WT Th1 cells without IFNγ neutralizing antibody. Data are mean±SD of a total of three independent experiments. n.s., not significant; *p<0.05, **p<0.01.

BEST MODE FOR CARRYING OUT THE INVENTION

Figure 1:
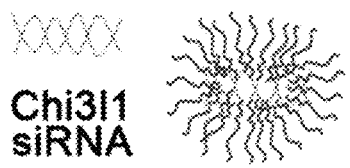
FIG. 1 shows the structures of siChi3l1 (left) and a dNP2-siChi3l1 complex (right) of the present invention.

Several aspects and various embodiments of the present invention will now be described in more detail.

One aspect of the present invention is directed to a pharmaceutical composition for preventing or treating pulmonary metastasis of cancer including, as an active ingredient, a Chi3l1 siRNA having the sequence set forth in SEQ ID NO: 1.

Chitinase is a defensive enzyme in plant to cleave chitin and protect hosts against pathogens. Chitinase-like proteins (CLPs) are found in mammals but they have protein signals binding to chitin but do not have the enzymatic activity to degrade chitin. Chitinase-like proteins in mammals have evolved into a role of regulating Th2 inflammation and immune responses.

Ym-1, also called chitinase 3-like 3 (Chi3l3), and Ym-2, also called chitinase 3-like 4 (Chi3l4), are CLPs that have been demonstrated to increase the number of γδT cells and IL-17 production in a nematode infection model. Ym-1 and Ym-2 are known to regulate Th2 inflammation in allergies.

BRP-39, also called chitinase 3-like 1 (Chi3l1), is known to have therapeutic effects on Streptococcus pneumoniae infections and type 2 infections but little is known about the detailed immunoregulatory function and therapeutic targetability of Chi3l1 in adaptive immune processes in mammals.

The present inventors have found through in vitro and in vivo experiments that Chi3l1 expression is increased in activated T cells (e.g., in Th2 cells). The present inventors have also found that Chi3l1-deficient T cells are hyper-responsive to TcR stimulation and are prone to differentiating into Th1 cells when IFNγ-STAT1 signaling increases. The present inventors have also found that Chi1l1-deficient Th1 cells show increased expression of anti-tumor immunity genes and decreased Th1-inhibiting genes such as Twist1, demonstrating that the Chi3l1 gene affects pulmonary metastasis of cancer.

The present inventors have also found that deletion of Chi3l1 in animal models shows reduced melanoma lung metastasis with increased IFNγ, T-bet, Granzyme B-producing CD4 and CD8 T cells in the lung.

However, direct administration of the Chi3l1 gene based on the above results has the problems that the Chi3l1 gene is not specific to tumor cells and side effects arise in normal cells. Thus, the present inventors have conducted numerous experiments to achieve excellent prophylactic or therapeutic effects of the Chi3l1 gene while avoiding the problems of the Chi3l1 gene, accomplishing the present invention.

The present inventors have found through various experiments that the siChi3l1 gene having the sequence set forth in SEQ ID NO: 1 can prevent or treat pulmonary metastasis of highly metastatic cancer cells.

The cancer may be any type of cancer and can be selected from the group consisting of: head and neck cancers, including brain tumor, spinal cord tumor, retinocytoma, oral cavity cancer, nasal cavity cancer, paranasal sinus cancer, pharynx cancer, laryngeal cancer, and neck cancer; skin cancers, including melanoma; endocrine cancers, including breast cancer, thyroid cancer, and malignant adrenal tumor; respiratory cancers, including lung cancer and pleural tumor; digestive cancers, including esophageal cancer, gastric cancer, malignant tumor of the small intestine, colorectal cancer, anal cancer, liver cancer, cholangiocarcinoma, and pancreatic cancer; urological cancers, including renal cancer, bladder cancer, prostate cancer, testis cancer, and penile cancer; gynecologic cancers, including cervical cancer, endometrial cancer, choriocarcinoma, and ovarian cancer; blood cancers, including acute and chronic leukemias, malignant lymphoma, and multiple myeloma; bone and soft tissue tumors; and childhood cancers, including pediatric leukemia and pediatric solid tumor. The cancer is preferably melanoma. The term "cancer metastasis" as used herein refers to metastasis of cancer developed at a specific site or recurrent cancer to a lung site.

The recurrent cancer refers to a cancer that recurs after general treatment.

The Chi3l1 siRNA having the sequence set forth in SEQ ID NO: 1 is a siRNA that specifically binds to the miRNA of the Chi3l1 gene to inhibit Chi3l1 expression. The Chi3l1 gene is a gene involved in pulmonary metastasis of cancer. Accordingly, inhibition of the Chi3l1 gene expression by the siRNA improves Th1 and CTL functions in the lung and enhances the immune function of the lung to inhibit tumor growth and progression rather than to induce tumor death. Thus, the Chi3l1 siRNA can be used to prevent or treat pulmonary metastasis of cancer developed at a specific site or recurrent cancer.

The Chi3l1 siRNA increases IFNγ-STAT1 signaling, induces differentiation into Th1 cells, and decreases Twist1 gene expression, achieving the desired effects of the present invention.

The siRNA is not especially limited to a particular sequence as long as it has the ability to inhibit the activity of Chi3l1. Preferably, the siRNA has the sequence set forth in SEQ ID NO: 1. The siRNA may further include dTdT at the 3'-end of the sequence. The sequence of the siChi3l1 targets mouse Chi3l1.

The term "siRNA (short interfering RNA)" as used herein refers to a double-stranded RNA that can cause RNAi inhibiting gene activity. The siRNA used in the present invention can inhibit the activity of Chi3l1. The siRNA may be of any type as long as it causes RNAi. For example, the siRNA may be synthesized chemically or biochemically. Alternatively, the siRNA may be synthesized in vivo. The siRNA may be a double-stranded RNA having at least 10 base pairs that is degraded in vivo from a double-stranded RNA having about >40 base pairs.

The siRNA may have a homology of at least about 70%, preferably at least 75%, more preferably at least 80%, even more preferably at least 85%, still even more preferably at least 90%, particularly preferably at least 95%, most preferably 100%, to a portion of the nucleic acid sequence of Chi3l1. The siRNA may be an RNA including a double-stranded region or its modification. The sequence region having a homology typically has a length of at least 15 nucleotides, preferably at least about 19 nucleotides, more preferably at least 20 nucleotides, even more preferably at least 21 nucleotides. Preferably, the sequence of the siRNA consists of bases capable of complementary binding to a region having the lowest homology to other RNAs in the sequence of Chi3l1.

The greatest advantage of the pharmaceutical composition is its ability to prevent or treat cancer metastasis without the need to use a vector or carrier despite direct administration of the siRNA.

A further aspect of the present invention is directed to a pharmaceutical composition for preventing or treating pulmonary metastasis of cancer including, as an active ingredient, a vector carrying a Chi3l1 siRNA having the sequence set forth in SEQ ID NO: 1, cells containing the vector or a culture medium of the cells.

The term "vector carrying the Chi3l1 siRNA" as used herein is intended to include vectors carrying polynucleotides capable of transcribing an shRNA that can be converted to an siRNA in cells.

The term "shRNA (short hairpin RNA)" as used herein refers to an RNA that includes a partially palindromic sequence in a single-stranded RNA to form a hairpin-like double-stranded structure in the 3'-region and that is cut by Dicer, a kind of RNase present in cells, after intracellular expression and converted to siRNAs. The length of the double-stranded structure is not particularly limited but is preferably at least 10 nucleotides, more preferably at least 20 nucleotides. The shRNA may be incorporated into in the vector. The shRNA-carrying vector is introduced into cells and the shRNA is expressed in the cells. The expressed shRNA is cut by Dicer, a kind of RNase III, and converted to siRNAs. The siRNAs may cause RNAi to inhibit the activity of Chi3l1.

The vector is not particularly limited and can be selected from the group consisting of linear DNA, plasmid DNA, and recombinant viral vectors. The recombinant virus can be selected from the group consisting of retroviruses, adenoviruses, adeno-associated viruses, herpes simplex viruses, and lentiviruses.

The cells can be selected from the group consisting of hematopoietic stem cells, dendritic cells, autologous tumor cells, and established tumor cells.

The pharmaceutical composition may further include one or more pharmaceutically acceptable carriers, in addition to the active ingredient. The pharmaceutical composition may be formulated for administration.

The pharmaceutical composition may be prepared into liquid solutions. In this case, the pharmaceutically acceptable carriers may be sterile biocompatible carriers and examples thereof include saline, sterilized water, Ringer's solution, buffered saline, albumin injectable solution, dextrose solution, maltodextrin solution, glycerol, and ethanol, which may be used alone or as a mixture of two or more thereof. If necessary, the pharmaceutical composition may further include other general additives, such as antioxidants, buffers, and bacteriostatic agents.

The pharmaceutical composition may further include one or more pharmaceutically suitable and physiologically acceptable adjuvants, in addition to the active ingredient. Examples of available adjuvants include excipients, disintegrants, sweeteners, binders, encapsulating agents, swelling agents, lubricants, glidants, and flavoring agents.

Diluents, dispersants, surfactants, binders, and lubricants may be further added to prepare the pharmaceutical composition into injectable formulations (for example, aqueous solutions, suspensions, and emulsions), pills, capsules, granules, and tablets. The pharmaceutical composition can be formulated according to the type of diseases or the kind of ingredients in accordance with any suitable method known in the art, preferably, any of the methods disclosed in Remington's Pharmaceutical Science, Mack Publishing Company, Easton Pa.

The pharmaceutical composition may be administered intravenously, intraarterially, intraperitoneally, intramuscularly, intrasternally, transdermally, intranasally, by nasal inhalation, topically, intrarectally, orally, intraocularly or intradermally. Most preferably, the pharmaceutical composition is administered via an intranasal route. When the pharmaceutical composition is administered intravenously, subcutaneously, intramuscularly, intraperitoneally or transdermally, its concentration should be increased by at least 2-fold to obtain the same effects. Thus, it is most preferred that the pharmaceutical composition is absorbed via an intranasal route in order to obtain maximum effects from the smallest possible amount.

The pharmaceutical composition of the present invention may further include a suitable carrier, excipient or diluent known in the art. The pharmaceutical composition may be prepared into any formulation that can be administered via an intranasal route. The formulation administered via an intranasal route is intended to include all formulations of the pharmaceutical composition that can be administered to the airway, respiratory tract, bronchoalveoli or lung through the nasal cavity by inhalation of a solution, powder, aerosol, spray or powder irrespective of the addition of a stabilizer or any other excipient.

Specifically, the intranasal administration can be accomplished using a pressurized sprayer with compressed air/oxygen mixture, an ultrasonic sprayer, an electric micropump sprayer, a metered dose inhaler (MDI) or a dry powder inhaler (DPI). An aerosol can be delivered by mechanical ventilation or through a tube inserted into the patient's bronchus.

Examples of carriers, excipients, and diluents that can be used in the pharmaceutical composition include lactose, dextrose, sucrose, sorbitol, mannitol, xylitol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated with diluents or excipients commonly used in the art, such as fillers, extenders, binders, wetting agents, disintegrating agents or surfactants.

The term "administration" as used herein refers to delivery of the pharmaceutical composition to a subject by any suitable method.

A preferred dose of the pharmaceutical composition depends on the condition and body weight of the patient, the severity of the disease, the form of the drug, and the route and time of administration but can be appropriately selected by one skilled in the art. For desired effects, the daily dose of the pharmaceutical composition is preferably from 0.01 ng/kg to 1000 mg/kg. The pharmaceutical composition may be administered in single or divided doses per day. The dose is in no way intended to limit the scope of the present invention.

Another aspect of the present invention is directed to a pharmaceutical composition for preventing or treating pulmonary metastasis of cancer including, as an active ingredient, a complex of a cell-penetrating peptide having the sequence set forth in SEQ ID NO: 2 and a Chi3l1 siRNA having the sequence set forth in SEQ ID NO: 1.

The present inventors have earnestly and intensively conducted research to achieve the desired prophylactic or therapeutic effects based on the above-described results for the Chi3l1 gene even when the pharmaceutical composition is used in a small amount, and as a result, have found that intranasal administration of the Chi3l1 siRNA complex (dNP2-siChi3l1) with the cell-penetrating peptide dNP2-HA2 increases Th1 and CTL responses to effectively inhibit pulmonary metastasis both in vitro and in vivo. In addition, the pharmaceutical composition enhances the effect of the siChi3l1-based complex on improving immunoregulatory function rather than on inducing the death of cancer cells and improves the immune function of lung cells based on increased Th1 and CTL responses in lung cells. Therefore, the pharmaceutical composition is considered much more stable and effective than conventional therapeutic agents for cancer based on the death of cancer cells.

Furthermore, the complex can penetrate cells because the siRNA selectively targets the Chi3l1 gene, as described above. Due to this ability, the complex can maximally exert its therapeutic effects to effectively inhibit and prevent cancer metastasis.

The dNP2-siChi3l1 complex can be administered via various routes, preferably an intranasal route. It was found that intranasal administration of the complex exhibits significantly (at least 2-3 times) better pharmacological effects on pulmonary metastasis of cancer than administration via other routes.

The complex is easier to prepare, simpler to construct, and more potentially stable than uncomplexed siChi3l1. Furthermore, the complex avoids the risk of uncontrolled cloning and the need to use a viral or non-viral vector, resulting in no danger of interference and potential side effects caused by transfection. Therefore, the complex can be considered very stable. Moreover, the complex can be synthesized in a very economical manner compared to carriers such as vectors and enables very efficient siChi3l1 delivery (can achieve maximum prophylactic or therapeutic effects by administration of siChi3l1 at a low concentration), thus being advantageous from the viewpoint of economic efficiency.

The complex has the greatest advantage that proper distribution of the drug does not depend on diffusion. Due to this advantage, the complex has cell permeability and the siChi3l1 is thus delivered and transmitted uniformly as a whole both inside and outside cells over the entire volume of the lung even when used in a small amount, achieving maximum prophylactic or therapeutic effects. In contrast, a conventional therapeutic agent is dispersed depending on a pressure gradient created between spaces outside lung cells after administration, with the result that the drug is non-uniformly distributed and its distribution depends on diffusion by a concentration gradient.

Local treatment of cancer cells is sufficient to kill the cancer cells, but local distribution of a drug is not effective in inhibiting and preventing pulmonary metastasis of cancer, unlike in the present invention. Accordingly, as in the present invention, uniform distribution and delivery of the complex over the entire lung clearly offers tremendous advantages in inhibiting and preventing cancer metastasis.

The ability of the complex to prevent or treat pulmonary metastasis of highly metastatic cancer was demonstrated through various experiments.

The cancer may be any type of cancer and can be selected from the group consisting of: head and neck cancers, including brain tumor, spinal cord tumor, retinocytoma, oral cavity cancer, nasal cavity cancer, paranasal sinus cancer, pharynx cancer, laryngeal cancer, and neck cancer; skin cancers, including melanoma; endocrine cancers, including breast cancer, thyroid cancer, and malignant adrenal tumor; respiratory cancers, including lung cancer and pleural tumor; digestive cancers, including esophageal cancer, gastric cancer, malignant tumor of the small intestine, colorectal cancer, anal cancer, liver cancer, cholangiocarcinoma, and pancreatic cancer; urological cancers, including renal cancer, bladder cancer, prostate cancer, testis cancer, and penile cancer; gynecologic cancers, including cervical cancer, endometrial cancer, choriocarcinoma, and ovarian cancer; blood cancers, including acute and chronic leukemias, malignant lymphoma, and multiple myeloma; bone and soft tissue tumors; and childhood cancers, including pediatric leukemia and pediatric solid tumor. The cancer is preferably melanoma. The term "cancer metastasis" as used herein refers to metastasis of cancer developed at a specific site or recurrent cancer to a lung site.

The recurrent cancer refers to a cancer that recurs after general treatment.

The term "complex" as used herein refers to a covalent complex that includes a cell-penetrating peptide having the sequence set forth in SEQ ID NO: 2 and a Chi3l1 siRNA having the sequence set forth in SEQ ID NO: 1, which are genetically fused or chemically conjugated to each other.

The "genetic fusion" refers to a linear covalent linkage formed through genetic expression of a DNA sequence encoding a protein.

If the dNP2-HA2 having the sequence set forth in SEQ ID NO: 2 is mixed with the siChi3l1 having the sequence set forth in SEQ ID NO: 1 in a ratio of 10:<1, the dNP2-siChi3l1 complex is not easily formed or is not effectively delivered into the lung even when administered via an intranasal route, with the result that the siChi3l1 fails to penetrate cells and target Chi3l1.

Thus, the dNP2-HA2 having the sequence set forth in SEQ ID NO: 2 is mixed with the siChi3l1 having the sequence set forth in SEQ ID NO: 1 in such amounts that the ratio of the number of nitrogen atoms (N) in the dNP-HA2 peptide to the number of phosphate groups (P) in the nucleic acid skeleton is 10-40:1, more preferably 22-28:1, most preferably 25:1.

It was found that intranasal administration significantly increases (by a factor of at least 2-3) the pharmacological effects of the dNP2-siChi3l1 complex on pulmonary metastasis of cancer than administration via other routes.

In the following experimental examples, the immunoregulatory effects of the dNP2-siChi3l1 complex were investigated after administration to pulmonary melanoma metastasis animal models induced by injection of melanoma cells. As a result, the administration of the dNP2-siChi3l1 complex was found to improve Th1 and CTL functions so that pulmonary metastasis of melanoma was significantly inhibited by 2- to 6-fold.

An at least 2-fold increase in the concentration of the pharmaceutical composition is necessary for administration of the dNP2-siChi311 complex via a route other than an intranasal route to achieve pharmacological effects on pulmonary metastasis of cancer.

The cancer may be any type of cancer and can be selected from the group consisting of: head and neck cancers, including brain tumor, spinal cord tumor, retinocytoma, oral cavity cancer, nasal cavity cancer, paranasal sinus cancer, pharynx cancer, laryngeal cancer, and neck cancer; skin cancers, including melanoma; endocrine cancers, including breast cancer, thyroid cancer, and malignant adrenal tumor; respiratory cancers, including lung cancer and pleural tumor; digestive cancers, including esophageal cancer, gastric cancer, malignant tumor of the small intestine, colorectal cancer, anal cancer, liver cancer, cholangiocarcinoma, and pancreatic cancer; urological cancers, including renal cancer, bladder cancer, prostate cancer, testis cancer, and penile cancer; gynecologic cancers, including cervical cancer, endometrial cancer, choriocarcinoma, and ovarian cancer; blood cancers, including acute and chronic leukemias, malignant lymphoma, and multiple myeloma; bone and soft tissue tumors; and childhood cancers, including pediatric leukemia and pediatric solid tumor. The cancer is preferably melanoma. The term "cancer metastasis" as used herein refers to metastasis of cancer developed at a specific site or recurrent cancer to a lung site.

The recurrent cancer refers to a cancer that recurs after general treatment.

The pharmaceutical composition may further include one or more pharmaceutically acceptable carriers, in addition to the active ingredient. The pharmaceutical composition may be formulated for administration.

The pharmaceutical composition may be prepared into liquid solutions. In this case, the pharmaceutically acceptable carriers may be sterile biocompatible carriers and examples thereof include saline, sterilized water, Ringer's solution, buffered saline, albumin injectable solution, dextrose solution, maltodextrin solution, glycerol, and ethanol, which may be used alone or as a mixture of two or more thereof. If necessary, the pharmaceutical composition may further include other general additives, such as antioxidants, buffers, and bacteriostatic agents.

The pharmaceutical composition may further include one or more pharmaceutically suitable and physiologically acceptable adjuvants, in addition to the active ingredient. Examples of available adjuvants include excipients, disintegrants, sweeteners, binders, encapsulating agents, swelling agents, lubricants, glidants, and flavoring agents.

Diluents, dispersants, surfactants, binders, and lubricants may be further added to prepare the pharmaceutical composition into injectable formulations (for example, aqueous solutions, suspensions, and emulsions), pills, capsules, granules, and tablets. The pharmaceutical composition can be formulated according to the type of diseases or the kind of ingredients in accordance with any suitable method known in the art, preferably, any of the methods disclosed in Remington's Pharmaceutical Science, Mack Publishing Company, Easton Pa.

The pharmaceutical composition may be administered intravenously, intraarterially, intraperitoneally, intramuscularly, intrasternally, transdermally, intranasally, by nasal inhalation, topically, intrarectally, orally, intraocularly or intradermally. Most preferably, the pharmaceutical composition is administered via an intranasal route. When the pharmaceutical composition is administered intravenously, subcutaneously, intramuscularly, intraperitoneally or transdermally, its concentration should be increased by at least 2-fold to obtain the same effects. Thus, it is most preferred that the pharmaceutical composition is absorbed via an intranasal route in order to obtain maximum effects from the smallest possible amount.

The pharmaceutical composition of the present invention may further include a suitable carrier, excipient or diluent known in the art. The pharmaceutical composition may be prepared into any formulation that can be administered via an intranasal route. The formulation administered via an intranasal route is intended to include all formulations of the pharmaceutical composition that can be administered to the airway, respiratory tract, bronchoalveoli or lung through the nasal cavity by inhalation of a solution, powder, aerosol, spray or powder irrespective of the addition of a stabilizer or any other excipient.

Specifically, the intranasal administration can be accomplished using a pressurized sprayer with compressed air/oxygen mixture, an ultrasonic sprayer, an electric micropump sprayer, a metered dose inhaler (MDI) or a dry powder inhaler (DPI). An aerosol can be delivered by mechanical ventilation or through a tube inserted into the patient's bronchus.

Examples of carriers, excipients, and diluents that can be used in the pharmaceutical composition include lactose, dextrose, sucrose, sorbitol, mannitol, xylitol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated with diluents or excipients commonly used in the art, such as fillers, extenders, binders, wetting agents, disintegrating agents or surfactants.

The term "administration" as used herein refers to delivery of the pharmaceutical composition to a subject by any suitable method.

A preferred dose of the pharmaceutical composition depends on the condition and body weight of the patient, the severity of the disease, the form of the drug, and the route and time of administration but can be appropriately selected by one skilled in the art. For desired effects, the daily dose of the pharmaceutical composition is preferably from 0.01 ng/kg to 1000 mg/kg. The pharmaceutical composition may be administered in single or divided doses per day. The dose is in no way intended to limit the scope of the present invention.

Yet another aspect of the present invention is directed to a method for preventing or treating pulmonary metastasis of cancer in a non-human animal, including administering of any of the pharmaceutical compositions described herein to the subject via an intranasal route.

The pharmaceutical compositions can be administered via an intranasal or intramucosal route or by inhalation. The mode of administration can also be sufficiently extended and applied to the delivery of culture cells as well as general in vivo delivery, that is, delivery of animal cells, animal tissues, and animal bodies.

The pharmaceutical compositions area nonimmunogenic and noninfectious and are not limited by the size of plasmids because DNA is not packaged in vector organisms such as retroviruses or adenoviruses. Therefore, the pharmaceutical compositions can be used in recombinant gene expression structures of any practical size.

Mode for Carrying Out the Invention

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

EXPERIMENTAL METHODS

1) Animal Models 6- to 8-week-old C57BL/6 J mice were used. Chi3l1 KO mice were provided by Jack A. Elias (Brown University). All mice were housed and maintained in a specific pathogen-free facility. All mice were bred in controlled conditions of temperature (21±1° C.), humidity (50±5%), and 12 h light/dark cycle with regular chow (PicoLab Rodent Diet) and periodically fed with food and autoclaved water.

All animal protocols were approved by the Animal Experimentation Ethics Committee at Hanyang University, Korea. Experiments were performed according to the guidelines of the Animal Experimentation Ethics Committee at Hanyang University, Korea.

2) In Vitro T Cell Activation and Differentiation.

WT and Chi3l1 KO naïve CD4 T cells were isolated using mouse $CD4^+CD25^-CD62L^+$ T Cell Isolation Kit II (Miltenyi Biotec) according to the manufacturer's protocols. Purity was around 95%. Fluorochrome-labeled $CD4^+CD25^-CD62L^{high}CD44^{low}$ naïve CD4 T cells and $CD8^+CD25^-CD44^-CD62L^{high}$ naïve CD8 T cells were sorted by FACS Aria cell sorter (BD Biosciences, Franklin Lakes, N.J.). Purity was around 98%. Purified naïve CD4 and CD8 T cells were activated by 2 μg/mL plate-bound anti-CD3 and anti-CD28 antibodies (BD Biosciences) and differentiated by exposure to the following cytokines for 3 or 5 days: media only for Th0; IL-2 (50 U/mL, Peprotech) for CTL; IL-12 (0.2 ng/mL, BD Biosciences), IL-2 (50 U/mL), and anti-IL-4 antibody (5 μg/mL, BD Biosciences) for Th1; IL-4 (30 ng/mL, BD Biosciences), IL-2 (50 U/mL), and anti-IFNγ antibody (5 μg/mL, BD Biosciences) for Th2; and TGF-β (0.5 ng/mL, R&D Systems), IL-6 (30 ng/mL, BD Biosciences), IL-23 (20 ng/mL, BD Biosciences), IL-1β (20 ng/mL, R&D Systems), anti-IFNγ (5 μg/mL), and anti-IL-4 (5 μg/mL) antibodies for Th17.

For measuring IL-4 expression in the Th2 subset, Th2 cells were harvested at day 5 and further reactivated by plate-bound anti-CD3 antibody for 24 h. In some experiments, the indicated concentration of rmChi3l1 protein or IFNγ-neutralizing antibody or the indicated amount of dNP2-siEGFP or dNP2-siChi3l1 was added to Th1- or CTL-skewing conditions. IL-2, IFNγ, IL-4, and IL-17 were measured in culture supernatants by ELISA (eBioscience).

3) Flow Cytometry

To measure cell proliferation, sorted WT and Chi3l1 KO naïve CD4 T cells were stained with CFSE (0.75 μM, Invitrogen) for 10 min at 37° C. and washed with complete RPMI media. CFSE-labeled cells were stimulated with plate-bound anti-CD3 and anti-CD28 antibodies for 3 days. Dividing cells were analyzed by flow cytometry, following staining with anti-mouse CD4-PerCP-Cy5.5 antibodies. To determine intracellular cytokine levels, cells were restimulated with eBioscience Cell Stimulation Cocktail (plus protein transport inhibitors) for 4 h and stained with anti-mouse CD4-PerCP-Cy5.5 or CD8-PerCP-Cy5.5 for 15 min. Cells were further fixed, permeabilized, and stained with anti-mouse IFNγ-FITC, IL-4-PE or TNFα-PE, and IL-17-APC for CD4 T cells or IFNγ-APC, TNFα-PE, Granzyme B-FITC for CD8 T cells. Cells were analyzed by flow cytometry.

For the pulmonary melanoma metastasis model, purified lymphocytes were restimulated with eBioscience Cell Stimulation Cocktail (plus protein transport inhibitors) for 4 h and stained with anti-mouse CD4-APC-Cy7, CD8-PerCP-Cy5.5, and NK1.1-PE for 30 min. Cells were fixed, permeabilized, and stained with anti-mouse IFNγ-APC, Granzyme B-FITC, T-bet-PE-cy7, and Foxp3-PE and analyzed by flow cytometry.

4) Western Blotting

Enriched naïve CD4 T cells were skewed to Th0, Th1, and Th2 helper T cells for 3 or 5 days and lysed with RIPA buffer (Cell Signaling Technology) in the presence of HALT inhibitor (Thermo Fisher Scientific) on ice for 30 min. Protein amounts in lysates were determined by BCA protein assay kit (Thermo Fisher Scientific). After SDS-PAGE, proteins were transferred onto PVDF membranes (Bio-Rad). Membranes were blocked with 5% skim milk in Tris-buffered saline containing 0.1% Tween-20. After blocking, membranes were incubated with primary antibody (listed below) for overnight at 4° C. Membranes were incubated with secondary antibody (listed below) for 1 h at room temperature. Washed membranes were analyzed with EZ-Western Lumi Pico or Femto reagent (DoGen). Band intensity was measured by Fusion-Solo, and gated band intensities from acquired images were analyzed by Fusion-capt advance (Vilber Lourmat). Mouse anti-Chi3l1 antibody was from R&D Systems, and mouse p-Erk, p-Akt, pSTAT1, pSTAT4, pSTAT6, tSTAT1, tSTAT4, and tSTAT6 antibodies and HRP-conjugated anti-rabbit were from Cell Signaling Technology.

5) Quantitative Real-Time PCR

Total RNA from in vitro differentiated CD4 T cells, CD8 T cells, and separated lung lymphocytes were isolated with RNeasy Mini kits (Qiagen). Lung tissue was disrupted by a homogenizer with TRIzol (Thermo Fisher Scientific), and total RNA was extracted. cDNA was synthesized with ReverTra Ace qPCR RT master mix (Toyobo). Real-time PCR was performed on a Bio-Rad CFX Connect Real-Time PCR detection system using iQ SYBR Green Supermix (Bio-Rad). Primer sequences used are listed in Table 1.

TABLE 1

|  | Forward 5' to 3' | Reverse 3' to 5' |
| --- | --- | --- |
| Actb | TGTCCCTGTATGCCTCTGGT (SEQ ID NO: 3) | CACGCACGATTTCCCTCTC (SEQ ID NO: 4) |
| Chi3l1 | GTACAAGCTGGTCTGCTACTTC (SEQ ID NO: 5) | ATGTGCTAAGCATGTTGTCGC (SEQ ID NO: 6) |

TABLE 1-continued

|  | Forward 5' to 3' | Reverse 3' to 5' |
|---|---|---|
| Tbx21 | AGCAAGGACGGCGAATGTT (SEQ ID NO: 7) | GGGTGGACATATAAGCGGTTC (SEQ ID NO: 8) |
| Runx3 | GACTCCTTCCCCAACTATACACC (SEQ ID NO: 9) | GTGCTCGGGTCTCGTATGAA (SEQ ID NO: 10) |
| Ifng | ATGAACGCTACACACTGCATC (SEQ ID NO: 11) | CCATCCTTTTGCCAGTTCCTC (SEQ ID NO: 12) |
| Gata3 | GAAGGCATCCAGACCCGAAAC (SEQ ID NO: 13) | ACCCATGGCGGTGACCATGC (SEQ ID NO: 14) |
| Il4 | GGTCTCAACCCCCAGCTAGT (SEQ ID NO: 15) | GCCGATGATCTCTCTCAAGTGAT (SEQ ID NO: 16) |
| Il13 | CAGCCTCCCCGATACCAAAAT (SEQ ID NO: 17) | GCGAAACAGTTGCTTTGTGTAG (SEQ ID NO: 18) |
| Il5 | CTCTGTTGACAAGCAATGAGACG (SEQ ID NO: 19) | TCTTCAGTATGTCTAGCCCCTG (SEQ ID NO: 20) |
| Il10 | GCTCTTACTGACTGGCATGAG (SEQ ID NO: 21) | CGCAGCTCTAGGAGCATGTG (SEQ ID NO: 22) |
| Junb | TCACGACGACTCTTACGCAG (SEQ ID NO: 23) | CCTTGAGACCCCGATAGGGA (SEQ ID NO: 24) |
| Rorgt | GACCCACACCTCACAAATTGA (SEQ ID NO: 25) | AGTAGGCCACATTACACTGCT (SEQ ID NO: 26) |
| Il17 | TTTAACTCCCTTGGCGCAAAA (SEQ ID NO: 27) | CTTTCCCTCCGCATTGACAC (SEQ ID NO: 28) |
| Il21 | GGACCCTTGTCTGTCTGGTAG (SEQ ID NO: 29) | TGTGGAGCTGATAGAAGTTCAGG (SEQ ID NO: 30) |
| Gmcsf | GGCCTTGGAAGCATGTAGAGG (SEQ ID NO: 31) | GGAGAACTCGTTAGAGACGACTT (SEQ ID NO: 32) |
| Batf | GTTCTGTTTCTCCAGGTCC (SEQ ID NO: 33) | GAAGAATCGCATCGCTGC (SEQ ID NO: 34) |
| Socs1 | CTGCGGCTTCTATTGGGGAC (SEQ ID NO: 35) | AAAAGGCAGTCGAAGGTCTCG (SEQ ID NO: 36) |
| Socs3 | ATGGTCACCCACAGCAAGTTT (SEQ ID NO: 37) | TCCAGTAGAATCCGCTCTCCT (SEQ ID NO: 38) |
| Socs5 | GAGGGAGGAAGCCGTAATGAG (SEQ ID NO: 39) | CGGCACAGTTTTGGTTCCG (SEQ ID NO: 40) |
| Perforin | GAGAAGACCTATCAGGACCA (SEQ ID NO: 41) | AGCCTGTGGTAAGCATG (SEQ ID NO: 42) |
| Gzmb | CCTCCTGCTACTGCTGAC (SEQ ID NO: 43) | GTCAGCACAAAGTCCTCTC (SEQ ID NO: 44) |
| Il13ra2 | ACCGAAATGTTGATAGCGACAG (SEQ ID NO: 45) | ACAATGCTCTGACAAATGCGTA (SEQ ID NO: 46) |
| Chit1 | TGGGCAGGTGTGATGACTCT (SEQ ID NO: 47) | CCCTGGGAAAGAACCGAACTG (SEQ ID NO: 48) |
| Amcase | CTGCGTCAGTATGGGTTTGAT (SEQ ID NO: 49) | TGGGCCTGTTGCTCTCAATAG (SEQ ID NO: 50) |
| Ym-1 | ACCTGCCCCGTTCAGTGCCAT (SEQ ID NO: 51) | CCTTGGAATGTCTTTCTCCACAG (SEQ ID NO: 52) |
| Foxp3 | CCCATCCCCAGGAGTCTTG (SEQ ID NO: 53) | ACCATGACTAGGGGCACTGTA (SEQ ID NO: 54) |
| Eomes | TCATCGCTGTGACGGCCTACCA (SEQ ID NO: 55) | GGGGAATCCGTGGGAGATGGAGT (SEQ ID NO: 56) |
| Tnfsf10 | ATGGTGATTTGCATAGTGCTCC (SEQ ID NO: 57) | GCAAGCAGGGTCTGTTCAAGA (SEQ ID NO: 58) |

TABLE 1-continued

| | Forward 5' to 3' | Reverse 3' to 5' |
|---|---|---|
| Ccr5 | TTTTCAAGGGTCAGTTCCGAC (SEQ ID NO: 59) | GGAAGACCATCATGTTACCCAC (SEQ ID NO: 60) |
| Cxcr3 | TACCTTGAGGTTAGTGAACGTCA (SEQ ID NO: 61) | CGCTCTCGTTTTCCCCATAATC (SEQ ID NO: 62) |
| Cxcr2 | ATGCCCTCTATTCTGCCAGAT (SEQ ID NO: 63) | GTGCTCCGGTTGTATAAGATGAC (SEQ ID NO: 64) |
| Ctse | GACATCAGTCCCTTCGGAAGA (SEQ ID NO: 65) | AGGGGTTCATTGACACTCGAATA (SEQ ID NO: 66) |
| Twist1 | GGACAAGCTGAGCAAGATTCA (SEQ ID NO: 67) | CGGAGAAGGCGTAGCTGAG (SEQ ID NO: 68) |

6) RNA Sequencing

Total RNA was isolated from WT and Chi3l1 KO naïve and Th1 cells using TRIzol reagent (Invitrogen). RNA quality was assessed by Agilent 2100 bioanalyzer using RNA 6000 Nano Chips (Agilent Technologies, Amstelveen, The Netherlands). RNA quantification was performed using an ND-2000 spectrophotometer (Thermo Fisher Scientific). For control and test RNAs, library construction was performed using SENSE mRNA-Seq Library Prep Kits (Lexogen, Inc., Austria) according to the manufacturer's instructions.

Briefly, 2 μg of total RNA was prepared and incubated with magnetic beads decorated with oligo-dT, then all other RNAs except mRNA were removed by washing. Library production is initiated by random hybridization of starter/stopper heterodimers to the poly(A) RNA still bound to the magnetic beads. These starter/stopper heterodimers contain Illumina-compatible linker sequences. A single-tube reverse transcription and ligation reaction extends the starter to the next hybridized heterodimer, where the newly-synthesized cDNA insert is ligated to the stopper. Second-strand synthesis is performed to release the library from the beads, and the library is then amplified. Barcodes were introduced when the library was amplified. High-throughput sequencing was performed as paired-end 100 sequencing using a HiSeq 2000 instrument (Illumina, Inc., USA). mRNA-Seq reads were mapped using the TopHat software tool to obtain an alignment file. Differentially expressed genes were determined based on counts from unique and multiple alignments using Edge R within R version 3.2.2 (R development Core Team, 2011) using BIOCONDUCTOR version 3.0 (Gentleman et al., 2004). The alignment file was used for assembling transcripts, estimating abundances, and detecting differential expression of genes or isoforms using cufflinks. FPKM (fragments per kilo base of exon per million fragments) method was used to determine expression levels of gene regions. A global normalization method was used for comparisons between samples. Gene classification was based on searches performed by DAVID (http://david-.abcc.ncifcrf.gov/).

7) Gel Retardation Assay

To determine optimal conditions for forming cell-permeable peptide-siRNA complexes, 1.5 μg of Chi3l1 siRNA (Bioneer) was mixed with dNP2-HA2 peptide (Genscript) at N/P ratios of 1:1, 1:10, and 1:25 (the ratios of the number of nitrogen atoms (N) in dNP2-HA2 peptide to the number of phosphate groups (P) in nucleic acid skeleton) and incubated for 30 min at room temperature in the dark. After incubation, complexes were mixed with DNA loading dye, and gel electrophoresis was performed on 2% agarose gel for 20 min 8) Pulmonary Melanoma Metastasis Model The mouse melanoma cell line (B16F10) established from C57BL6/J mouse melanoma was provided by HA Sang-Jun (Yonsei University). B16F10 cells were maintained in complete DMEM at 37° C. After culturing to 90% confluence in complete DMEM, cells were harvested, adjusted to $10^6$ cells/mL in pre-warmed PBS, and $5 \times 10^5$ cells were injected into mice via the tail vein.

At day 14 after cell injection, mice were sacrificed, and the numbers of melanoma colonies visualized as black dots on the lung surface were counted. For histological analysis, paraffin blocks of lung tissues were deparaffinized and stained by hematoxylin and eosin. Tumor sizes in lung tissue were measured by Image J software 1.48 v. Other lung lobes were mechanically chopped and incubated in $Ca^{2+}$- and $Mg^{2+}$-containing DPBS with collagenase D (1 mg/mL, Roche) for 30 min at 37° C. Enzymatic digestions were stopped with 0.5 M EDTA solution. Digested cells were filtered by 40-μm cell strainer, and RBCs were lysed with Ack buffer. Lung lymphocyte cells were enriched by Percoll gradients, and the cells were analyzed by flow cytometry and quantitative real-time PCR.

9) In Vitro Cytotoxicity Assay

B16F10 melanoma cells were seeded into 96-well plates in 100 μL media. Activated WT and Chi3l1 KO NK and CD8 T cells were added to wells containing B16F10 cells at different densities. After 8 h (for NK cells) or 24 h (CD8 T cells), the well plates were washed with PBS and media containing CCK-8 were added. Viable B16F10 melanoma cells were counted. The percent CTL cell activity was calculated in proportion to the OD value of positive control.

10) In Vitro siRNA Transfection

To express Chi3l1 in HEK293T/17 cells, cells were transfected with a cloned Chi3l1-overexpression vector using Lipofectamine 2000 (Invitrogen). In some experiments, EGFP or Chi3l1 siRNA was added. Transfection followed the manufacturer's protocol. dNP2-siChi3l1 was added independently, and media were replaced 6 h later. Transfected cells were incubated for 2 days, and media and cells were harvested. Chi3l1 levels in culture media were determined by ELISA (R&D), and Chi3l1 mRNA in transfected cells was quantified by real-time PCR.

11) In Vivo siRNA Transfection 2.5 μg of Chi3l1 siRNA (Bioneer) or EGFP siRNA (Bioneer) was incubated with 70 μg of dNP2-HA2 peptide for 30 min at room temperature in the dark. Peptide-siRNA complexes were intranasally administered to mice, which were sacrificed every 24 h for 3 days. Lung tissue was disrupted in T-PER Tissue Protein Extraction Reagent (Thermo Fisher Scientific) for protein lysates or in TRIzol for RNA extraction. Chi3l1 protein in the lung was measured by Chi3l1 ELISA kit (R&D Systems). In the WT lung metastasis model treated with dNP2-siRNA complex, B16F10 melanoma was injected into the pulmonary melanoma metastasis model, and then peptide-siRNA complex was intranasally administered to the model every other day. At 14 days after melanoma injection, mice were sacrificed and analyzed.

12) Statistical Analysis

All data were analyzed by two-tailed Student's t-test using Prism5 software (GraphPad). P-values less than 0.05 were considered statistically significant.

Unless otherwise mentioned, cells were designated in accordance with the general rules known in the art. For example, CD4+ indicates CD4 T cells, CD8+ indicates cytotoxic T cells, NK+CD4-CD8-indicates natural killer cells, and NK-CD4-CD8-indicates other immune cell populations.

PREPARATIVE EXAMPLE 1

Synthesis of dNP2-HA2 peptide and Chi3l1 siRNA

Chi3l1 siRNA having the sequence set forth in SEQ ID NO: 1 and dNP2-HA2 peptide having the amino acid sequence set forth in SEQ ID NO: 2 were synthesized.

```
                                         SEQ ID NO: 1
CAGGAGUUUAAUCUCUUGCAA

SEQ ID NO: 2
KIKKVKKKGRKGSKIKKVKKKGRKGLFGAIAGFIENGWEGMIDG
```

Hereinafter, the Chi3l1 siRNA and the dNP2-HA2 peptide are also referred to simply as "siChi3l1" and "dNP2", respectively. dNP2 is a cell-penetrating peptide. After design of the sequences, the synthesis of the Chi3l1 siRNA and the dNP2-HA2 peptide was requested to Bioneer and Genscript, respectively.

EXAMPLE 1

Formation of dNP2-siChi3l1 Complex

2 μg of the siChi3l1 was allowed to react with 70 μg of the dNP2-HA2 peptide for 30 min at room temperature in the dark to prepare dNP2-siChi3l1 complex in which the siChi3l1 was fused with the dNP2-HA peptide.

COMPARATIVE EXAMPLE 1

Synthesis and Isolation/Purification of dNP2-siEGFP

The cell-penetrating peptide having the sequence set forth in SEQ ID NO: 2 prepared in Preparative Example 1 was fused with siRNA for enhanced green fluorescent protein (EGFP). To this end, the entire procedure of Example 1 was repeated except that EGFP siRNA was used instead of siRNA. The EGFP siRNA was AccuTarget™ Positive Control siRNAs available from Bioneer.

EXPERIMENTAL EXAMPLE 1

Role of Chi3l1 During T Cell Activation and Proliferation

Figure 2:
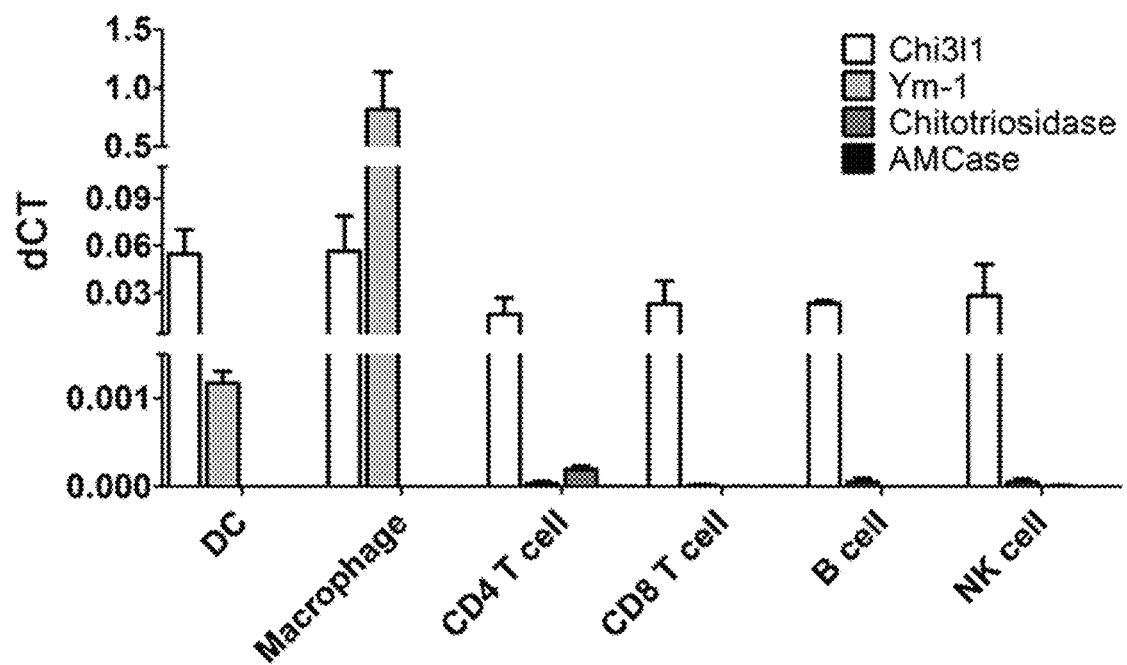
FIG. 2 shows the expression of chitinase and the Chi3l1 gene, the Chi3l3 (Ym-1) gene, chitotriosidase, and AMCase during proliferation of splenic immune cells.

FIG. 2 shows the expression of chitinase and Chi3l1, Chi3l3 (Ym-1), chitotriosidase, and AMCase during proliferation of splenic immune cells.

Each splenic immune cell was sorted by FACS. Surface markers for sorting were CD11c$^+$MHCII$^+$: DC; CD11c$^-$CD11b$^+$: macrophage; CD8$^+$CD4$^-$CD62$^+$CD44$^-$: naïve CD8 T cell; CD4$^+$CD8$^-$CD62L$^+$CD44$^-$: naïve CD4 T cell; CD19$^+$: B cell; and CD3$^-$NK1.1$^+$: NK cell. 6 RNAs were extracted from immune cell populations and cDNA was synthesized from 100 ng of the total RNA. The target levels were measured by RT-PCR (n=4).

As shown in FIG. 2, when Chi3l1, Chi3l3 (Ym-1), chitotriosidase, and AMCase mRNA levels in splenic macrophages, DC, T cells, B cells, and NK cells were analyzed and compared, chitinase and Chi3l3 (Ym-1) were highly expressed in splenic macrophages. The highest Chi3l1 expressions in CD4, CD8 T cells, B cells, and NK cells Chi3l1 were observed.

Figure 3:
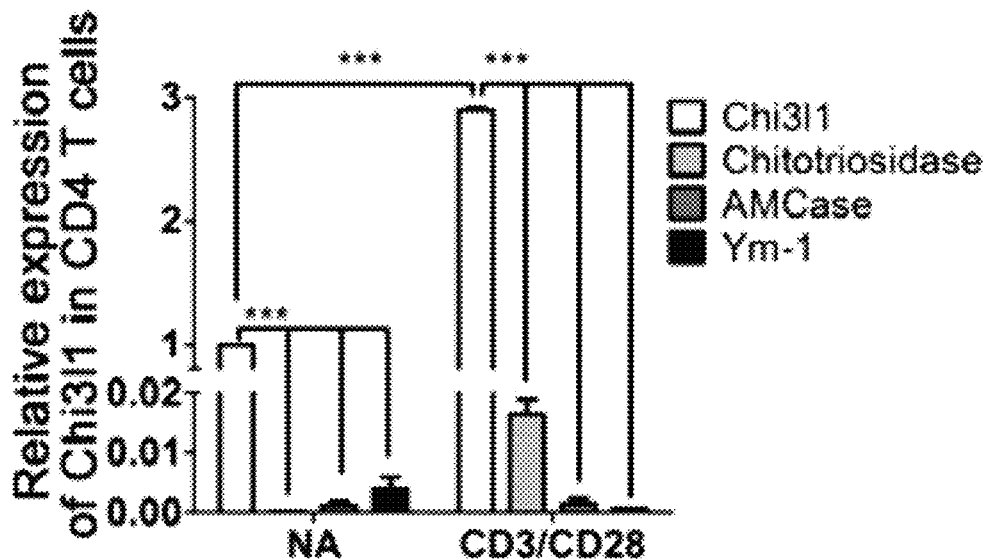
FIG. 3 shows the expression of chitinase-like proteins (Chi3l1, Ym-1) and chitinases (chitotriosidase, AMCase) in naïve CD4 T cells and activated CD4 T cells.
Figure 4:
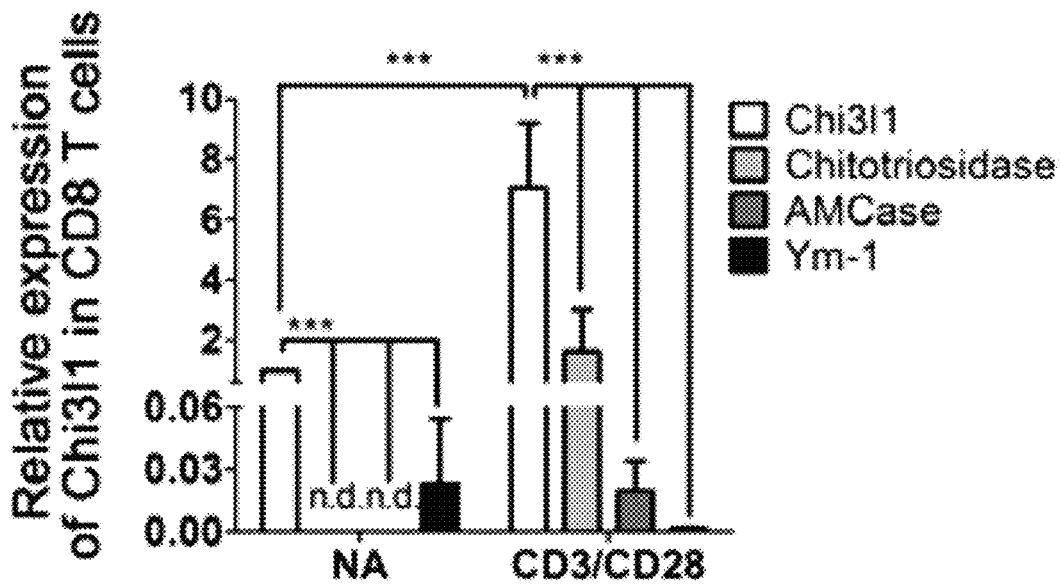
FIG. 4 shows the expression of chitinase-like proteins (Chi3l1, Ym-1) and chitinases (chitotriosidase, AMCase) in naïve CD8 T cells and activated CD8 T cells.

FIG. 3 shows the expression of chitinase-like proteins (Chi3l1, Ym-1) and chitinases (chitotriosidase, AMCase) in naïve CD4 T cells and activated CD4 T cells. FIG. 4 shows the expression of chitinase-like proteins (Chi3l1, Ym-1) and chitinases (chitotriosidase, AMCase) in naïve CD8 T cells and activated CD8 T cells.

As shown in FIGS. 3 and 4, relative Chi3l1 expressions in non-activated cells (NA) were observed. Chi3l1 was highly induced in anti-CD3 and anti-CD28 antibodies, suggesting a potential role of Chi3l1 during T cell activation.

Figure 5A:
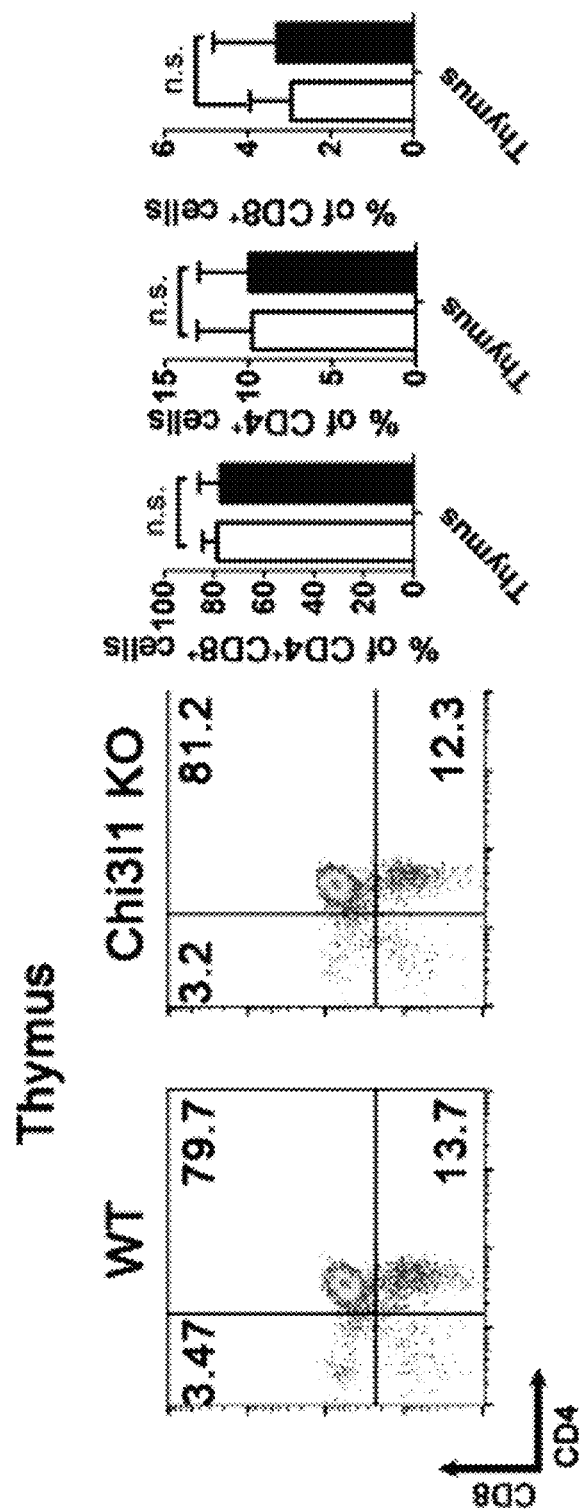
FIGS. 5A-5G compares the proliferation of immune cells of wild-type (WT) and Chi3l1 KO mice in primary and secondary lymphatic vessels. Specifically.
Figure 5B:
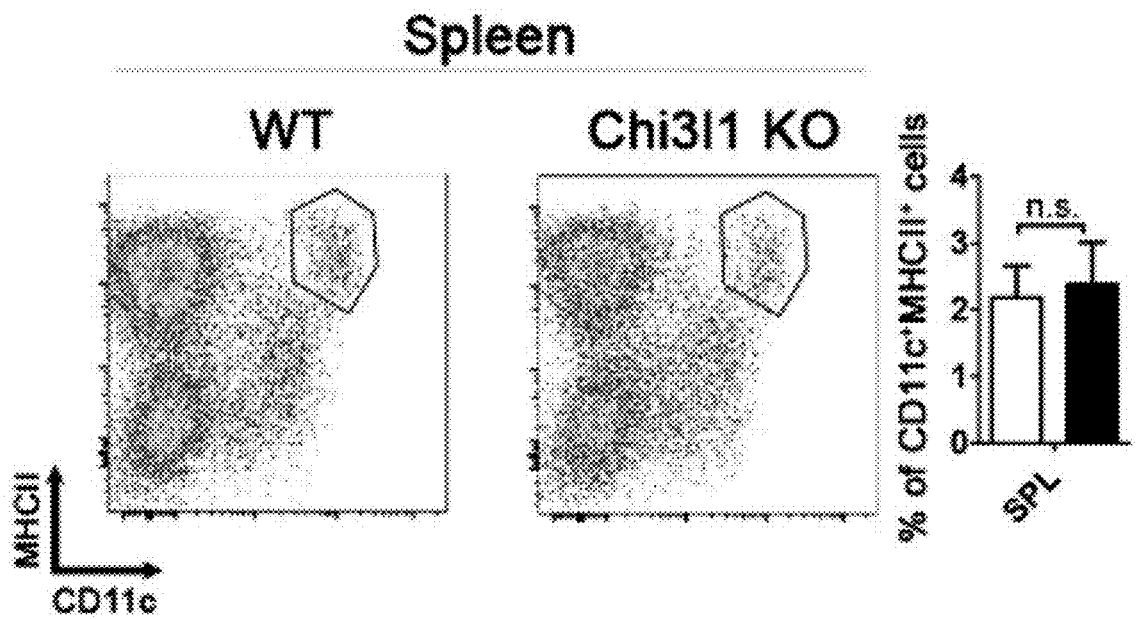
Figure 5C:
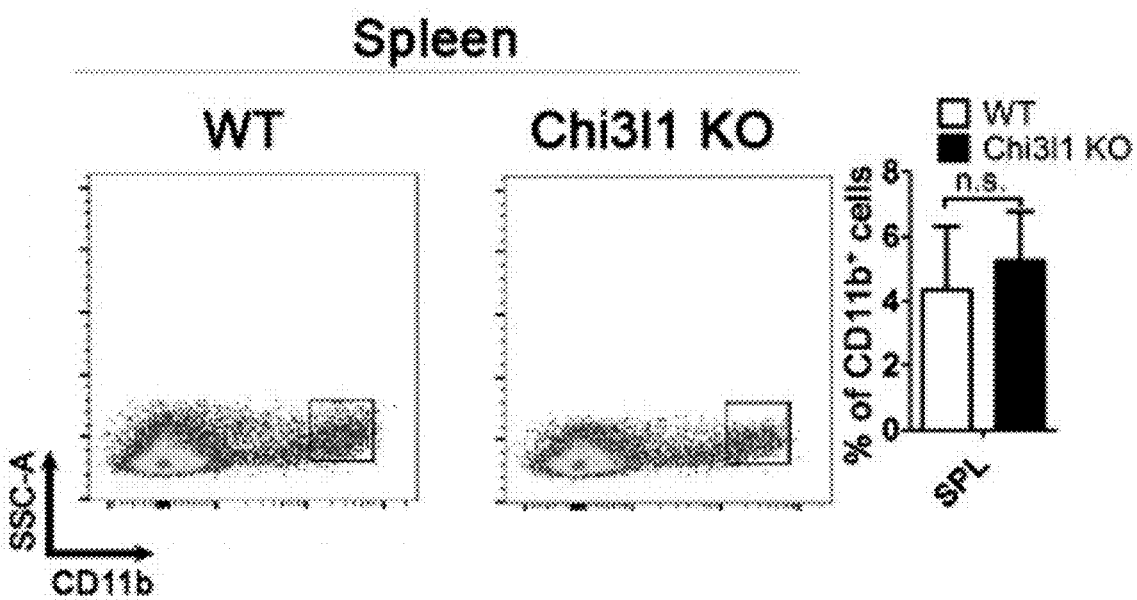
Figure 5D:
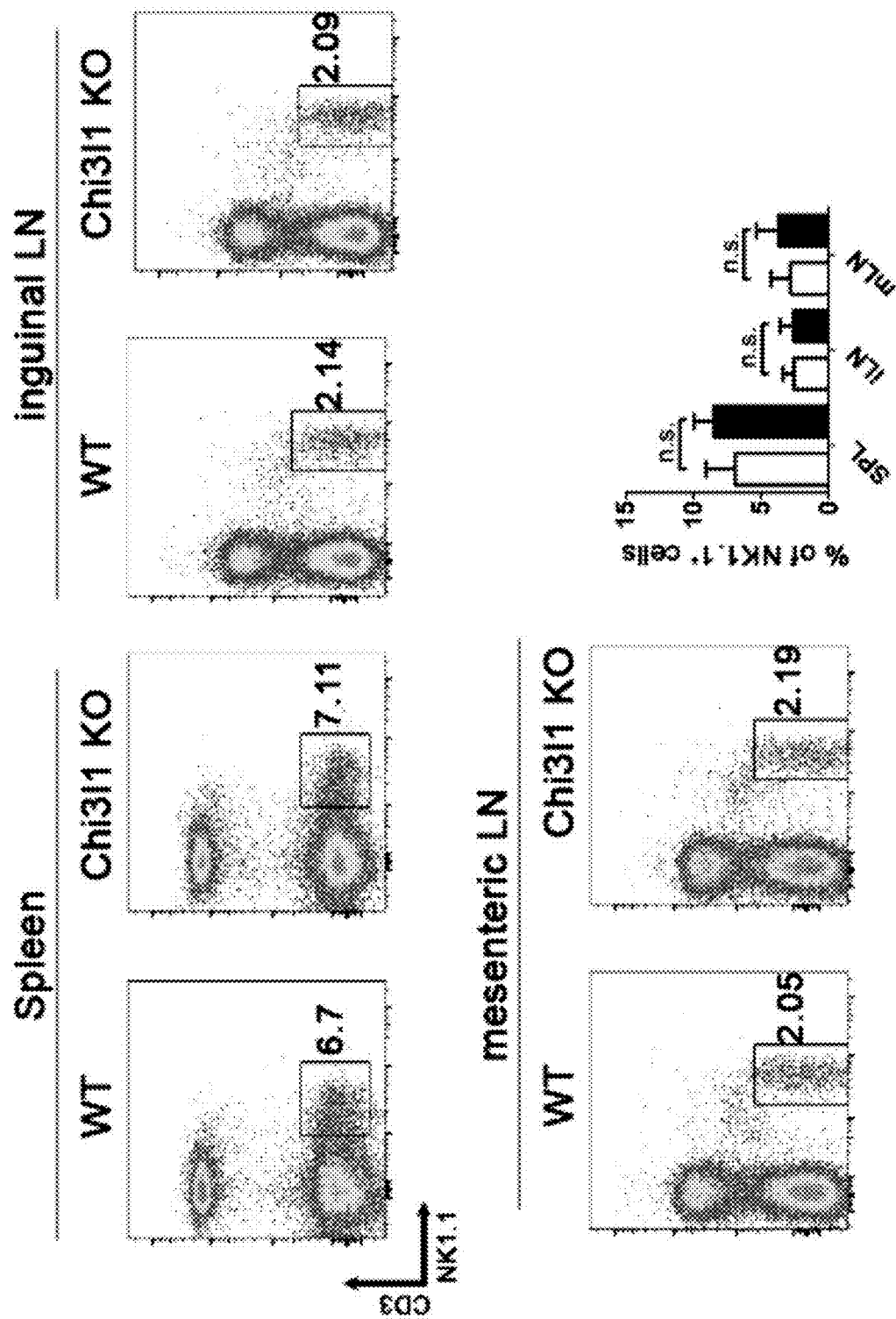
Figure 5E:
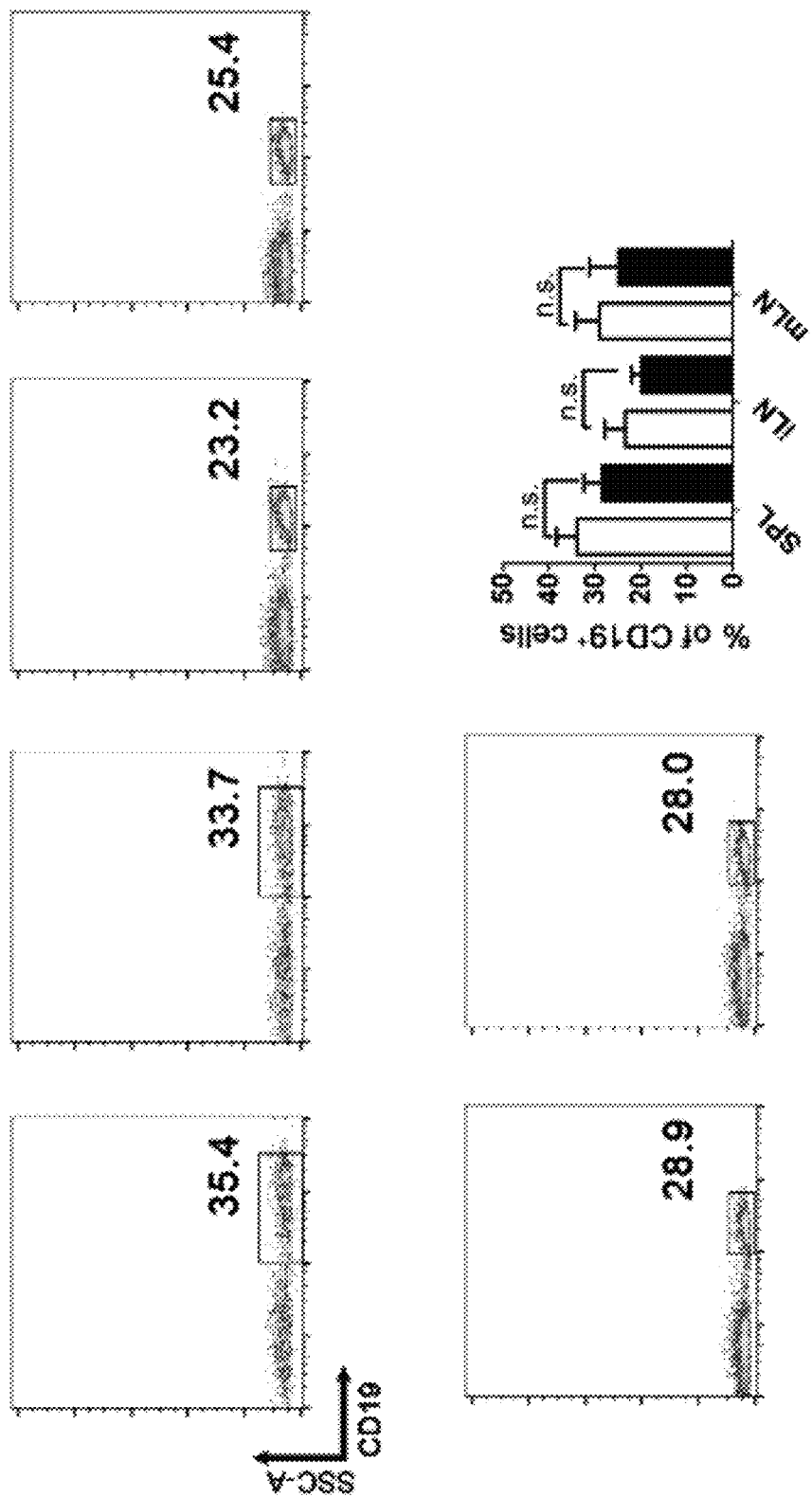
Figure 5F:
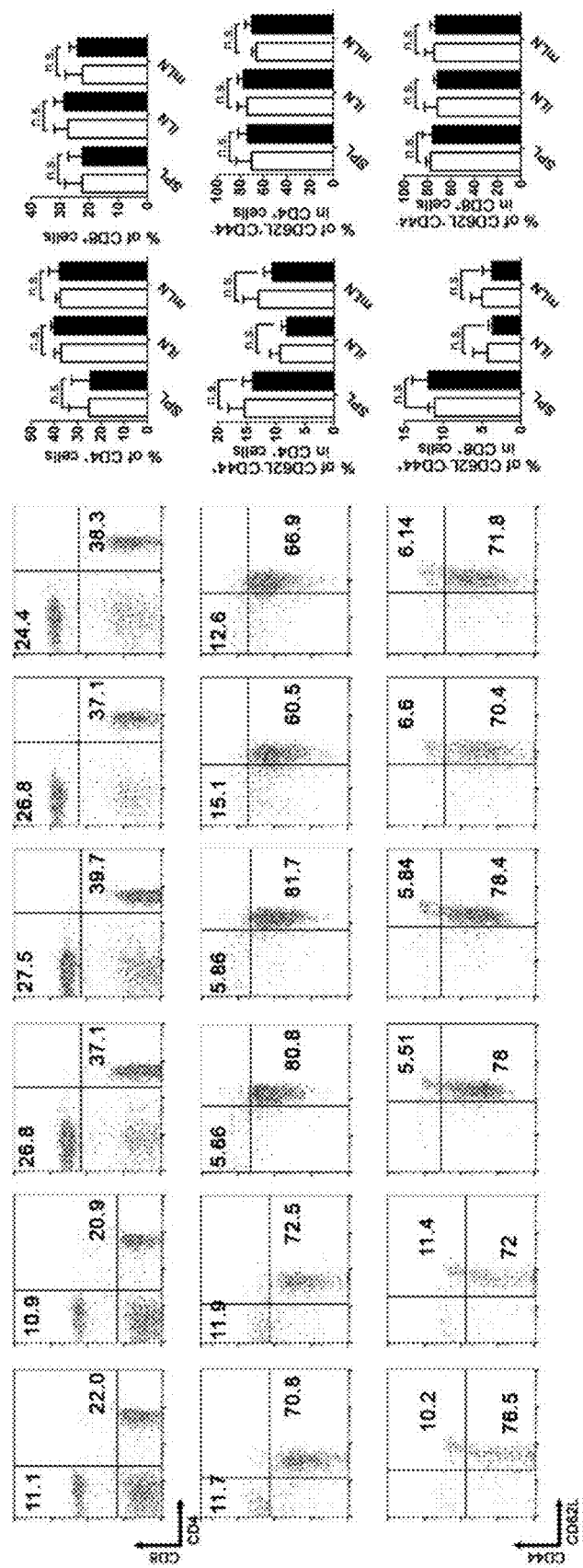
Figure 5G:
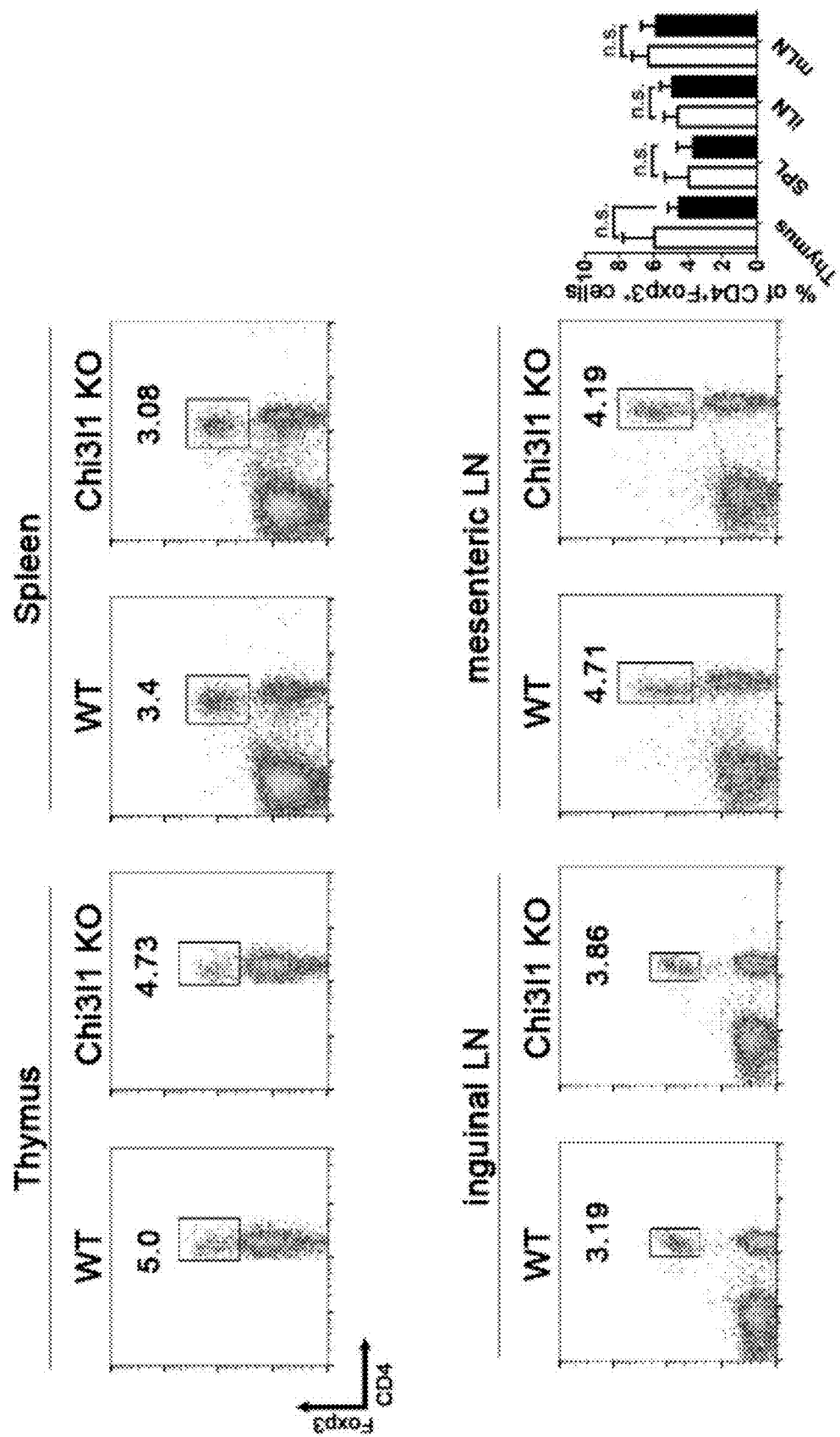

FIGS. 5A-5G compare the proliferation of immune cells of wild-type (WT) and Chi3l1 KO mice in primary and secondary lymphatic vessels. Specifically, FIG. 5A shows the percentages of CD4$^+$CD8$^+$cells, CD4+cells, and CD8+ cells in the thymus, which were analyzed by flow cytometry, FIGS. 5B and 5C show the percentages of dendritic cells (CD11c$^+$MHCII$^+$) and macrophages (CD11b$^+$) in the spleen, which were analyzed by flow cytometry, FIGS. 5D to 5F show the results of flow cytometry for immune cells in the spleen, peripheral lymph node, and mesenteric lymph node, and FIG. 5G shows the Foxp3 expression in CD4 T cells, which was analyzed by flow cytometry. Data are mean±SD of at least five independent experiments.

As shown in FIGS. 5A-5G, no significant abnormalities were noted in immune cells development between WT and Chi3l1 KO mice.

Figure 6A:
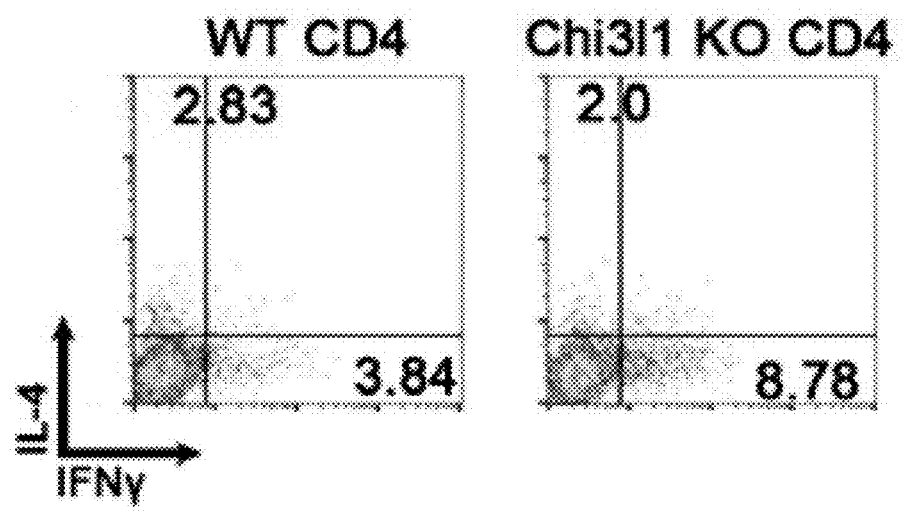
FIG. 6A shows the expression of IFNγ and IL-4 in MACS-sorted WT and Chi3l1 KO naïve CD4 T cells, which was measured by flow cytometry.
Figure 6B:
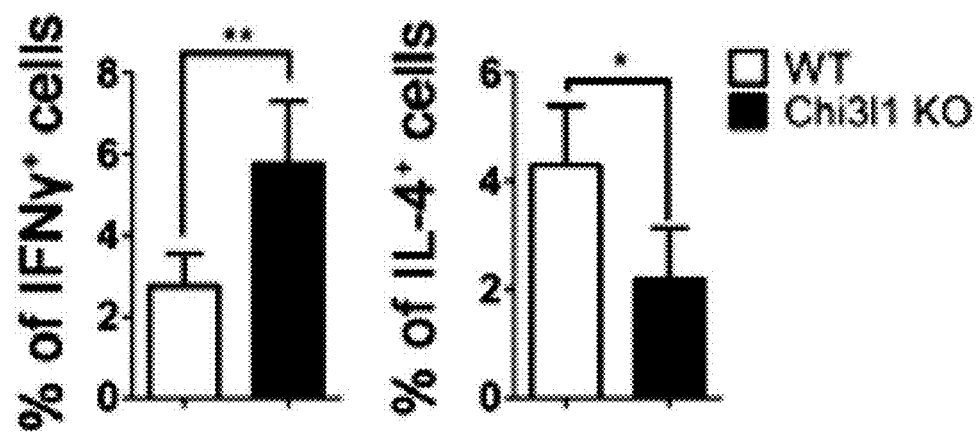
FIG. 6B shows the quantified results of FIG. 6A. WT and Chi3l1 KO naïve CD4 T cells were activated by TcR stimulation for 3 days.
Figure 6C:
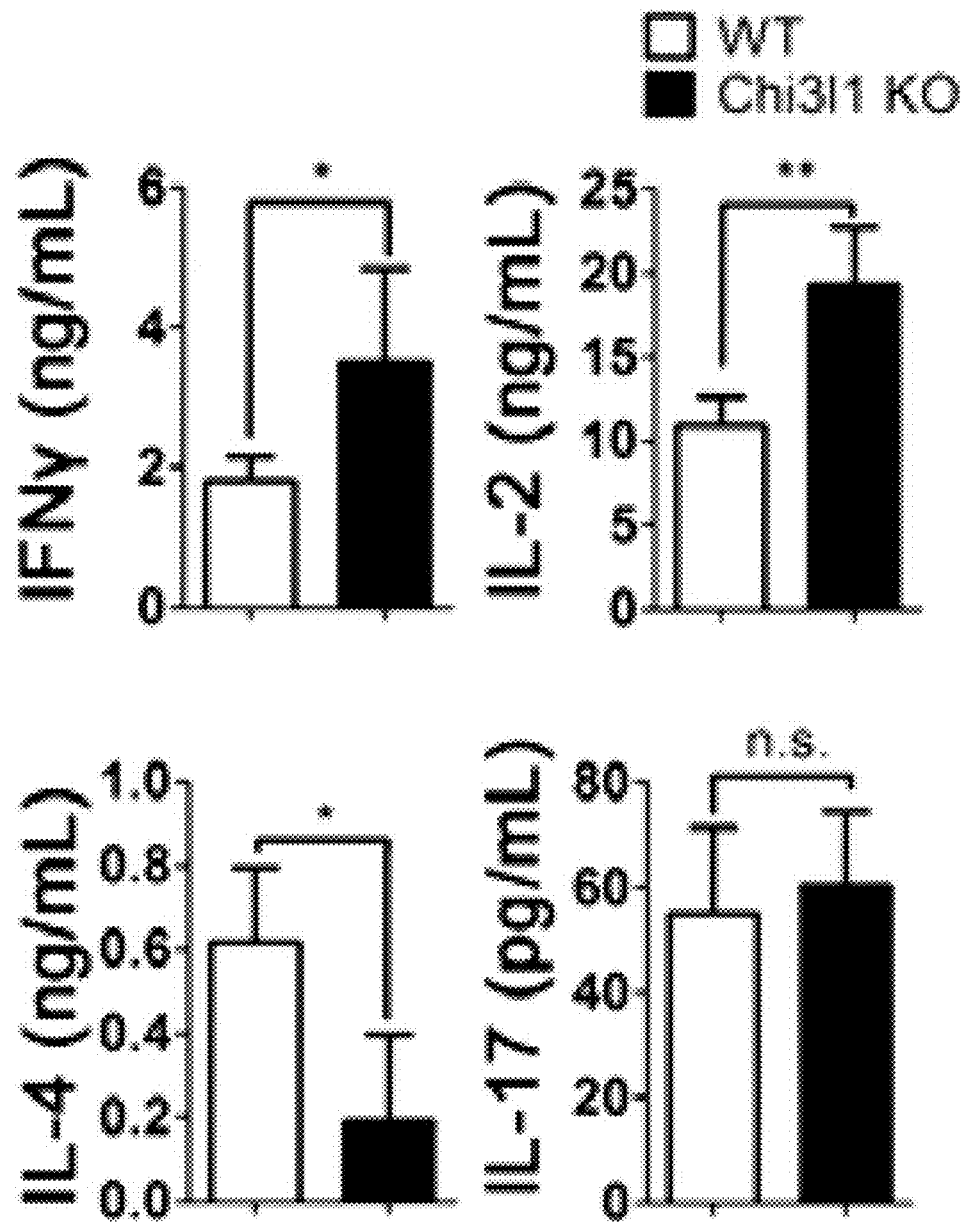
FIG. 6C shows the expression of IFNγ, IL-2, IL-4, and IL-17 cytokines in a culture supernatant of splenic cells from WT and Chi3l1 KO mice after TcR stimulation, which was measured by ELISA. Data are mean±SD of three independent experiments. n.s., not significant; *p<0.05, p<0.01,*p<0.001.

FIG. 6A shows the expression of IFNγ and IL-4 in MACS-sorted WT and Chi3l1 KO naïve CD4 T cells, which was measured by flow cytometry. FIG. 6B shows the quantified results of FIG. 6A. WT and Chi3l1 KO naïve CD4 T cells were activated by TcR stimulation for 3 days. FIG. 6C shows the expression of IFNγ, IL-2, IL-4, and IL-17 cytokines in a culture supernatant of splenic cells from WT and Chi3l1 KO mice after TcR stimulation, which was measured by ELISA. Data are mean±SD of three independent experiments. n.s., not significant; *$p<0.05$, $p<0.01$, *$p<0.001$.

In FIGS. 6A-6C, to investigate whether Chi3l1 is a negative regulator of T cell activation, MACS-purified naïve CD4 and FACS-purified CD8 T cells from wild type (WT) and Chi3l1 KO mouse splenocytes were activated by anti- CD3 and anti-CD28 antibodies for 3 days. Cytokine flow cytometric analysis and ELISA assay demonstrated that Chi3l1 deficiency in CD4 T cells significantly increased IFNγ and IL-2 production, while IL-4 production decreased and IL-17 production was not affected.

Figure 7A:
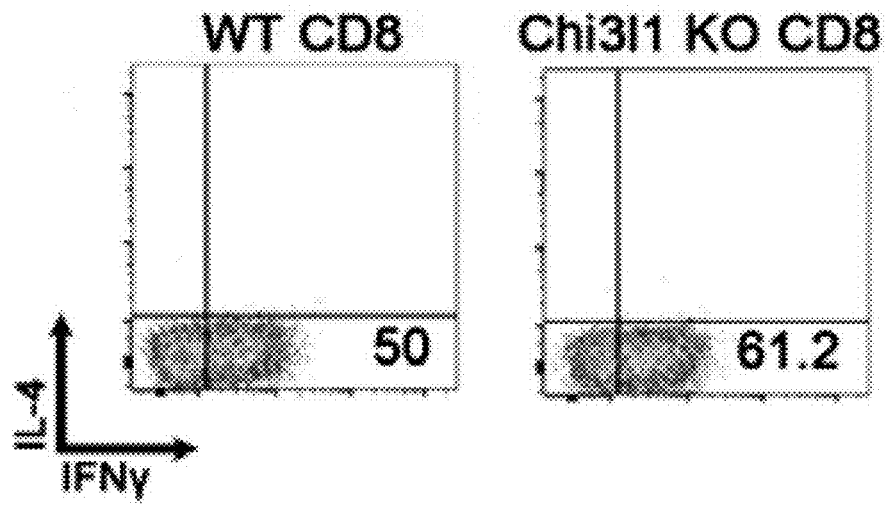
FIG. 7A shows the expression of IL-2 cytokines and IFNγ in WT naïve CD8 T cells and Chi3l1 KO naïve CD8 T cells activated by antibodies for 3 days.
Figure 7B:
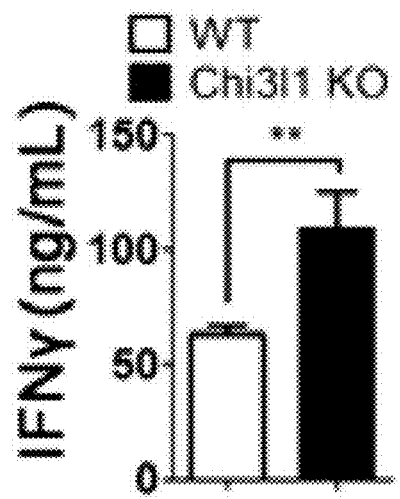
FIG. 7B shows the expression levels of IFNγ in WT naïve CD8 T cells and Chi3l1 KO naïve CD8 T cells.
Figure 7B:
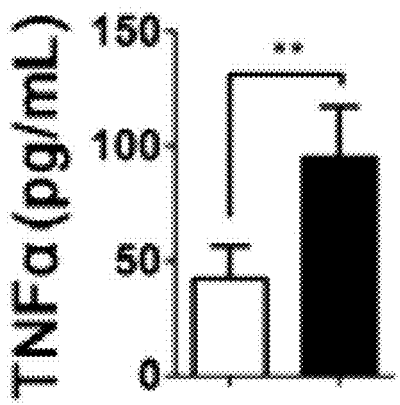
Figure 7C:
FIG. 7C shows IFNγ and TNFα in the culture supernatants of FIG. 7A, which was measured by ELISA. Data are mean +SD of three independent experiments. n.d., not detected; n.s., not significant; *p<0.05, p<0.01, *p<0.001.

FIG. 7A shows the expression of IL-2 cytokines and IFNγ in WT and Chi3l1 KO naïve CD8 T cells activated by antibodies for 3 days. FIG. 7B shows the expression levels of IFNγ in WT and Chi3l1 KO naïve CD8 T cells. FIG. 7C shows IFNγ and TNFα in the culture supernatants of FIG. 7A, which was measured by ELISA. Data are mean±SD of three independent experiments. n.d., not detected; n.s., not significant; *p<0.05, p<0.01, * p<0.001.

As shown in FIGS. 7A-7C, there was increased IFNγ and TNFα expression in Chi3l1 KO CD8 T cells, suggesting that Chi3l1 is involved in T cell activation. Specifically, Chi3l1 negatively regulates IFNγ, TNFα, and IL-2 and does not negatively regulates IL-4 and IL-17. Because IL-2 and IFNγ are important cytokines for T cell proliferation, the proliferation properties of Chi3l1 KO T cells compared to wild type were confirmed.

Figure 8A:
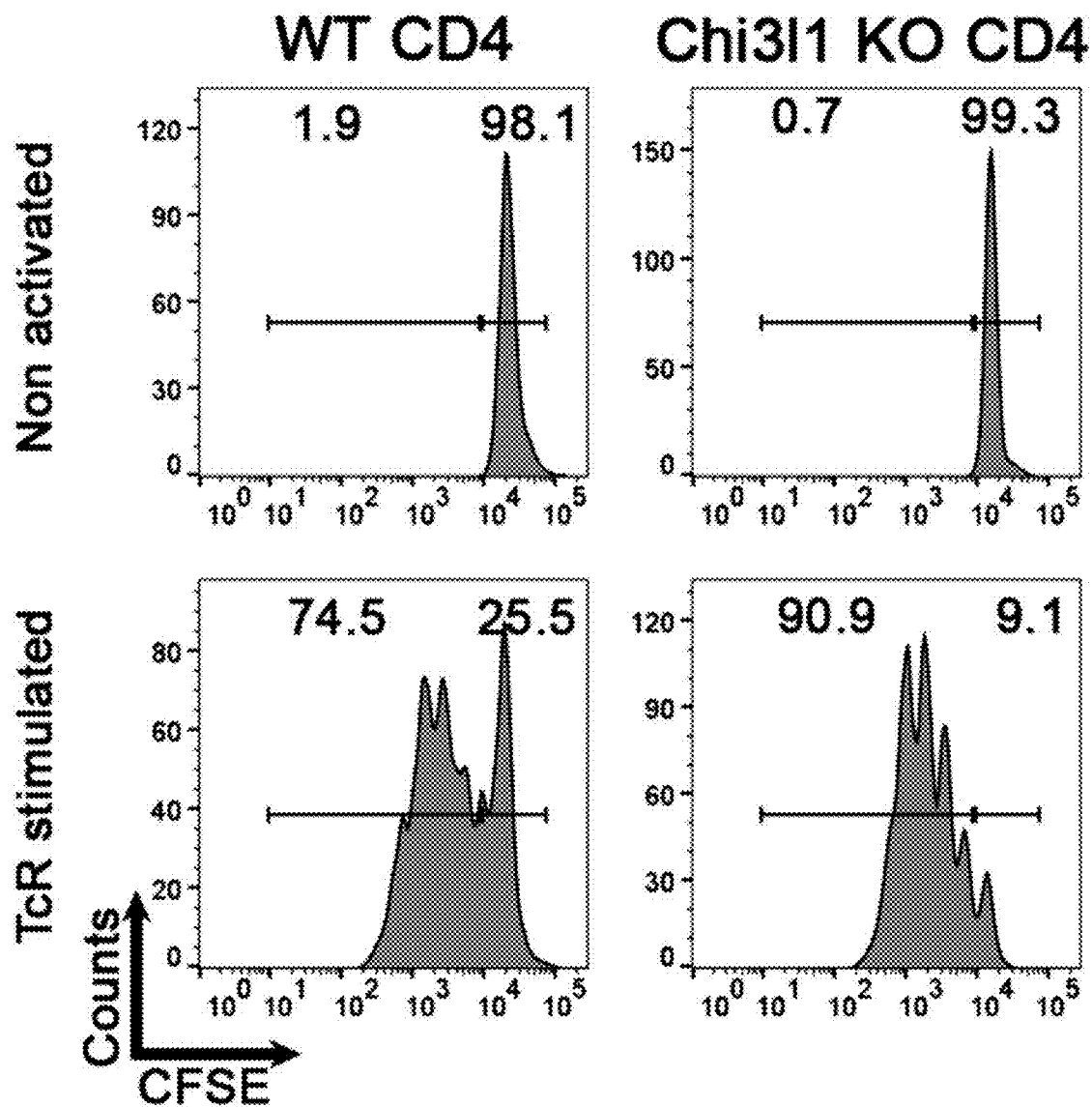
FIG. 8A shows the contents of divided WT CD4 T cells and Chi3l1 KO CD4 T cells after 3 days under non-activated (upper) and anti-CD3 and CD28 stimulation conditions (lower), which were analyzed by CFSE assay.
Figure 8B:
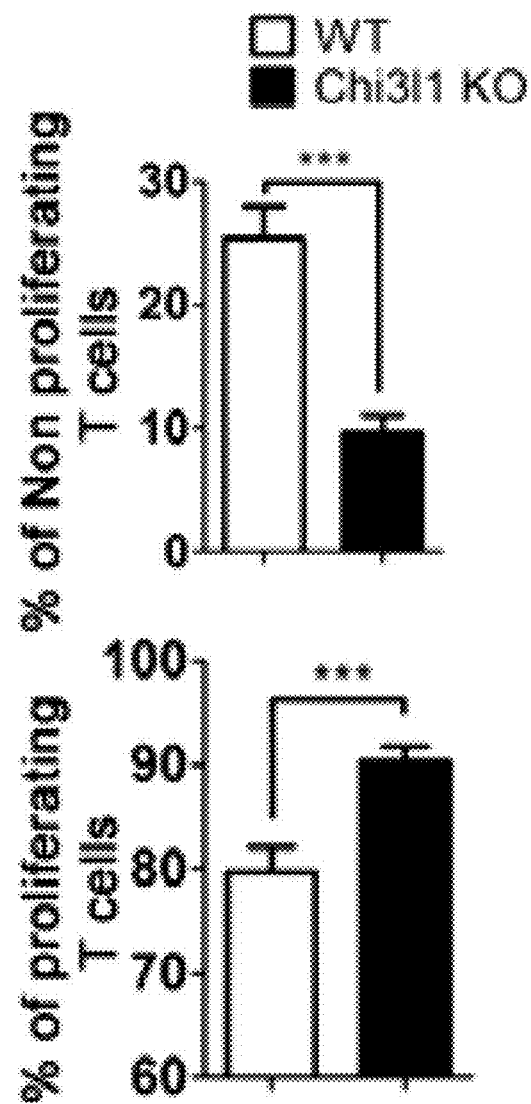
FIG. 8B shows the percentages of divided cells and non-divided cells from the results of FIG. 8A. Data are mean±SD of three independent experiments. n.d., not detected; n.s., not significant; *p<0.05, p<0.01, *p<0.001.

FIG. 8A shows the contents of divided WT and Chi3l1 KO CD4 T cells after 3 days under non-activated (upper) and anti-CD3 and CD28 stimulation conditions (lower), which were analyzed by CFSE assay. FIG. 8B shows the percentages of divided cells and non-divided cells from the results of FIG. 8A. Data are mean±SD of three independent experiments. n.d., not detected; n.s., not significant; *p<0.05, p<0.01, * p<0.001.

As shown in FIG. 8A, CFSE-labeled Chi3l1 KO CD4 T cells showed a higher proportion of divided cells in response to TcR stimuli compared to control WT CD4 T cells.

Figure 9A:
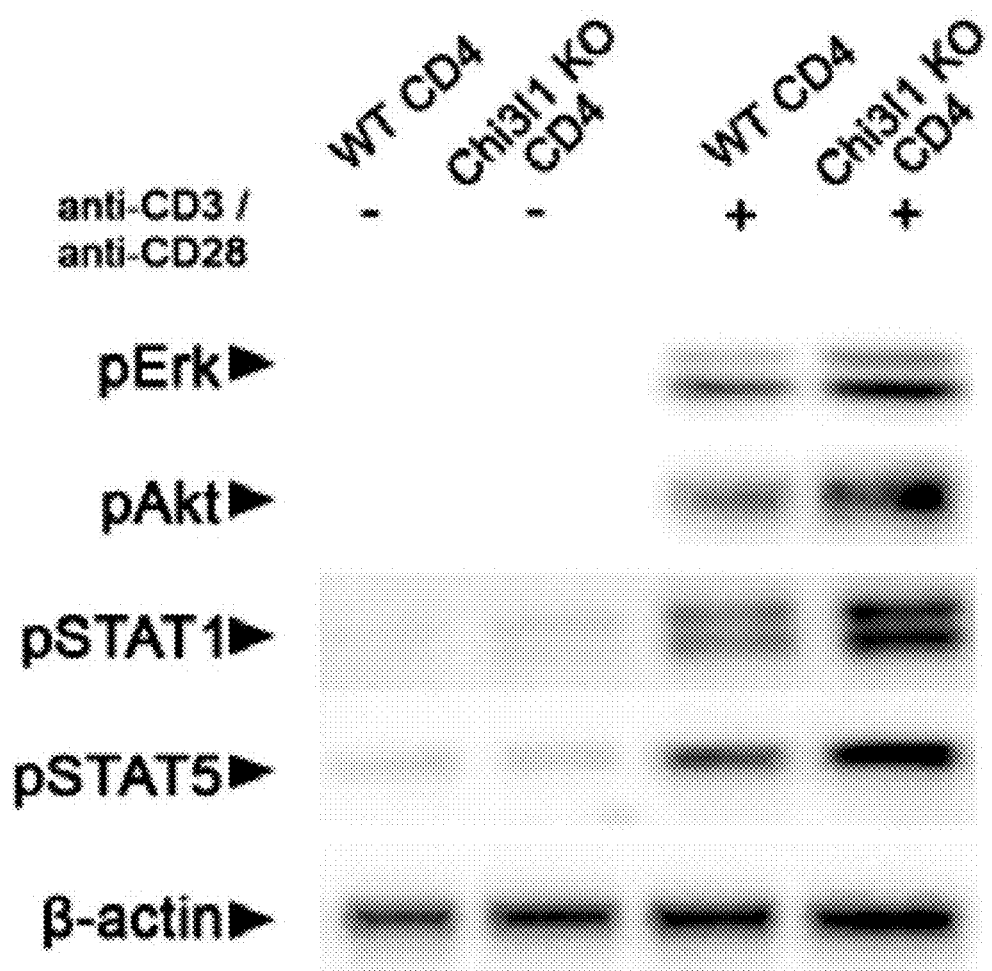
FIG. 9A shows the results of Western blotting for WT CD4 T cells; Chi3l1 KO naïve CD4 T cells; WT CD4 T cells stimulated with anti-CD3 and anti-CD28; and Chi3l1 KO naïve CD4 T cells stimulated with anti-CD3 and anti-CD28.
Figure 9B:
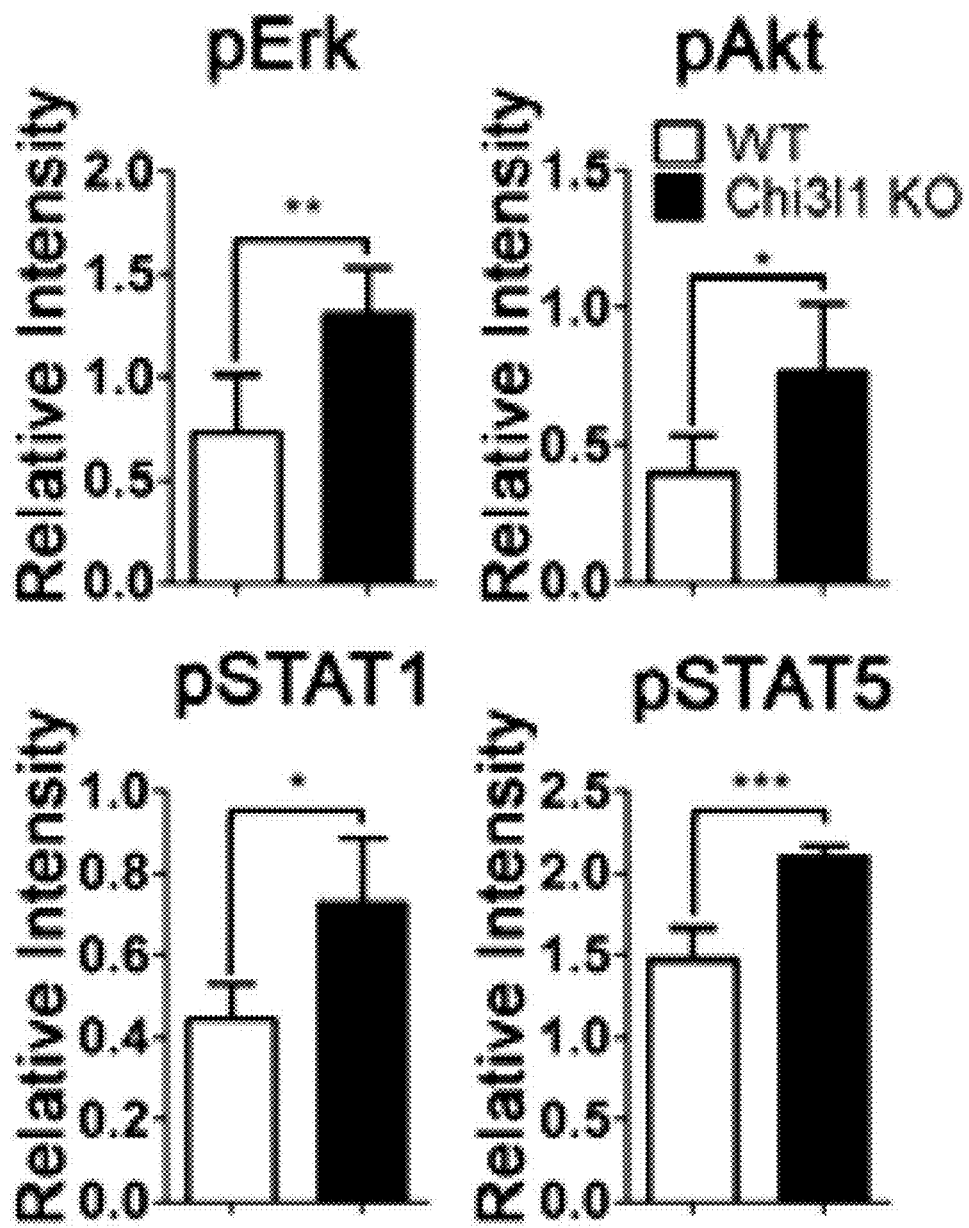
FIG. 9B shows the relative concentrations of target molecules calculated by normalization of FIG. 9A to β-actin. Data are mean±SD of three independent experiments. n.d., not detected; n.s., not significant; *p<0.05, p<0.01, *p<0.001.

FIG. 9A shows the results of Western blotting for WT CD4 T cells; Chi3l1 KO naïve CD4 T cells; WT CD4 T cells stimulated with anti-CD3 and anti-CD28; and Chi3l1 KO naïve CD4 T cells stimulated with anti-CD3 and anti-CD28. FIG. 9B shows the relative concentrations of target molecules calculated by normalization of FIG. 9A to β-actin. Data are mean±SD of three independent experiments. n.d., not detected; n.s., not significant; *p<0.05, p<0.01, * p<0.001.

As shown in FIGS. 9A-9B, phosphorylation of Akt, Erk, STAT1, and STAT5 was increased in Chi3l1 KO T cells, suggesting that Chi3l1 is an important factor for regulating T cell proliferation.

Collectively, these results demonstrate that Chi3l1 is expressed in T cells and regulate T cell activation and proliferation.

EXPERIMENTAL EXAMPLE 2

Chi3l1 Inhibits Th1 Differentiation

FIGS. 10A-10G show the differentiation patterns of Chi3l1 KO CD4 T cells into Th1 and Th2 through sensitive IFNγ response.

Figure 10A:
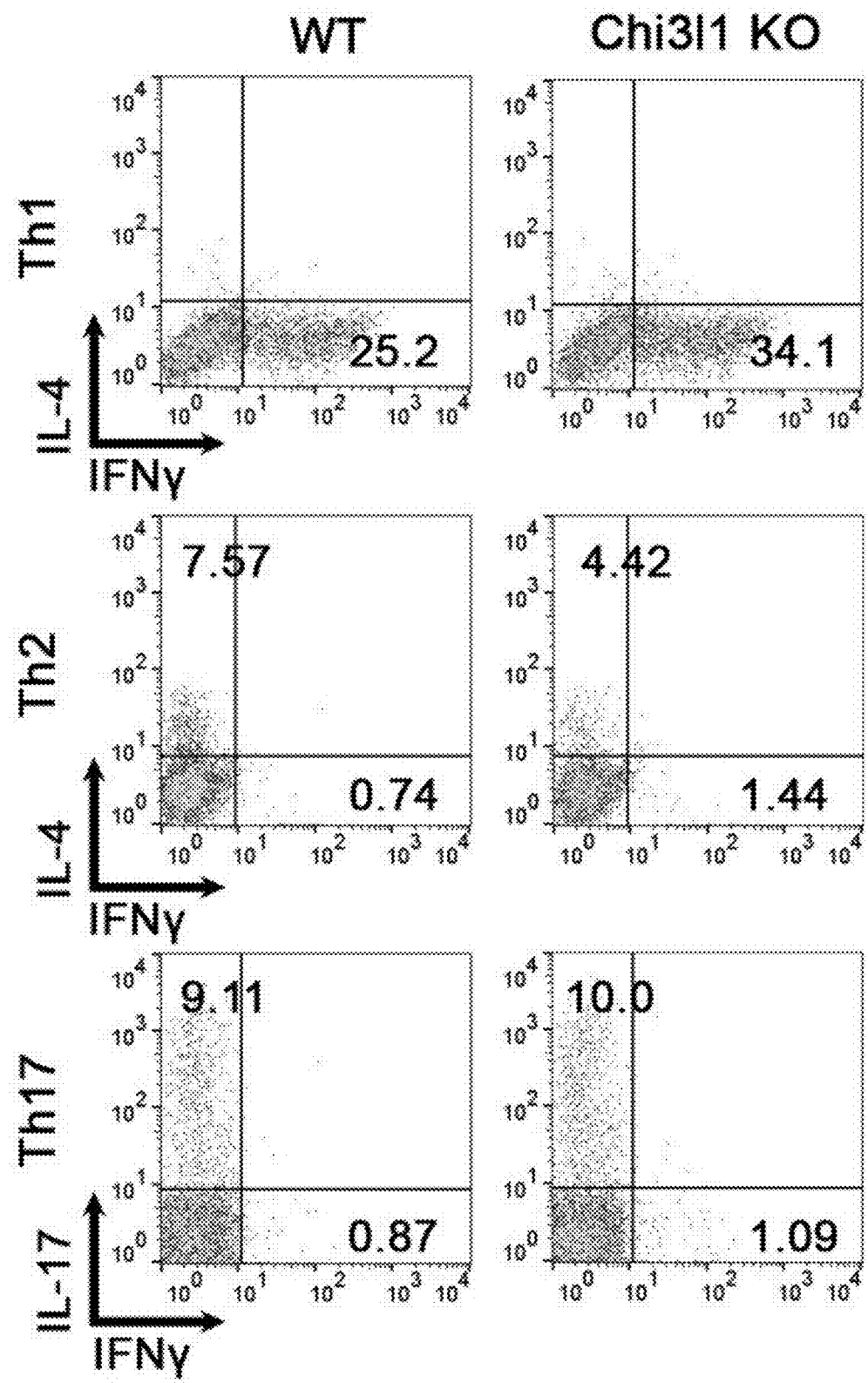
FIGS. 10A-10G show the differentiation patterns of Chi3l1 KO CD4 T cells into Th1 and Th2 through sensitive IFNγ response. Specifically.
Figure 10B:
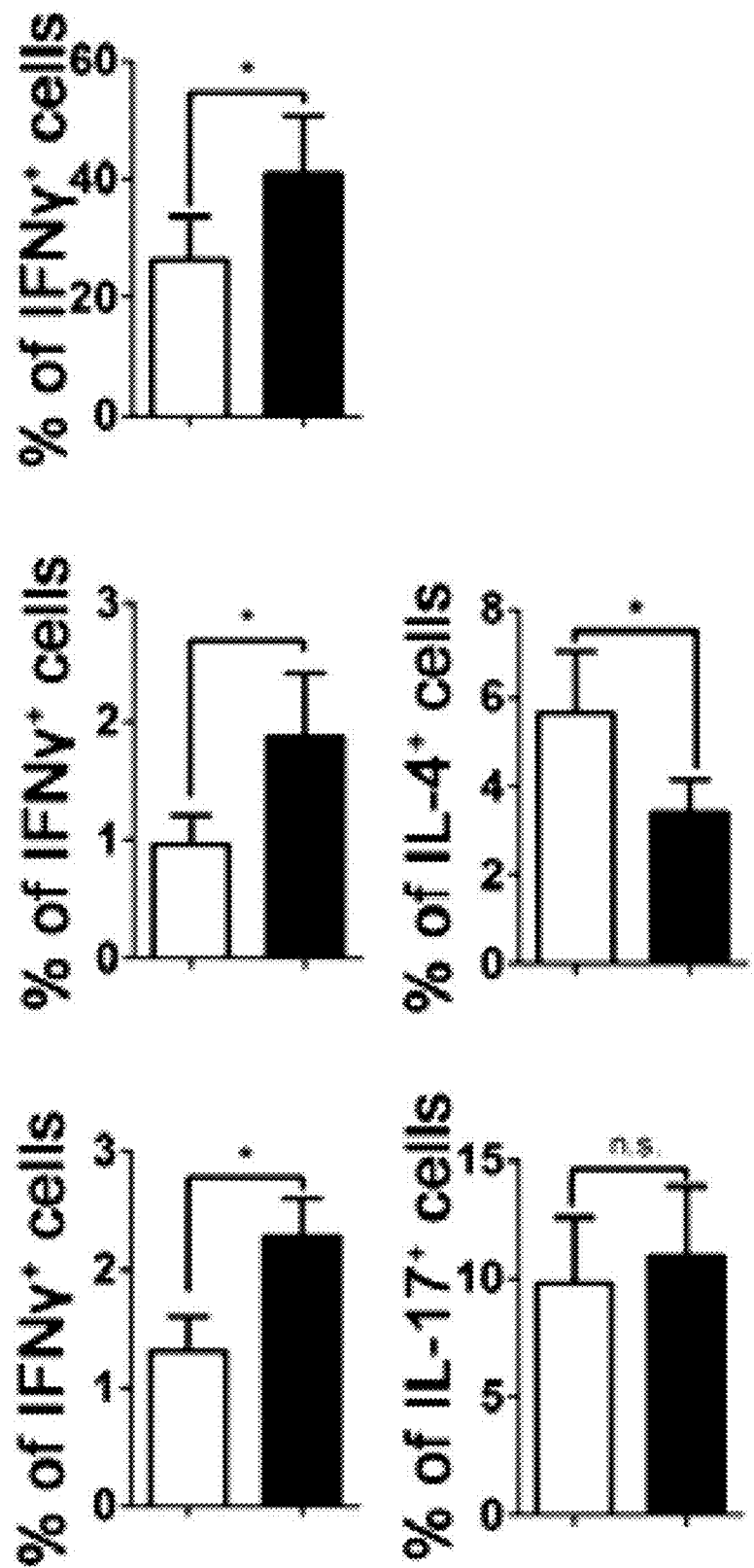

Specifically, FIG. 10A shows the differentiation patterns of WT and Chi3l1 KO naïve CD4 T cells into Th1, Th2, and Th17 under specific cytokine-skewing condition. Intracellular cytokine staining was performed to analyze lineage-specific cytokine expression. FIG. 10B shows the percentages of cytokines corresponding to subsets of the results of FIG. 10A. The top graph represents the results for Th1 cells, the middle graph represents the results for Th2 cells, and the bottom graph represents the results for Th17. Data are mean±SD of a total of three independent experiments. n.s., not significant; *p <0.05,** p<0.01.

Because Chi3l1 deficiency induces increased IFNγ and IL-2 production but causes decreased IL-4 production, as demonstrated in the foregoing experiment, it was hypothesized to regulate effector T cell differentiation between Th1 and Th2. To investigate whether Chi3l1 regulates Th1 and Th2 differentiation, the differentiation patterns of MACS-sorted CD4 $^+$CD62L$^{high}$CD44$^{low}$ WT and Chi3l1 KO naïve CD4 T cells into Th1, Th2, and Th17 cells during culture under various differentiation conditions were analyzed.

As shown in FIGS. 10A and 10B, the proportion of IFNγ-producing cells significantly increased not only in Th1 but also in Th2 and Th17 conditions while IL-4 in Th2 was decreased and showed no difference in Th17.

Figure 10C:
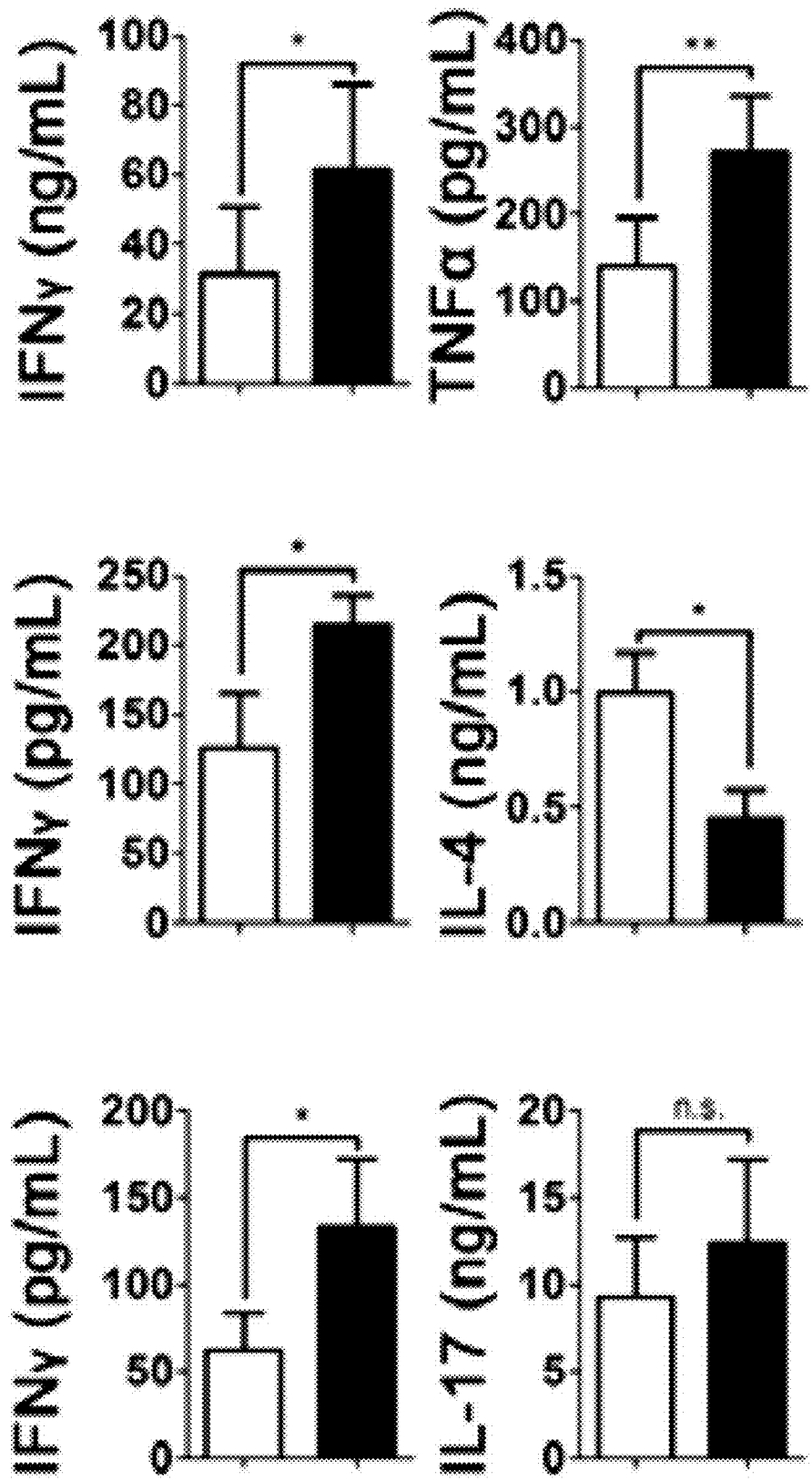

FIG. 10C shows the results of ELISA assay for IFNγ, TNFα, IL-4, and IL-17 production in the culture supernatants of FIG. 10A. Data are mean±SD of a total of three independent experiments. n.s., not significant; *p<0.05,** p<0.01.

As shown in FIG. 10C, accumulated cytokines in supernatants showed equivalent patterns, as in FIGS. 10A and 10B.

Figure 10D:
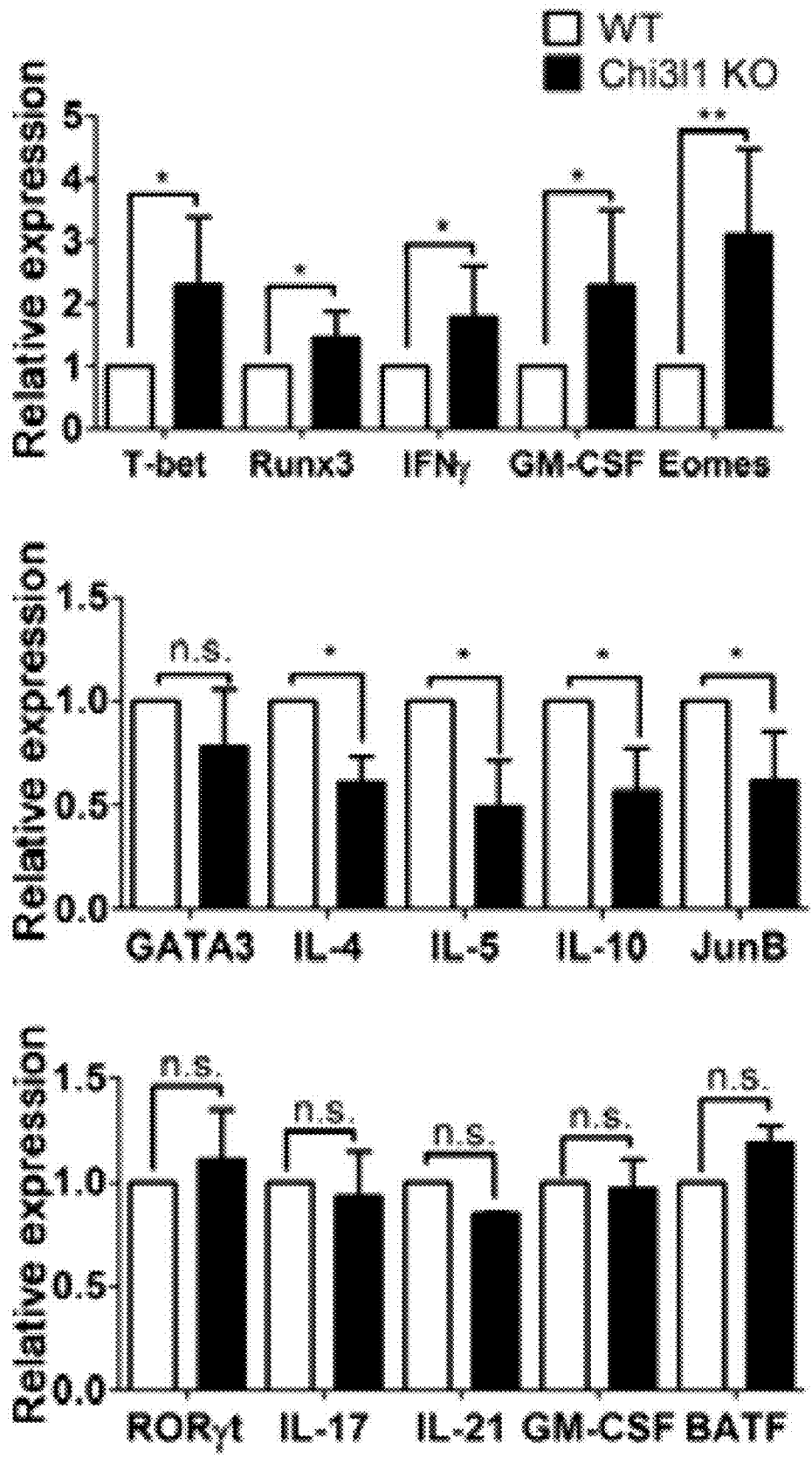

FIG. 10D shows the RNA expression levels of cytokines and transcription factors of differentiated T cells in FIG. 10A, which were analyzed by quantitative real-time PCR. Data are mean±SD of a total of three independent experiments. n.s., not significant; *p <0.05,** p<0.01.

As shown in FIG. 10D, T-bet, Runx3, and Eomes, which are important transcription factors of Th1 differentiation, increased in Chi3l1-deficient Th1 cells with increased IFNγ and GM-CSF. JunB, which is important for IL-4-related Th2 differentiation, was significantly reduced, and no differences were observed in Th17-related factors.

Figure 10E:
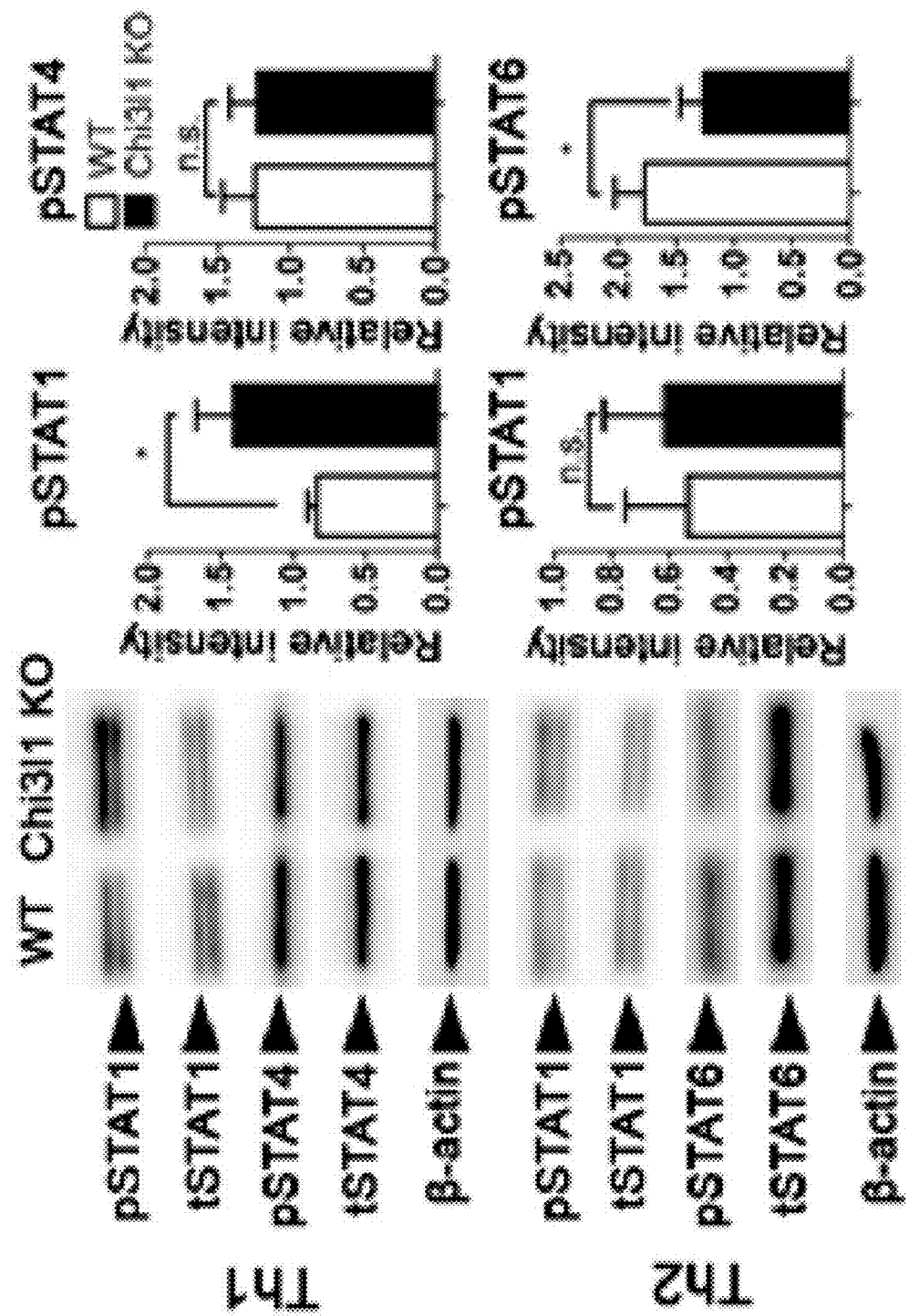

FIG. 10E shows the STAT phosphorylation of WT and Chi3l1 KO Th1 and Th2 cells measured by Western blotting (left) and the total STAT quantified by relative densitometric analysis of Western blotting (right). Data are mean±SD of a total of three independent experiments. n.s., not significant; *p<0.05,** p<0.01.

As shown in FIG. 10E, in Chi3l1-deficient Th1 cells, the level of phosphorylated STAT1 was significantly increased, with no difference in the level of phosphorylated STAT4 suggesting Chi3l1 regulates IFNγ signaling not IL-12.

Figure 10F:
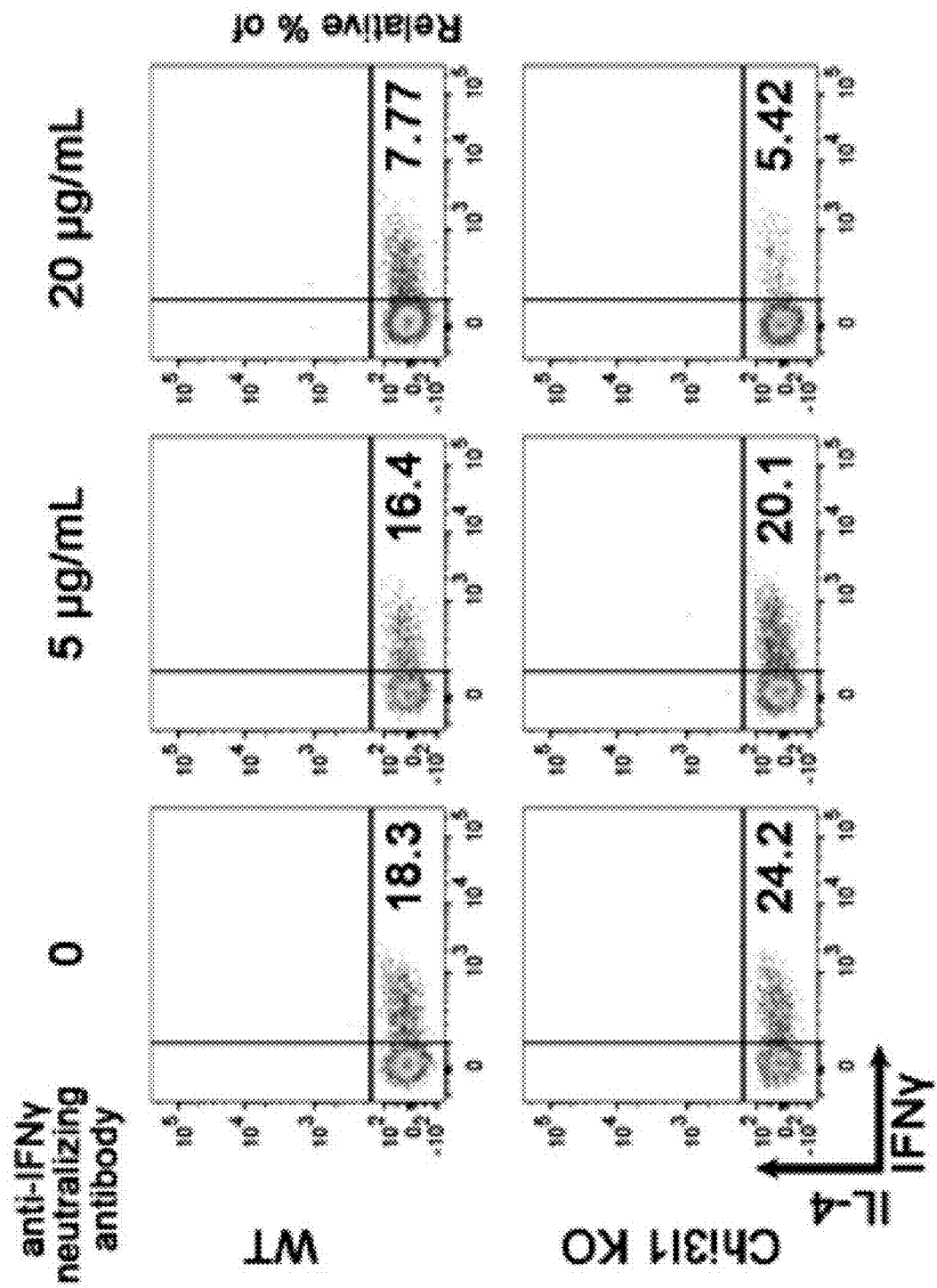
Figure 10G:
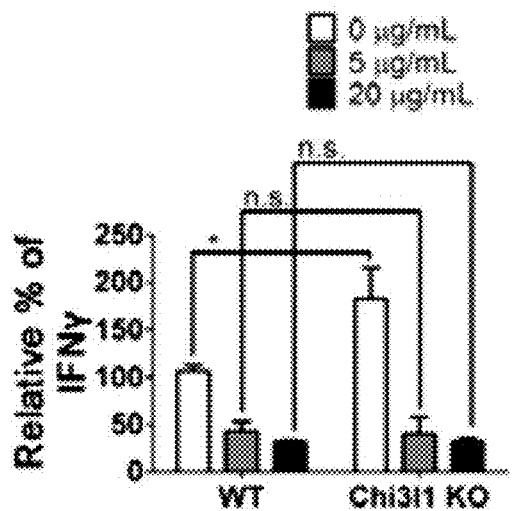

FIG. 10F shows the IFNγ and IL-4 expression assessed by intracellular staining after WT and Chi3l1 KO naïve CD4 T cells were differentiated into Th1 cells with the indicated concentrations of IFNγ neutralizing antibodies and cells were harvested 3 days after the differentiation. FIG. 10G shows the percentages of IFNγ expression relative to IFNγ expression in WT Th1 cells without IFNγ neutralizing antibody. Data are mean±SD of a total of three independent experiments. n.s., not significant; *p<0.05,** p<0.01.

As shown in FIGS. 10F and 10G, when IFNγ-neutralizing antibody was added to Th1 medium to evaluate IFNγ production, the proportion of IFNγ-producing cells was significantly increased in Chi3l1 KO Th1 cells without the IFNγ-neutralizing antibody. In WT and Chi3l1 KO Th1 cells, IFNγ production was decreased with increasing antibody dose.

EXPERIMENTAL EXAMPLE 3

Analysis of STAT1 Phosphorylation for IFNγ in naïve CD4 T Cells

The foregoing experiments demonstrated that STAT6 phosphorylation in Th2 cells was significantly decreased, suggesting that Chi3l1 can negatively regulate IFN-γ signaling to make Th2-like T cells. To confirm this IFN-γ dependency, recombinant IFN-γ was treated to WT and Chi3l1 KO naïve CD4 T cells and pSTAT1 level was analyzed.

Figure 11A:
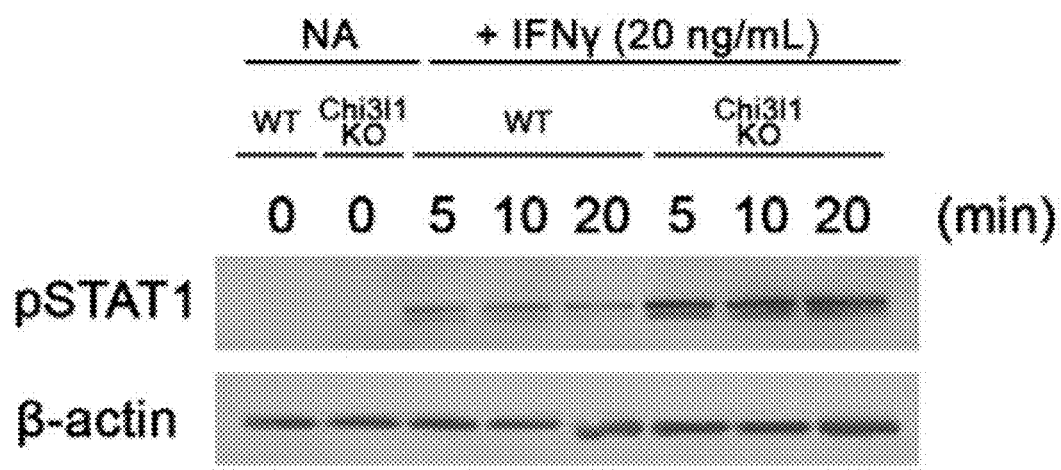
FIG. 11A shows the levels of pSTAT1 measured by Western blotting after FACS-sorted WT and Chi3l1 naïve CD4 T cells were treated with 20 ng/ml IFNγ, dissolved in cytokine-treated cells for optimum times (0, 5, 10, and 20 min), and quantified by BCA protein assay.

FIG. 11A shows the levels of pSTAT1 measured by Western blotting after FACS-sorted WT and Chi3l1 naïve CD4 T cells were treated with 20 ng/ml IFN-γ, dissolved in cytokine-treated cells for optimum times (0, 5, 10, and 20 min), and quantified by BCA protein assay.

Figure 11B:
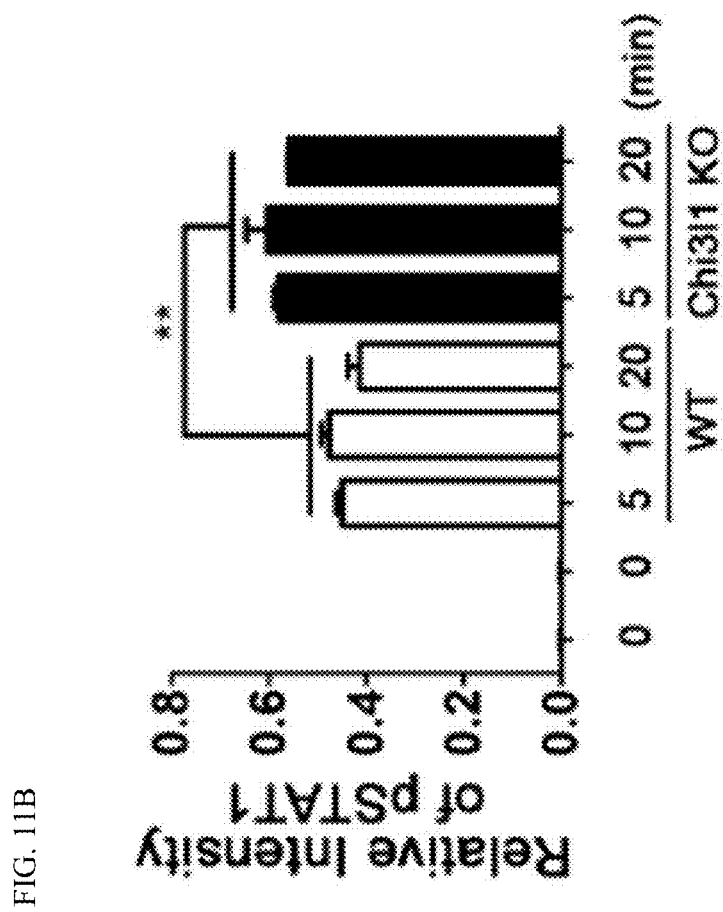
FIG. 11B is a histogram showing the intensities of pSTAT1 relative to β-actin in FIG. 11A. Data are mean±SD of a total of two independent experiments. **p<0.01.

FIG. 11B is a histogram showing the intensities of pSTAT1 relative to β-actin in FIG. 11A. Data are mean±SD of a total of two independent experiments. **p<0.01.

As shown in FIGS. 11A-11B, Chi3l1 KO T cells showed increased pSTAT1 level compared to WT T cells.

Figure 12A:
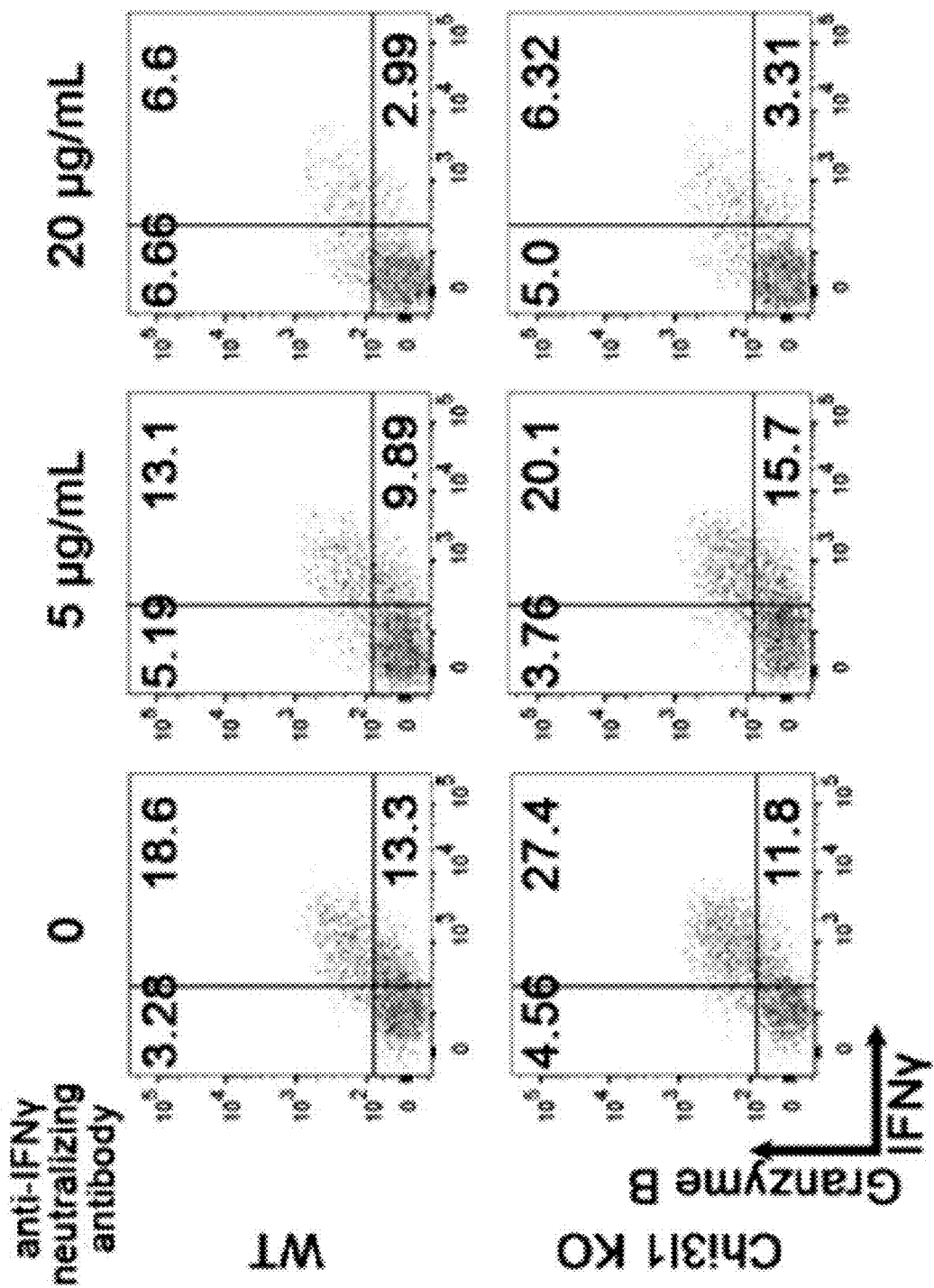
FIG. 12A shows the expression of IFNγ and Granzyme B measured by ICS flow cytometry after WT and Chi3l1 naïve CD8 T cells were sorted by FACS Aria III and activated with plate-bound anti-CD3, anti-CD28, and 11-2 with the indicated concentrations of IFNγ neutralizing antibodies (0, 5, and 20 μg/ml).

FIG. 12A shows the expression of IFN-γ and Granzyme B measured by ICS flow cytometry after WT and Chi3l1 naïve CD8 T cells were sorted by FACS Aria III and activated with plate-bound anti-CD3, anti-CD28, and Il-2 with the indicated concentrations of IFNγ neutralizing antibodies (0, 5, and 20 μg/ml).

Figure 12B:
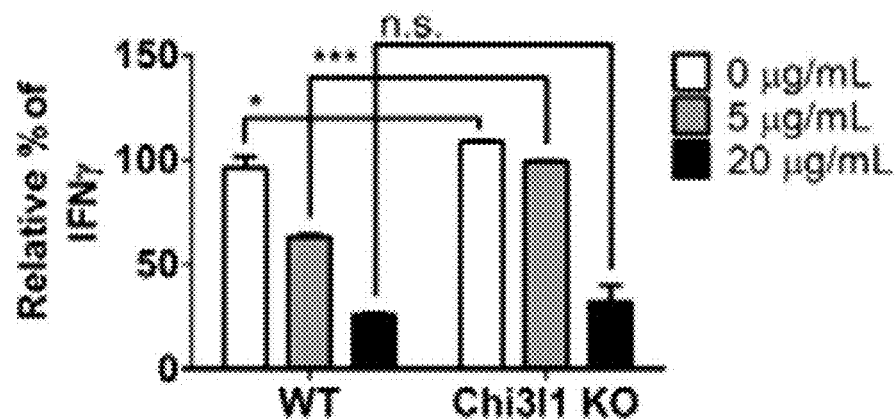
FIGS. 12B and 12C show the relative proportions (%) of (b) IFNγ and (c) Granzyme B in FIG. 12A. Data are mean±SD of a total of three independent experiments. *p<0.05, ***p<0.001.
Figure 12C:
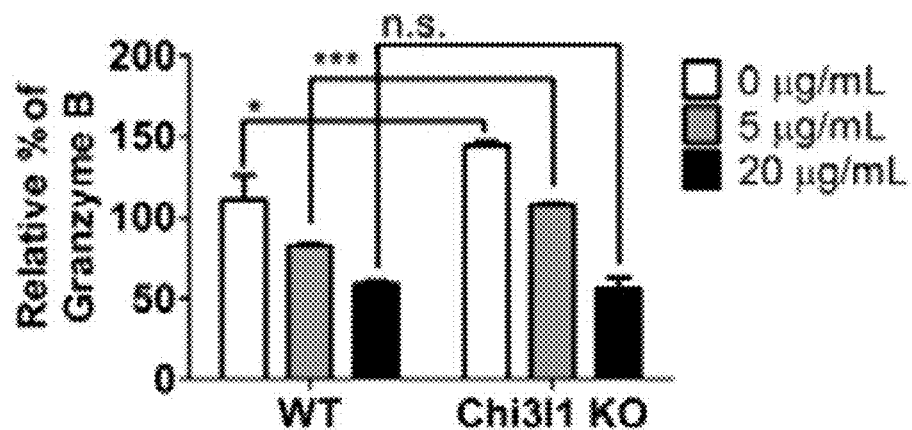

FIGS. 12B and 12C show the relative proportions (%) of (b) IFNγ and (c) Granzyme B in FIG. 12A. Data are mean±SD of a total of three independent experiments. *p<0.05, ***p<0.001.

As shown in FIG. 12, at 20 μg/mL neutralizing antibody, IFNγ-producing cells were equivalent in WT and Chi3l1 KO Th1 cells, suggesting that increased IFNγ production is dependent on IFN-γ signaling. IFNγ dependency in CD8 T cells was confirmed.

IFN-γ and Granzyme B producing activated Chi3l1 KO CD8 T cells were decreased by neutralizing IFNγ antibody treatment, and the level was equivalent with that in WT T cells at 20 μg/mL IFN-γ neutralizing antibody.

Taken together, these results demonstrate that Chi3l1 negatively regulates Th1 differentiation by inhibiting IFNγ-mediated STAT1 phosphorylation.

EXPERIMENTAL EXAMPLE 4

Inhibitory Effect of Chi3l1 on Expression of Th1-Related and Tumoricidal Genes

Figure 13A:
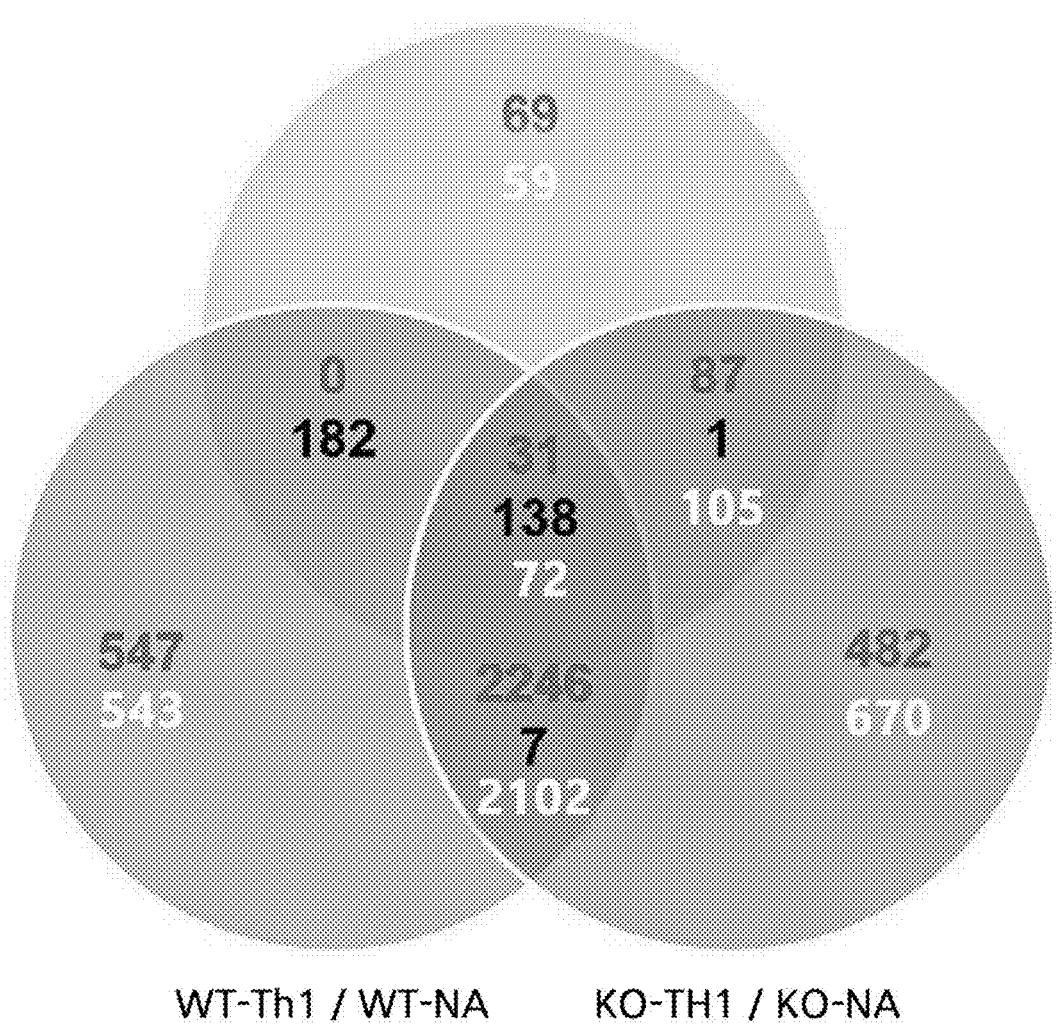
FIG. 13A is a diagram showing a 100-bp RNA-sequencing in naïve cells, Th1-skewed WT CD4 T cells, and Chi3l1 KO CD4 T cells by quantifying up-regulated genes in WT Th1 cells (WT-Th1) and Chi3l1 KO Th1 cells (KO-Th1) and selecting genes of interest from up-regulated genes in WT Th1 versus Chi3l1 KO Th1 comparison.

FIG. 13A is a diagram showing a 100-bp RNA-sequencing in naïve cells, Th1-skewed WT CD4 T cells, and Chi3l1 KO CD4 T cells by quantifying up-regulated genes in WT Th1 cells (WT-Th1) and Chi3l1 KO Th1 cells (KO-Th1) and selecting genes of interest from up-regulated genes in WT Th1 versus Chi3l1 KO Th1 comparison.

Figure 13B:
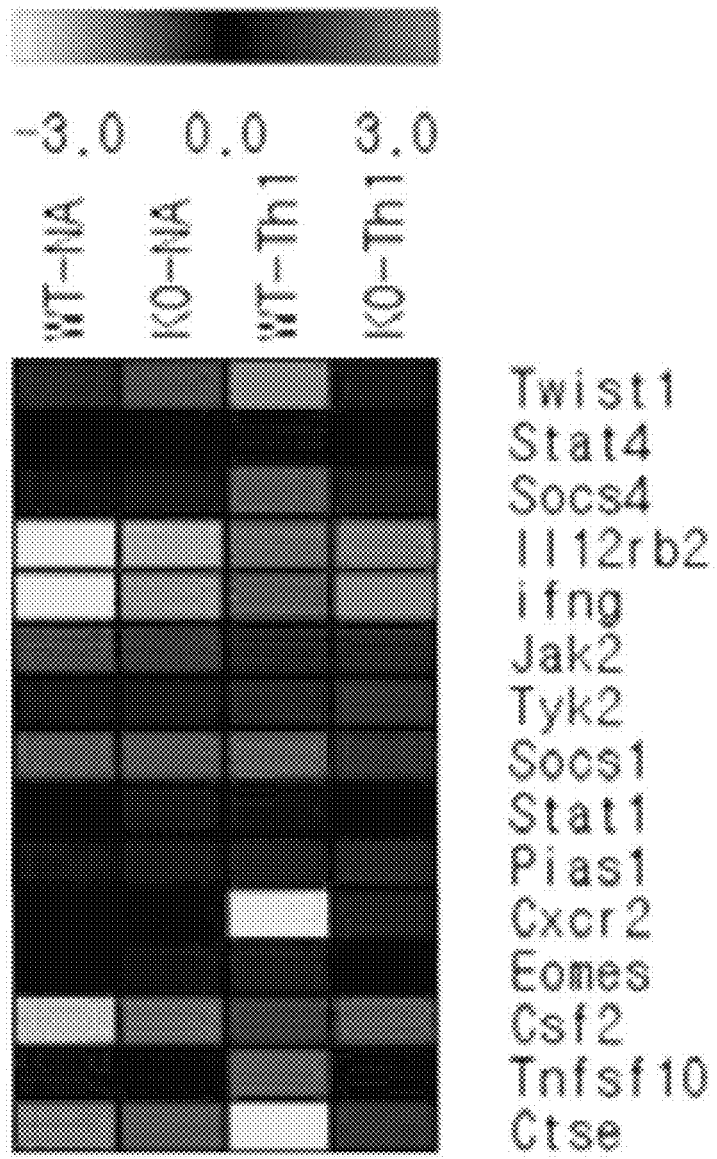
FIG. 13B shows the results of heatmap analysis of up-regulated (red) or down-regulated (blue) genes of interest.
Figure 13C:
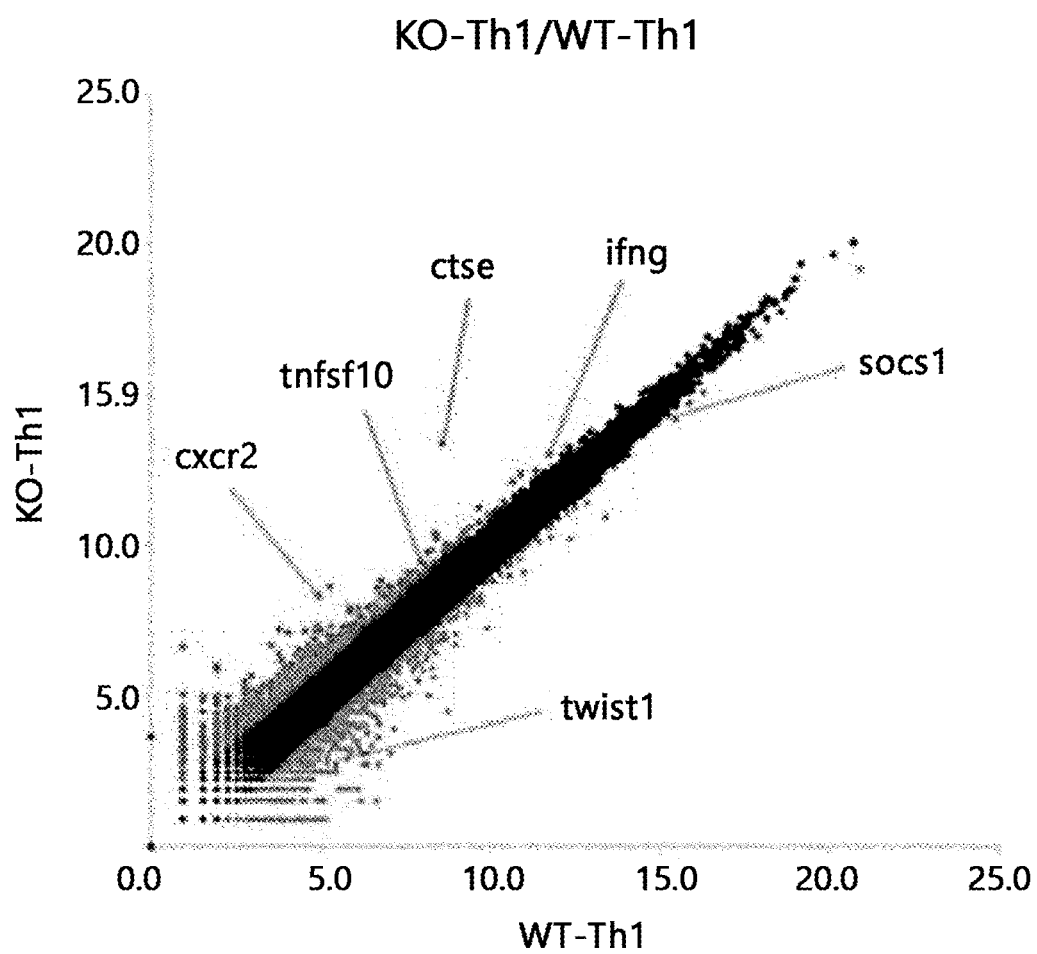
FIG. 13C is a scatterplot showing RNA-sequencing data of at least two-fold down-regulated and up-regulated genes in WT Th1 versus Chi3l1 KO Th1 comparison.

FIG. 13B shows the results of heatmap analysis of up-regulated (red) or down-regulated (blue) genes of interest. FIG. 13C is a scatterplot showing RNA-sequencing data of at least two-fold down-regulated and up-regulated genes in WT Th1 versus Chi3l1 KO Th1 comparison.

Figure 13D:
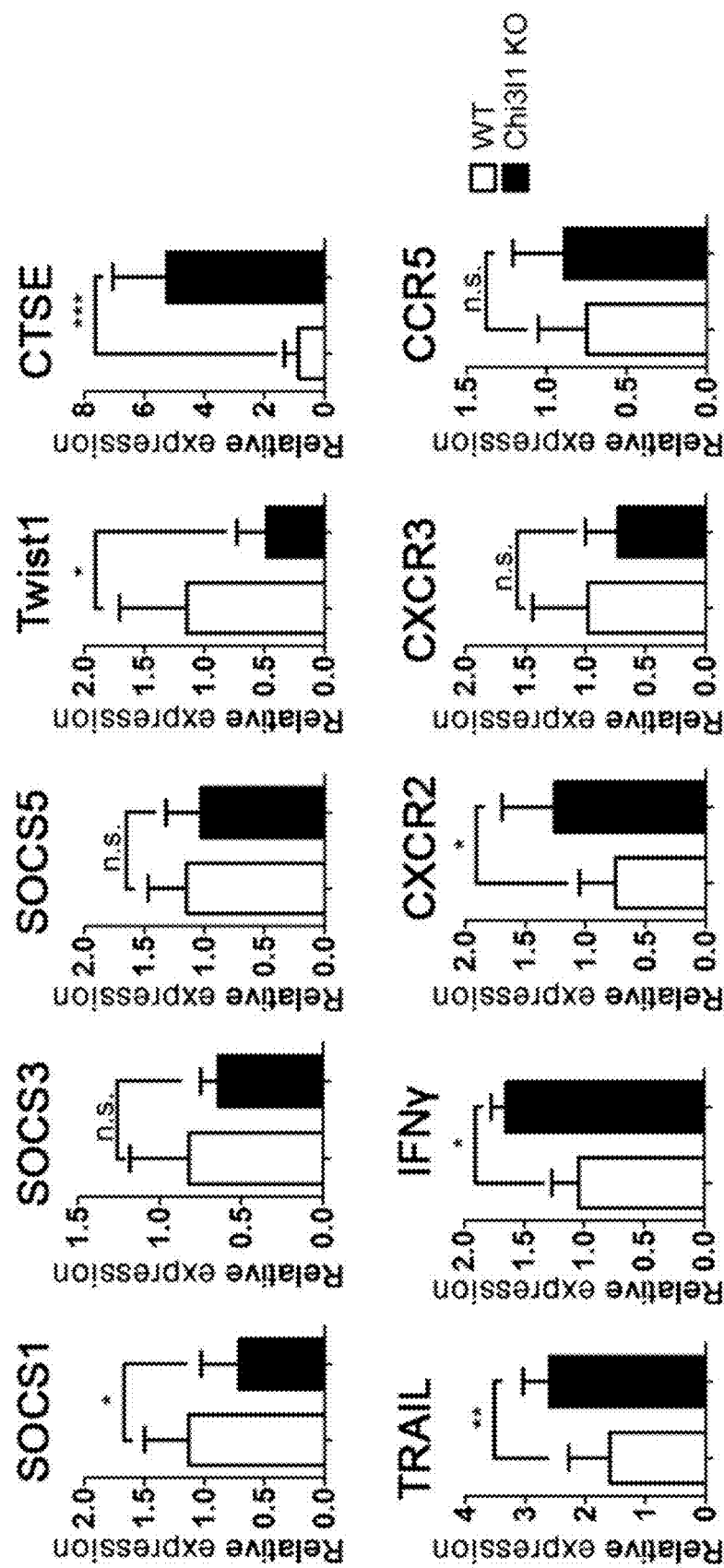
FIG. 13D shows the expression of genes related to the mechanism of IFNγ action and cytotoxicity, which were confirmed by quantitative real-time PCR.
Figure 13E:
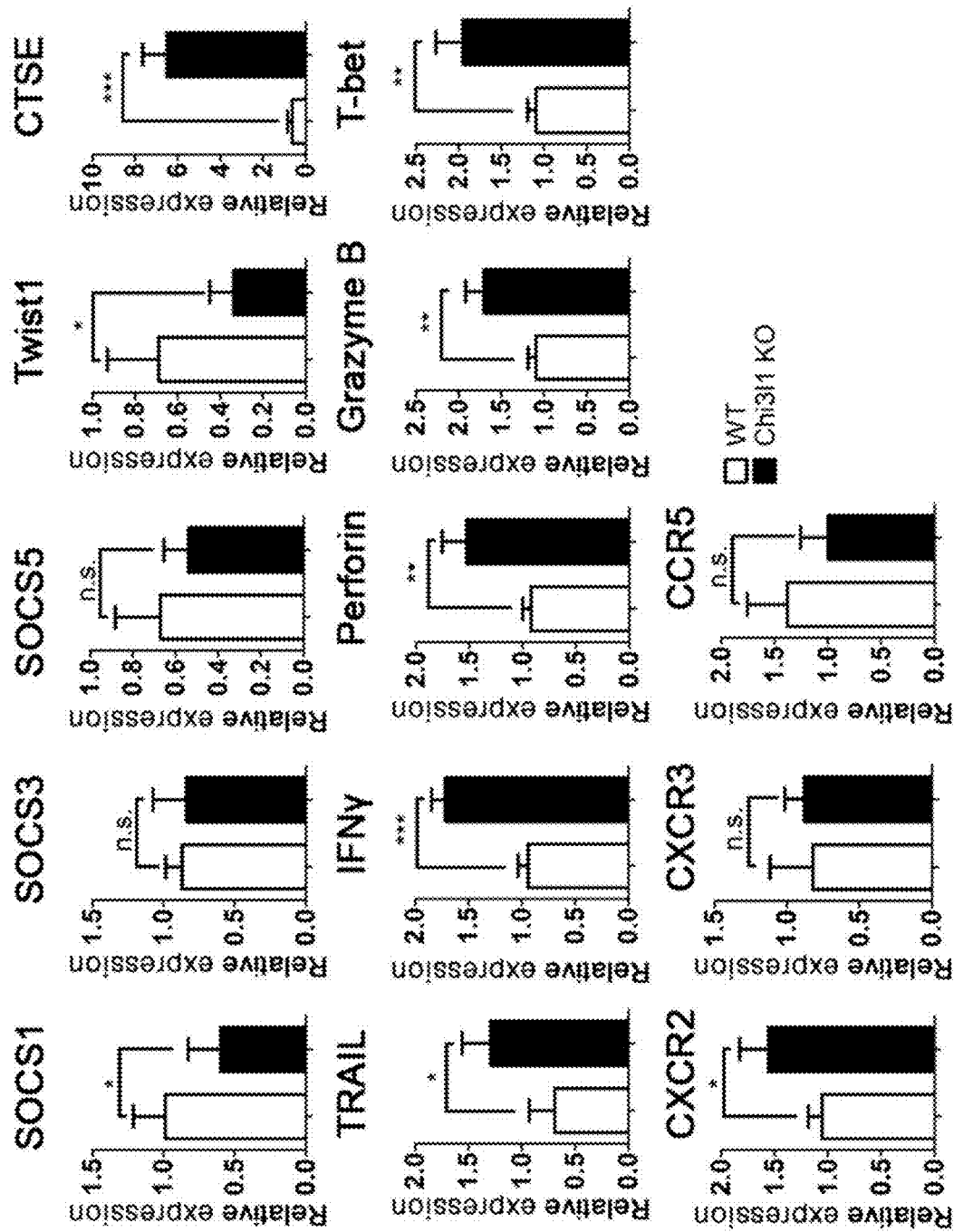
FIG. 13E shows the results of quantitative real-time PCR for genes of interest activating WT and Chi3l1 KO CD8 T cells. The analyte genes were depicted over the corresponding graphs (e.g., SOCS1, SOCS3 . . . CCR5, T-bet). Data are mean±SD of a total of three independent experiments. n.s., not significant; p<0.01, *p<0.001.

FIG. 13D shows the expression of genes related to the mechanism of IFNγ action and cytotoxicity, which were confirmed by quantitative real-time PCR. FIG. 13E shows the results of quantitative real-time PCR for genes of interest activating WT and Chi3l1 KO CD8 T cells. The analyte genes were depicted over the corresponding graphs (e.g., SOCS1, SOCS3 . . . CCR5, T-bet). Data are mean±SD of a total of three independent experiments. n.s., not significant; p<0.01, * p<0.001.

To investigate how Chi3l1 regulates the IFNγ-mediated signaling pathway, RNA was isolated from WT and Chi3l1 KO naïve CD4 T cells and differentiated Th1 cells. The transcriptomes of WT and Chi3l1 KO, naïve, and Th1 cells were analyzed by RNA sequencing.

To determine the differences in gene expression between WT and Chi3l1 KO Th1 cells, genes were classified that were highly expressed in Th1 cells compared with naïve T cells. Genes were also classified that were differently expressed in Chi3l1 KO Th1 cells compared to WT Th1 cells (FIG. 13A). 31 up-regulated genes and 72 down-regulated genes were found in Chi3l1 KO Th1 cells compared to WT Th1 cells.

Twist1 and socs1, which are IFNγ-regulatory genes, were ased, and ifng, ctse, cxcr2, and tnfsfl0 (as known as TRAIL) were increased in Chi3l1 KO Th1 cells (FIG. 13B). A scatterplot summarized these patterns (FIG. 13C).

To confirm the RNA-sequencing results, quantitative real-time PCR analysis of WT and Chi3l1 KO Th1 cells was performed (FIG. 13D). Expression of SOCS1, a phosphatase that inhibits phosphorylation of STAT1, was decreased without significant differences in SOCS3 and SOCSS compared to WT Th1 cells.

Twist1, a Th1 inhibitory molecule, was also reduced, presumably explaining how Chi3l1 KO Th1 cells produce more CTSE, TRAIL, IFNγ, and CXCR2. The molecular expression patterns of FIG. 13E were the same as those of FIG. 13E.

That is, activated Chi3l1 KO CD8 T cells expressed higher levels of T-bet, IFNγ, Perforin, and Granzyme B, suggesting that Chi3l1 KO CD8 T cells induce high levels of effector molecules related to CTL function. Taken together, these results suggest Chi3l1 suppresses Th1-related CTL functions.

EXPERIMENTAL EXAMPLE 5

In Vivo Chi3l1 Effects

An investigation was made as to whether

The increase of effector functional molecules in Chi3l1-deficient T cells prompted an investigation as to whether Chi3l1 KO Th1 cells and CTL contributed to anti-tumor immunity. To this end, B16F10 melanoma lung metastasis model was used. The melanoma lung metastasis model was the same as that used in Experimental Method 8) and the analysis was also performed with reference to the experimental method.

Figure 14A:
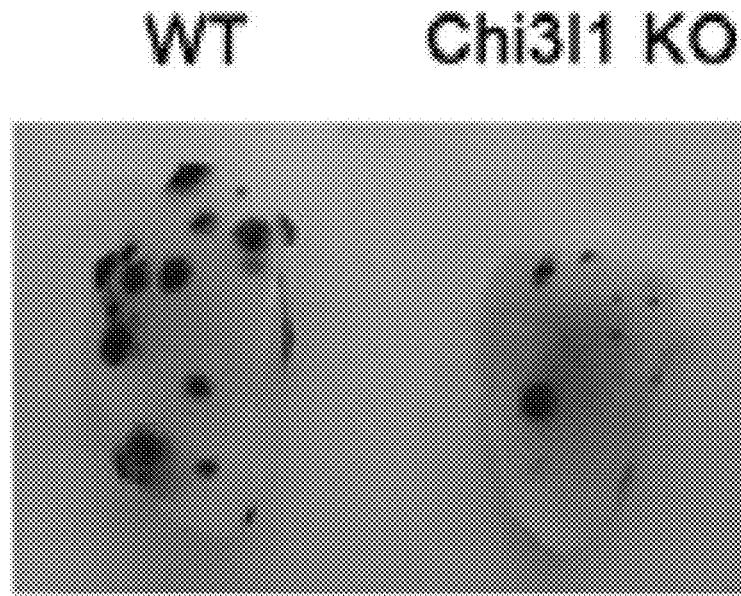
FIG. 14A is an image from WT and Chi3l1 KO models 2 weeks after IV injection with $5 \times 10^5$ B16F10 melanoma cells.

FIG. 14A is an image from WT and Chi3l1 KO models 2 weeks after IV injection with 5×10$^5$ B16F10 melanoma cells. Specifically, the image shows the lungs excised from the WT and Chi3l1 KO models injected with melanoma cells. At 14 days, metastatic melanoma colonies were observed on the lung surface. Less melanoma metastasis occurred in the Chi3l1 KO model than in the WT model.

Figure 14B:
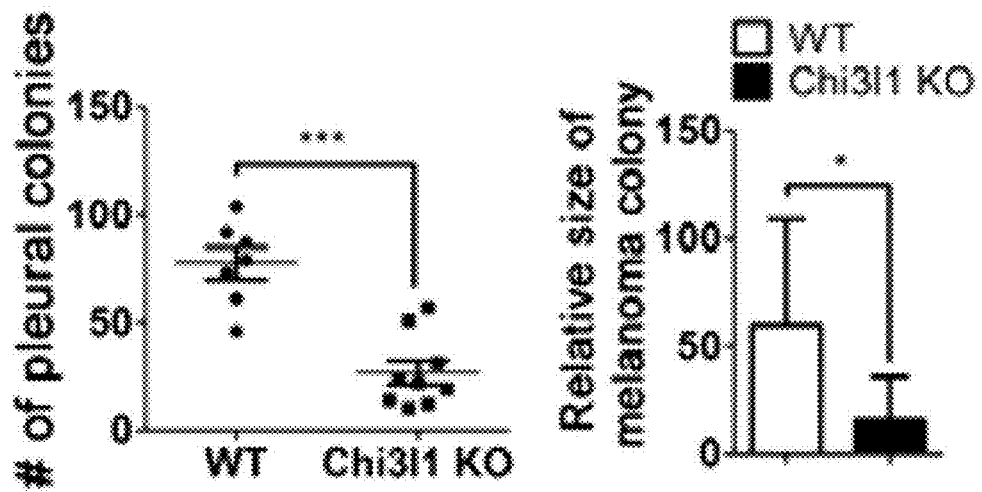
FIG. 14B shows the relative sizes and numbers of pleural colonies in the lungs of WT and Chi3l1 KO models injected with $5 \times 10^5$ B16F10 melanoma cells.

FIG. 14B shows the relative sizes and numbers of pleural colonies in the lungs of WT and Chi3l1 KO models injected with 5×10$^5$ B16F10 melanoma cells. Melanoma lung metastasis was significantly reduced in the Chi3l1 KO model compared to the WT model.

Figure 14C:
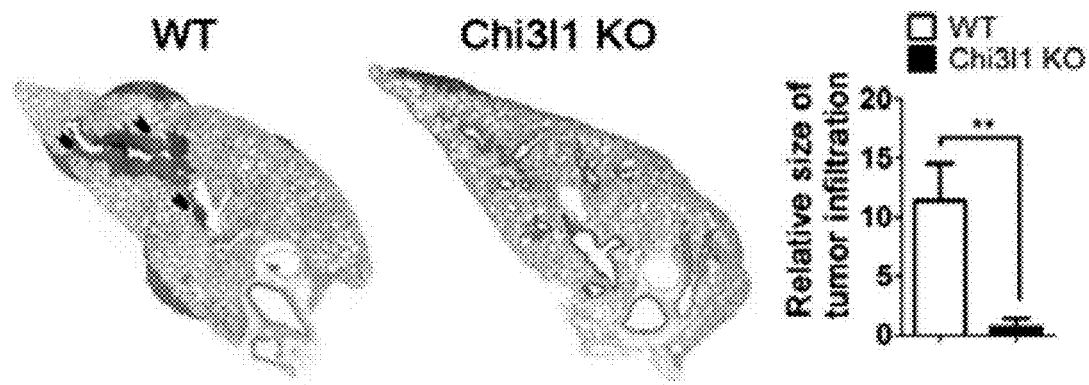
FIG. 14C shows histological images of H&E stained lung tissues resected from WT and Chi3l1 KO models injected with $5 \times 10^5$ B16F10 melanoma cells.

FIG. 14C shows histological images of H&E stained lung tissues resected from WT and Chi3l1 KO models injected with 5×10$^5$ B16F10 melanoma cells. In both models, the relative sizes of infiltrated tumors were measured and are shown in the right graph. Infiltrated tumors around blood vessels were significantly decreased in the Chi3l1 KO model compared to the WT model.

FIGS. 14D to 14G show the results of flow cytometry for lymphocytes obtained from the lungs of WT and Chi3l1 KO models injected with 5×10$^5$ B16F10 melanoma cells by Percoll and graphically show IFNγ, Foxp3, and Granzyme B in CD4 T cells, CD8 T cells, NK cells, and non-lymphocytic population, which was analyzed by intracellular cytokine staining. The genes and models are depicted in the corresponding graphs. Representative percentages of FNγ+, Foxp3+, and MFI of Granzyme B+ are described in FIGS. 14E to 14G.

Figure 14D:
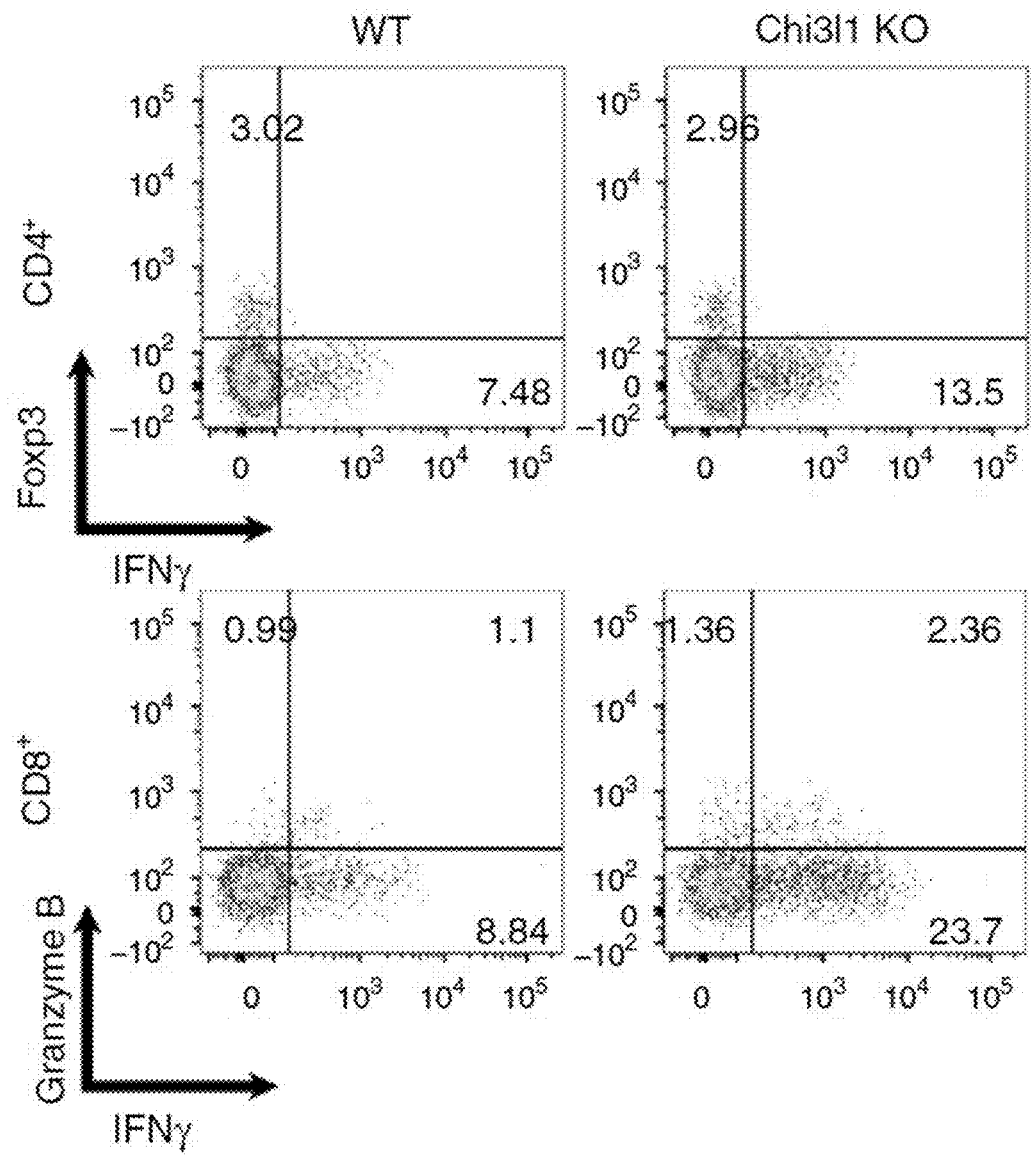
FIGS. 14D to 14G show the results of flow cytometry for lymphocytes obtained from the lungs of WT and Chi3l1 KO models injected with $5 \times 10^5$ B16F10 melanoma cells by Percoll and graphically show IFNγ, Foxp3, and Granzyme B in CD4 T cells, CD8 T cells, NK cells, and non-lymphocytic population, which was analyzed by intracellular cytokine staining. The genes and models are depicted in the corresponding graphs. Representative percentages of FNγ$^+$, Foxp3$^+$, and MFI of Granzyme B$^+$are described in FIGS. 14E to 14G.
Figure 14E:
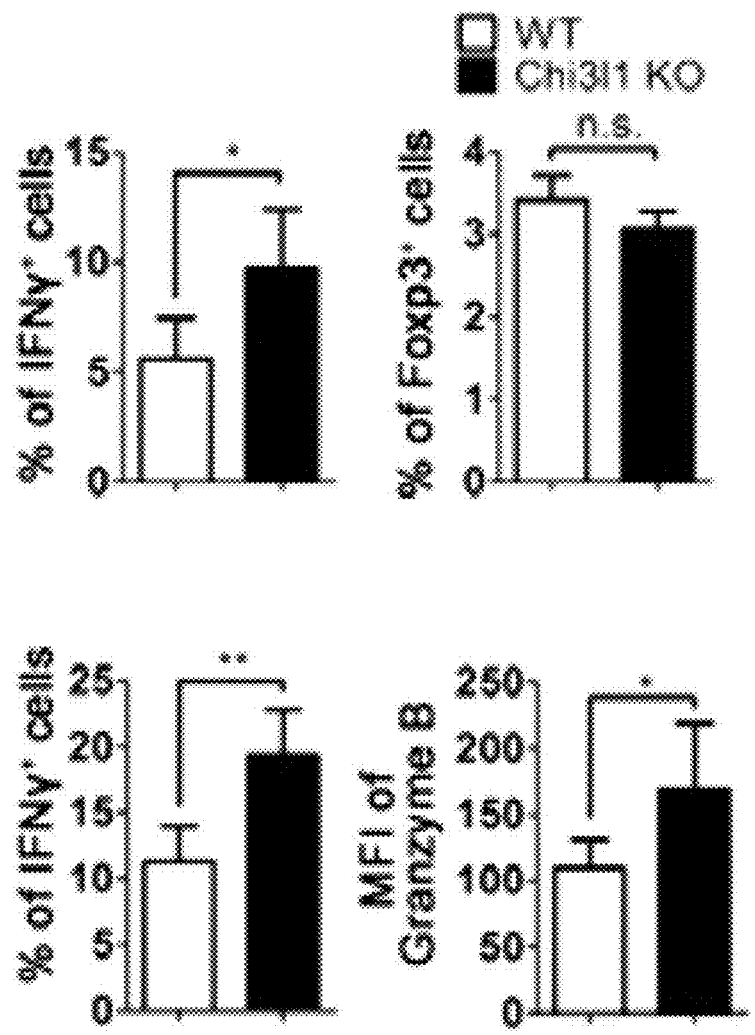
Figure 14F:
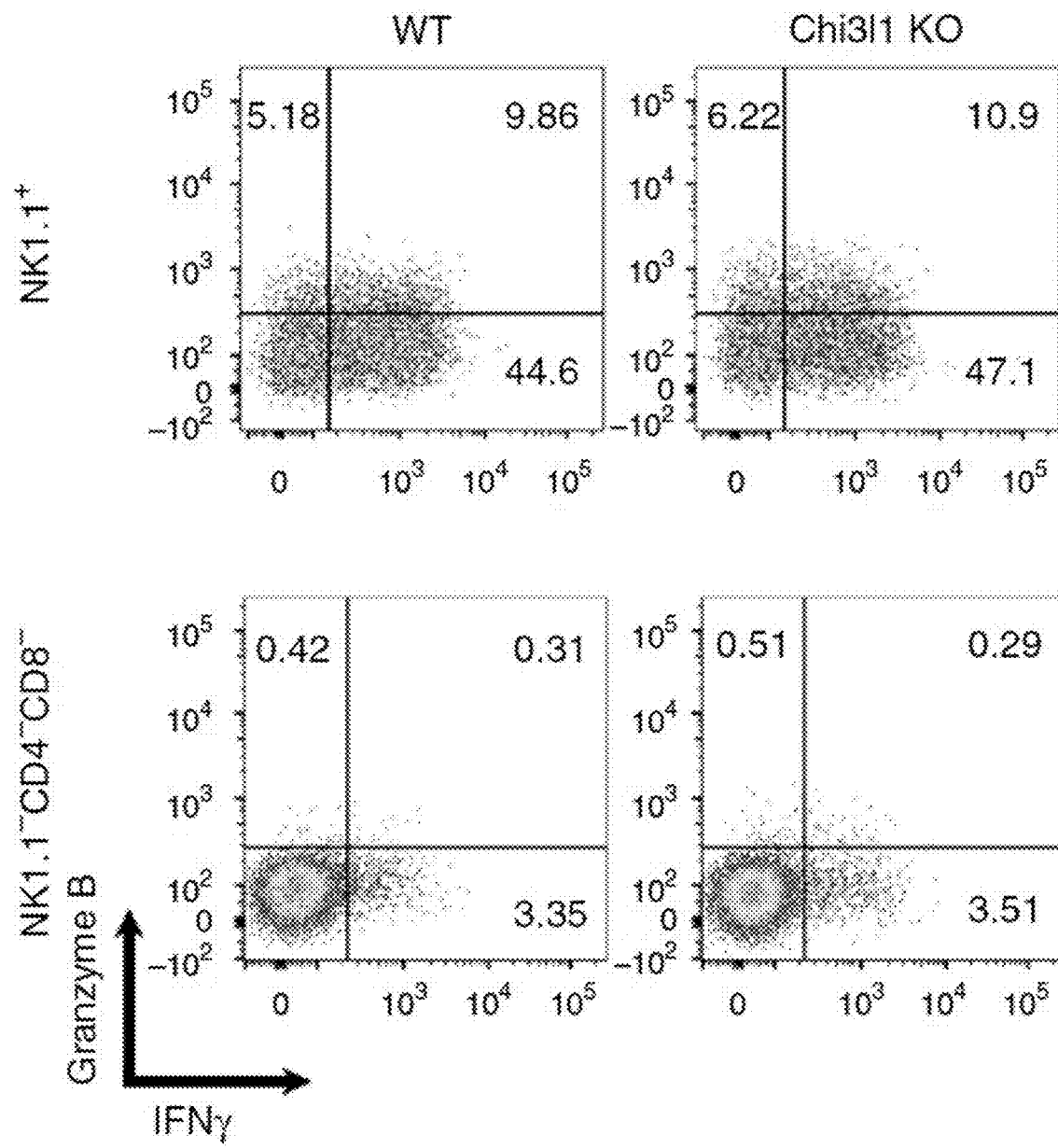
Figure 14G:
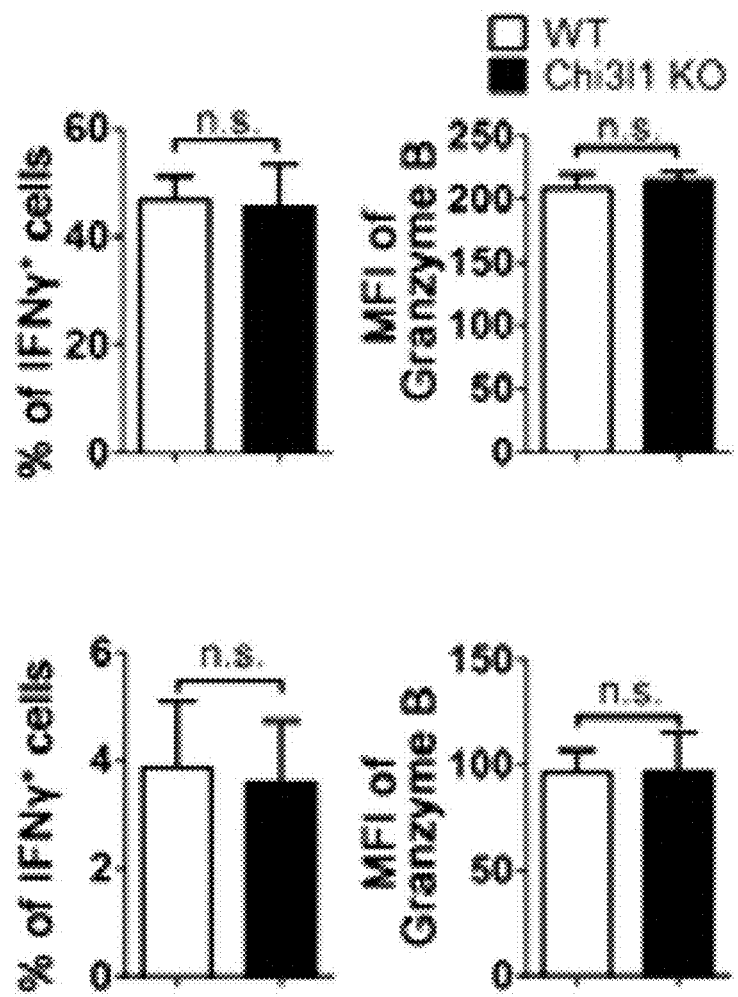

As shown in FIGS. 14Dd and 14E, increased infiltration of IFNγ-producing CD4 T cells and CD8 T cells was significantly higher in the lungs of the Chi3l1 KO model than the WT model. This indicates that Chi3l1 deficiency increased the numbers of CD4 T cells and CD8 T cells, leading to a significant increase in IFNγ production. As shown in FIGS. 14F and 14G, no difference was observed in the IFNγ-producing properties of NK cells and non-lymphocytic population in both models injected with melanoma cells.

Figure 14H:
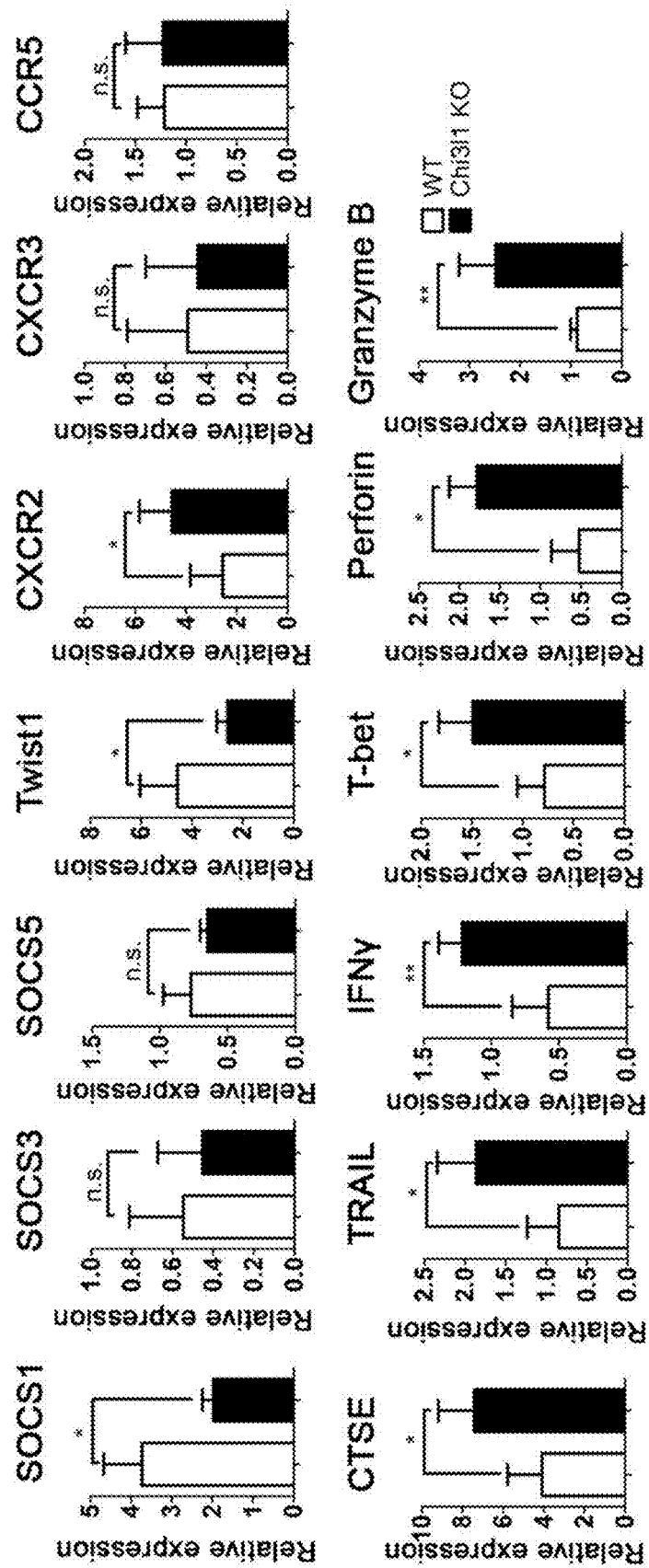
FIG. 14H shows the expression of genes in lymphocytes isolated from WT and Chi3l1 KO models injected with $5 \times 10^5$ B16F10 melanoma cells.

FIG. 14H shows the expression of genes in lymphocytes isolated from WT and Chi3l1 KO models injected with $5\times10^5$ B16F10 melanoma cells. The Chi3l1 KO model injected with melanoma cells had increased mRNA for anti-tumor immunity molecules including CTSE, TRAL, IFNγ, T-bet, Perforin, and Granzyme B, while the expression of Th1-inhibitory molecules Twist1 and SOCS1 was significantly reduced.

Figure 14I:
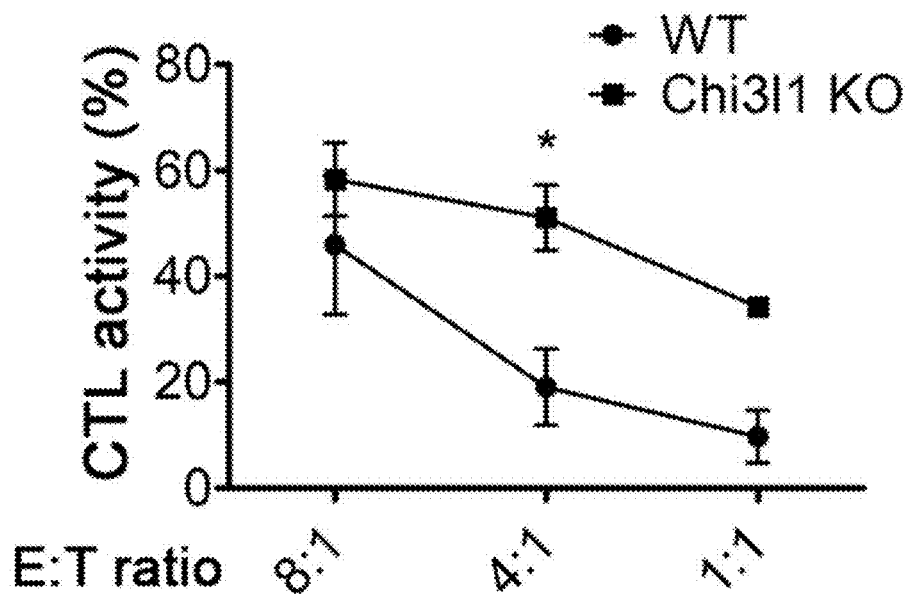
FIG. 14I shows the cytotoxicity of WT and Chi3l1 KO CD8 T cells against B16F10 target cells at indicated E:T ratios.
Figure 14J:
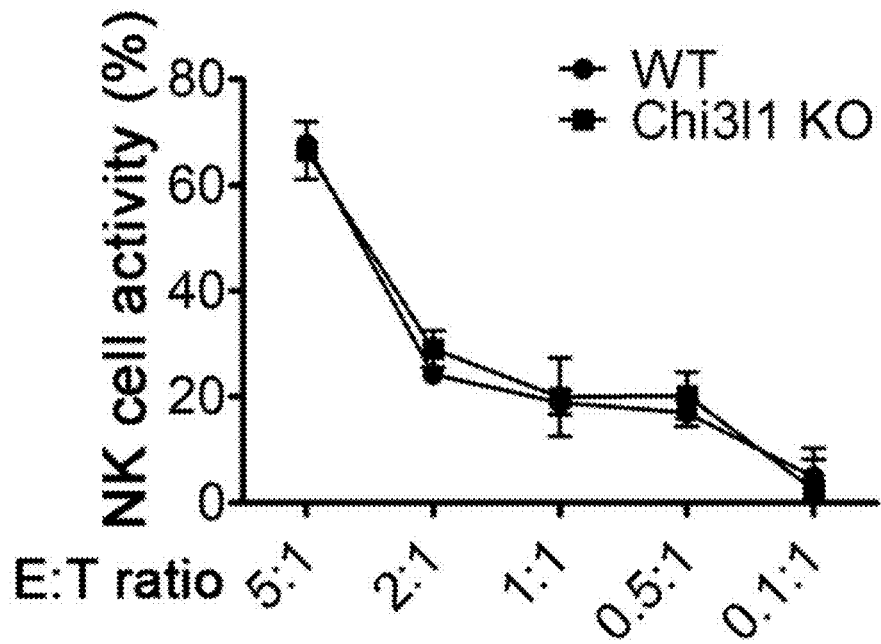
FIG. 14J shows the cytotoxicity of WT CD8 T cells, Chi3l1 KO CD8 T cells and NK cells.

FIG. 14I shows the cytotoxicity of WT and Chi3l1 KO CD8 T cells against B16F10 target cells at indicated E:T ratios and FIG. 14J shows the cytotoxicity of WT CD8 T cells, Chi3l1 KO CD8 T cells and NK cells.

As shown in FIGS. 14I and 14J, pre-activated WT or Chi3l1 KO CD8 T cells and B16F10 melanoma cells were co-cultured to confirm the increased tumoricidal activity in Chi3l1 KO CD8 T cells. Chi3l1 KO CD8 T cells showed more potent tumor-killing activity than WT CD8 T cells.

However, no significant difference in the cytotoxicity of WT and Chi3l1 KO NK cells was observed. Collectively, these results suggest that Chi3l1 is a negative regulator of Th1 and CTL responses.

EXPERIMENTAL EXAMPLE 6

Regulatory Effect of Therapeutic siRNA Complex Using dNP2 Peptide and siChi3l1 on Th1 and CTL The present inventors propose a novel siChi3l1 complex with a cell-penetrating peptide (CPP), dNP2, which delivers an immune regulatory protein into T cells, and intended to confirm whether this complex has an inhibitory effect on pulmonary metastasis of cancer.

The present inventors devised a novel strategy to use a complex of dNP2 peptide (SEQ ID NO: 2) and siChi3l1 (SEQ ID NO: 1) as a siRNA inhibiting the activity of Chi3l1 to induce anti-tumor immunity.

Figure 15A:
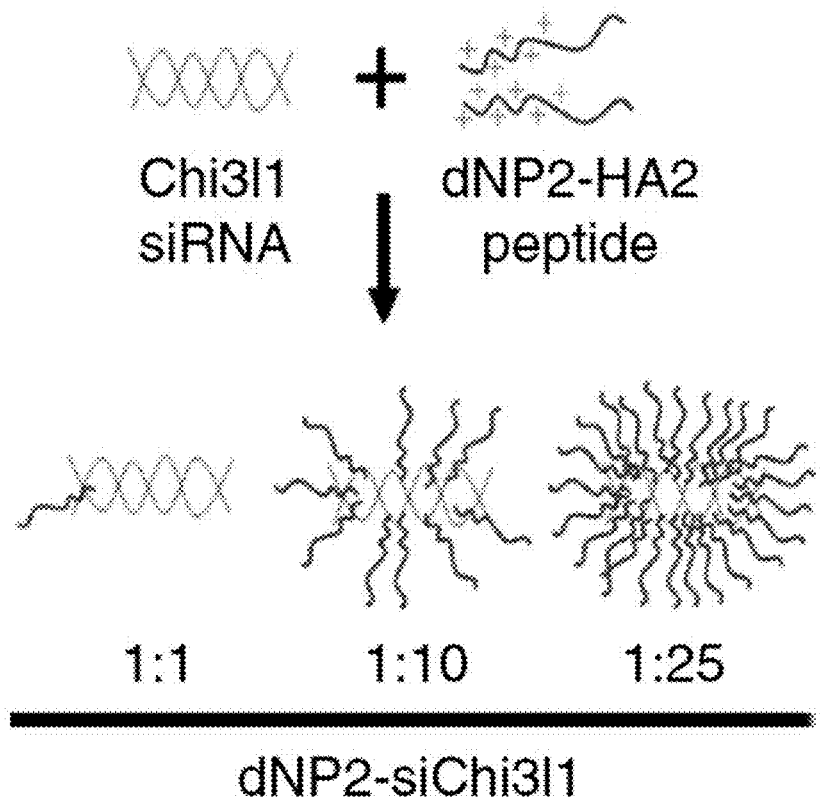
FIG. 15A is a diagram showing the structures of dNP2-siChi3l1 complexes of dNP2-HA2 peptide and Chi3l1 siRNA.

Specifically, dNP2-HA2 peptide was synthesized and siChi3l1 was mixed and fused with the dNP2-HA2 peptide in ratios of 1:1, 1:10, and 1:25 to prepare complexes, which are referred to as dNP2-siChi3l1 1:1, 1:10, and 1:25, respectively. FIG. 15A is a diagram showing the structures of dNP2-siChi3l1 complexes of dNP2-HA2 peptide and Chi3l1 siRNA.

Hereinafter, the intracellular delivery of the dNP2-siChi3l1 complexes was confirmed and their inhibitory activity on pulmonary metastasis of cancer was analyzed. To this end, an in vivo experiment was conducted to determine whether the complexes effectively reduces Chi3l1 and an in vitro experiment was conducted to determine whether the complexes improves Th1 differentiation and CD8 T cell differentiation.

Figure 15B:
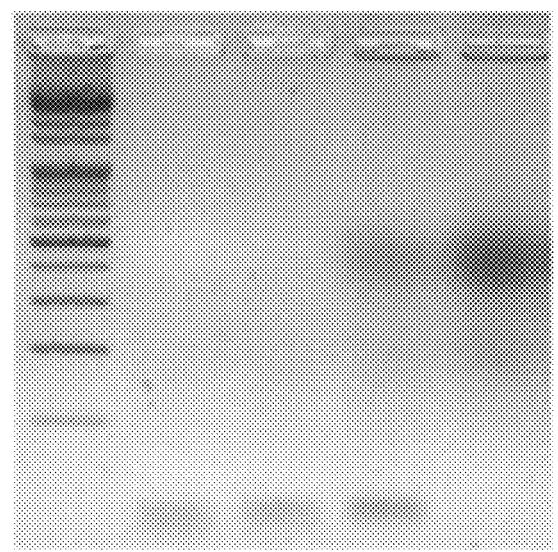
FIG. 15B shows the results of gel retardation assay for dNP2-siChi3l1 complexes at the indicated N/P ratios.

FIG. 15B shows the results of gel retardation assay for dNP2-siChi3l1 complexes at the indicated N/P ratios. In the dNP2-siChi3l1 complex (1:10), the dNP2-HA2 peptide was successfully conjugated with siChi3l1 through noncovalent interaction.

Figure 15C:
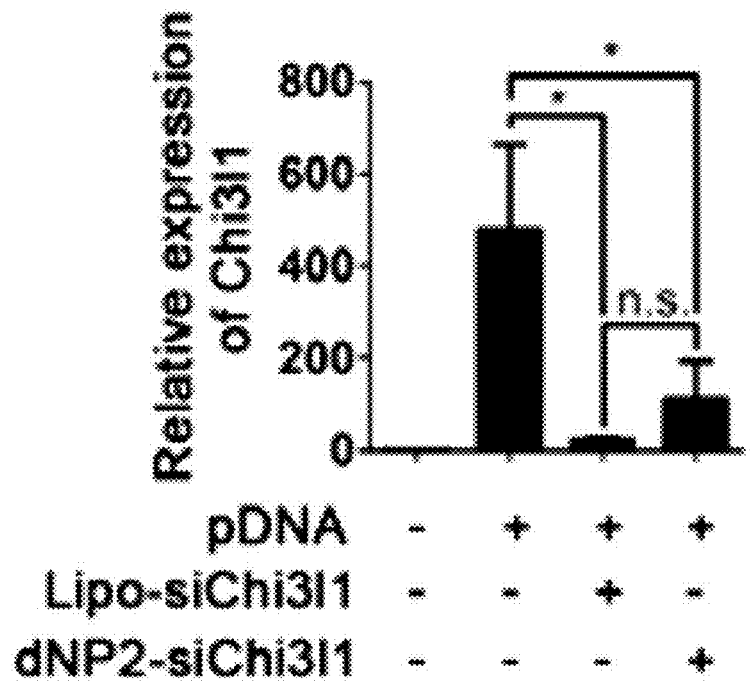
FIG. 15C shows the expression levels of Chi3l1 mRNA from HEK293 T cells treated with Chi3l1 siRNA by lipofectamine and with dNP2-siChi3l1 complex (dNP2-siChi3l1).
Figure 15D:
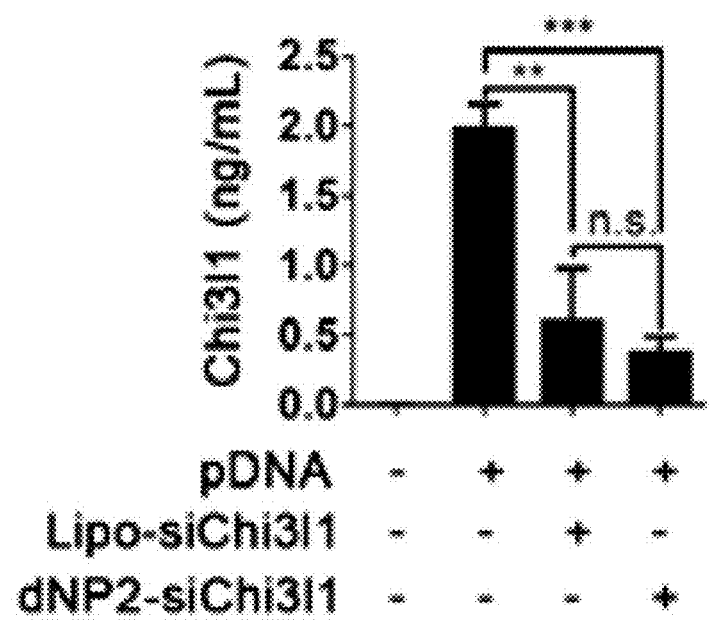
FIG. 15D shows the relative expression levels of Chi3l1 analyzed from FIG. 15C analyzed by ELISA. Chi3l1 was overexpressed in the HEK293T cells through pDNA (pDNA+: negative control). HEK293T cells untreated with pDNA (pDNA−) was used as a positive control.

FIG. 15C shows the expression levels of Chi3l1 mRNA from HEK293 T cells treated with Chi3l1 siRNA by lipofectamine and with dNP2-siChi3l1 complex (dNP2-siChi3l1). FIG. 15D shows the relative expression levels of Chi3l1 analyzed from FIG. 15C by ELISA. Chi3l1 was overexpressed in the HEK293T cells through pDNA (pDNA+: negative control). HEK293T cells untreated with pDNA (pDNA−) was used as a positive control.

To confirm the knockdown efficiency of the dNP2-siChi3l1 complexes, Chi3l1-overexpressed HEK293T cells were used. The knockdown efficiency of dNP2-siChi3l1 complex or Lipo-siChi3l1 delivery was compared at the Chi3l1 mRNA (FIG. 15C) and Chi3l1 protein levels (FIG. 15D). dNP2-siChi3l1 complex significantly suppressed Chi3l1 expression and the level of suppression was comparable to the positive control.

Figure 15E:
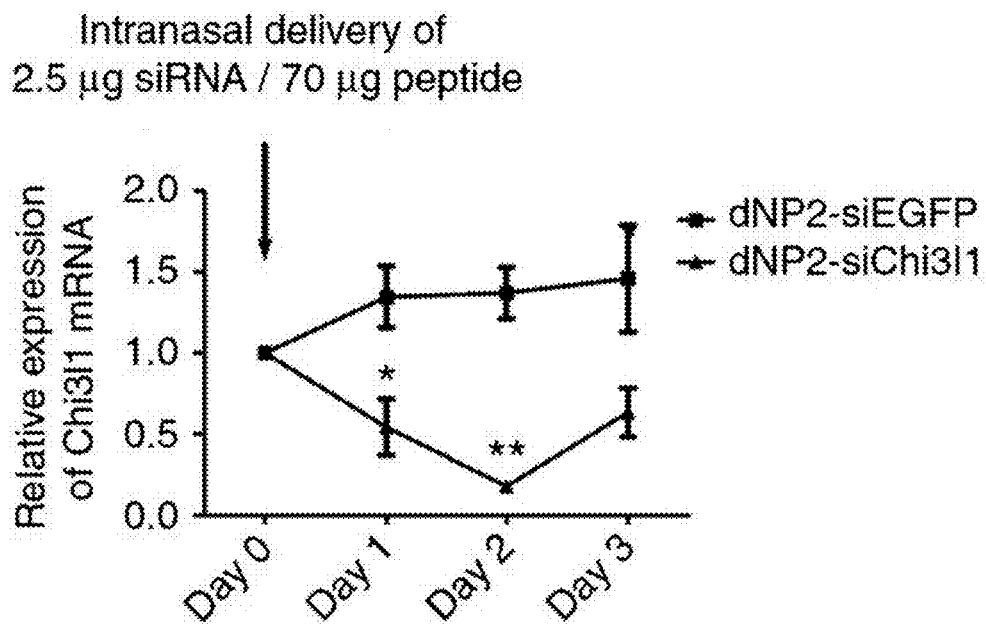
FIG. 15E shows the expression levels of Chi3l1 mRNA in the lung after pulmonary melanoma metastasis animal model was treated intranasally with dNP2-siEGFP or dNP2-siChi3l1. The relative Chi3l1 mRNA expression levels were measured at different days and presented as relative to expression at day 0.

FIG. 15E shows the expression levels of Chi3l1 mRNA in the lung after pulmonary melanoma metastasis animal model was treated intranasally with dNP2-siEGFP or dNP2-siChi3l1. The relative Chi3l1 mRNA expression levels were measured at different days and presented as relative to expression at day 0.

Figure 15F:
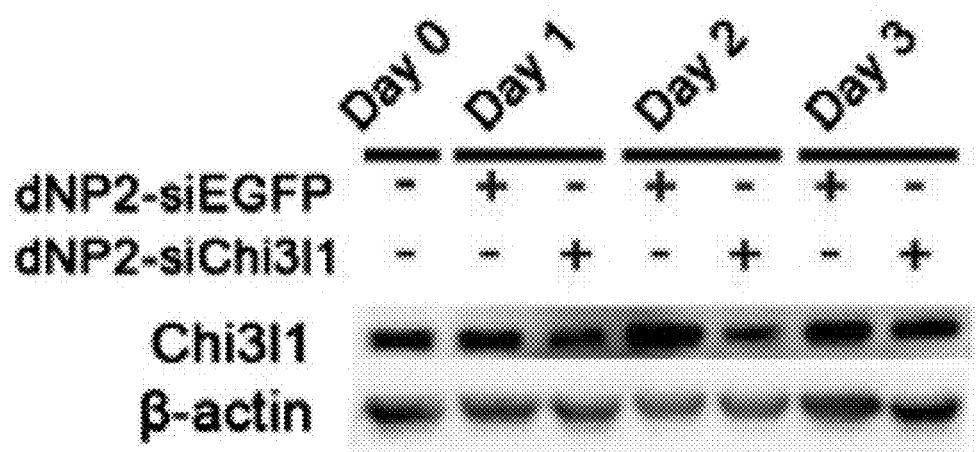
FIG. 15F shows Chi3l1 protein expression levels in the lung, which were analyzed by Western blotting after pulmonary melanoma metastasis animal model was treated intranasally with dNP2-siEGFP or dNP2-siChi3l1.
Figure 15G:
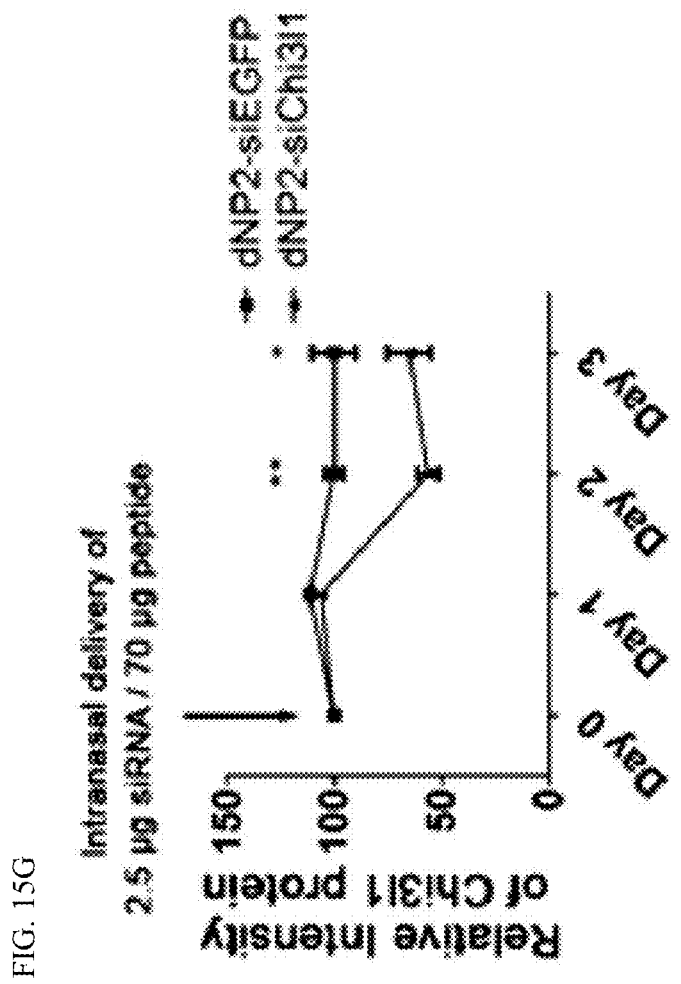
FIG. 15G shows Chi3l1 protein expression levels relative to β-actin, which were calculated by densitometric analysis of the results of FIG. 15F. The Chi3l1 band intensities were quantified relative to the band intensity of β-actin.

Specifically, first, the dNP2-siEGFP or dNP2-siChi3l1 siRNA complex was intranasally administered to pulmonary melanoma metastasis animal model. After the animals were sacrificed, in vivo Chi3l1 knockdown efficiency was evaluated by RT-PCR daily for 3 days. The results are shown in FIGS. 15F and 15G. the dNP2-siChi3l1 complex prepared by mixing 70 µg of dNP2-HA2 peptide with 2.5 µg of siChi3l1 (1:25 N/P ratio) showed significant reduction of Chi3l1 mRNA expression in the lung at day 1. Maximum silencing of Chi3l1 expression was noted at day 2 and the level of Chi3l1 started to restore from day 3.

FIG. 15F shows Chi3l1 protein expression levels in the lung, which were analyzed by Western blotting after pulmonary melanoma metastasis animal model was treated intranasally with dNP2-siEGFP or dNP2-siChi3l1. FIG. 15G shows Chi3l1 protein expression levels relative to β-actin, which were calculated by densitometric analysis of the results of FIG. 15F. Chi3l1 band intensity was quantified relative to that of β-actin.

As shown in FIGS. 15F and 15G, Chi3l1 expression level was significantly reduced until day 2 after treatment with dNP2-siChi3l1 complex and started to restore from day 3.

Figure 15H:
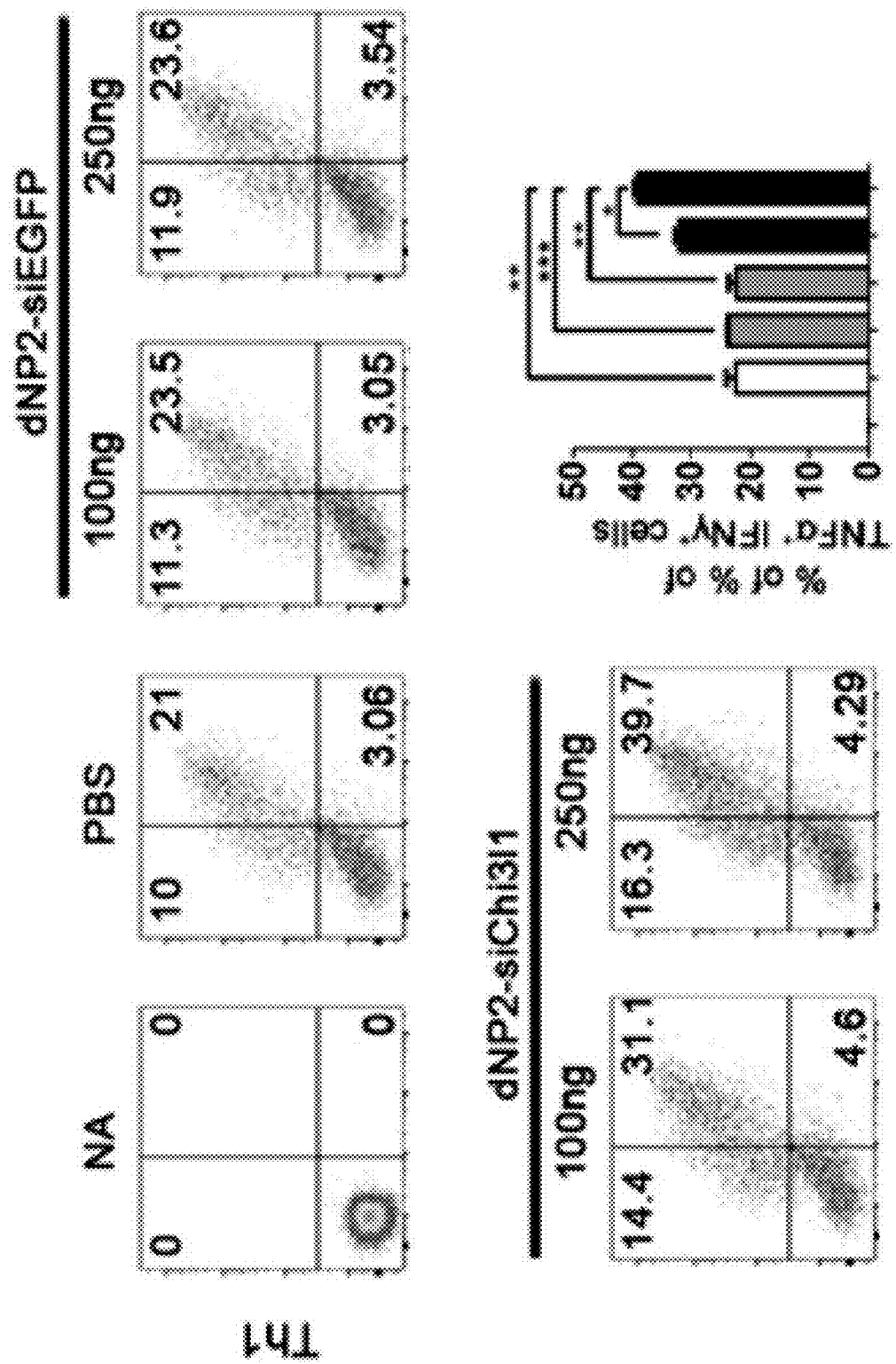
FIG. 15H shows the differentiation of WT naïve CD4 T cells into Th1 cells after treatment with dNP2-siEGFP or dNP2-siChi3l1 at various concentrations (100 ng, 250 ng) and culture for 5 days (left) and IFNγ and TNFα expression levels analyzed by flow cytometry (right). Data are mean±SD of at least three independent experiments. *p<0.05, p <0.01, *p<0.001.

Next, the functional activity of dNP2-siChi3l1 in Th1 differentiation was determined. FIG. 15H shows the differentiation of WT naïve CD4 T cells into Th1 cells after treatment with dNP2-siEGFP or dNP2-siChi3l1 at various concentrations (100 ng, 250 ng) and culture for 5 days (left) and IFNγ and TNFα expression levels analyzed by flow cytometry (right). Data are mean±SD of at least three independent experiments. *p<0.05, p<0.01, * p<0.001.

As shown in FIG. 15H, 5 days after treatment with dNP2-siEGFP or dNP2-siChi3l1 complex, FACS-sorted WT naïve CD4 T cells were differentiated into Th1 cells. IFN-γ- and TNFα-producing cells were analyzed by flow cytometry. From 100 ng to 250 ng, dNP2-siChi3l1 complex resulted in significantly increased IFNγ-producing and TNFα-producing cells compared to a dNP2-siEGFP-treated group, indicating siRNA targeting Chi3l1 could be delivered into T cells and strengthened Th1 differentiation.

Figure 15I:
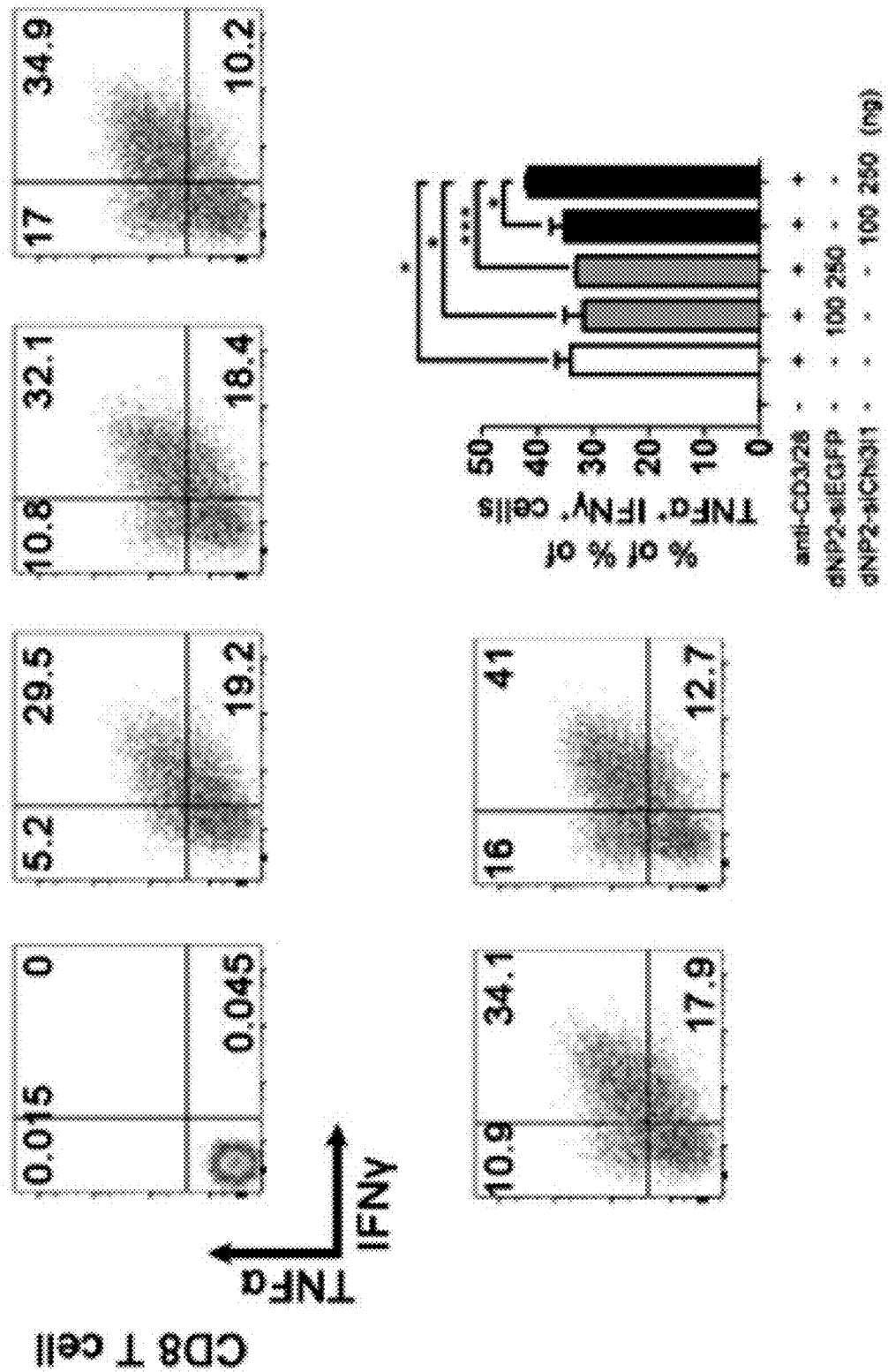
FIG. 15I shows the differentiation of WT naïve CD8 T cells into CD8 T cells after activation with anti-CD3, anti-CD28, and IL-2, treatment with dNP2-siEGFP or dNP2-siChi3l1 at various concentrations (100 ng, 250 ng), and culture for 3 days (left) and IFNγ and TNFα expression levels analyzed by flow cytometry (right). Data are mean±SD of at least three independent experiments. *p<0.05, p<0.01, *p<0.001.

FIG. 15I shows the differentiation of WT naïve CD8 T cells into CD8 T cells after activation with anti-CD3, anti-CD28, and IL-2, treatment with dNP2-siEGFP or dNP2-siChi3l1 at various concentrations (100 ng, 250 ng), and culture for 3 days (left) and IFNγ and TNFα expression levels analyzed by flow cytometry (right). Data are mean±SD of at least three independent experiments. *p<0.05, p<0.01, * p<0.001.

As shown in FIG. 15I, more activated CD8 T cells having the ability to produce IFNγ and TNFα were observed in the group treated with dNP2-siChi3l1. From this observation, it was confirmed that dNP2 peptide was successfully fused with siChi3l1 to form the complex, the complex enabled effective in vivo and in vitro siChi3l1 delivery, the pulmonary Chi3l1 gene was knock-downed, and Th1 and CTL functions were improved.

Therefore, it was confirmed that the dNP2-siChi3l1 complex suppressed the expression of the Chi3l1 gene to improve Th1 and CTL functions, demonstrating its prophylactic or inhibitory effects on pulmonary metastasis of cancer, like when siChi3l1 was used alone.

However, siChi3l1 can be intranasally administered to lung tissue for its expression when the dNP2-siChi3l1 complex is used, unlike when siChi3l1 was used alone. As a result, the prophylactic or inhibitory effects of the dNP2-siChi3l1 complex on cancer metastasis are markedly improved even when used in a small amount. That is, the use of the dNP2-siChi3l1 complex is noticeably effective and advantageous over the single use of siChi3l1 in that siRNA can be directly administered via an intranasal route to achieve prophylactic or inhibitory effects on cancer metastasis.

EXPERIMENTAL EXAMPLE 7

Inhibitory Effect of Intranasal Administration of dNP2-Chi3l1 Complex on Pulmonary Metastasis of Cancer Here, the in vivo efficiency of dNP2-siChi3l1 in the regulation of melanoma lung metastasis was investigated.

First, $5 \times 10^5$ B16F10 melanoma cells were injected into WT mice to prepare pulmonary melanoma metastasis animal model. Specifically, the melanoma lung metastasis model was prepared with reference to Experimental Method 8). 14 days after injection, mice were sacrificed. A determination was made as to whether cancer effectively metastasized to the lung surface.

Next, a complex prepared by mixing 2.5 μg of siEGFP and 70 μg of dNP2-HA peptide was administered intranasally to a control group. A complex prepared by mixing 2.5 μg of siChi3l1 and 70 μg of dNP2-HA peptide was administered intranasally to an experimental group. The complex was injected twice daily from day 0 to day 12 and the lung metastasis was analyzed at day 14. Each of the complexes was administered in equal amounts twice per day from day 0 to day 14.

Figure 16A:
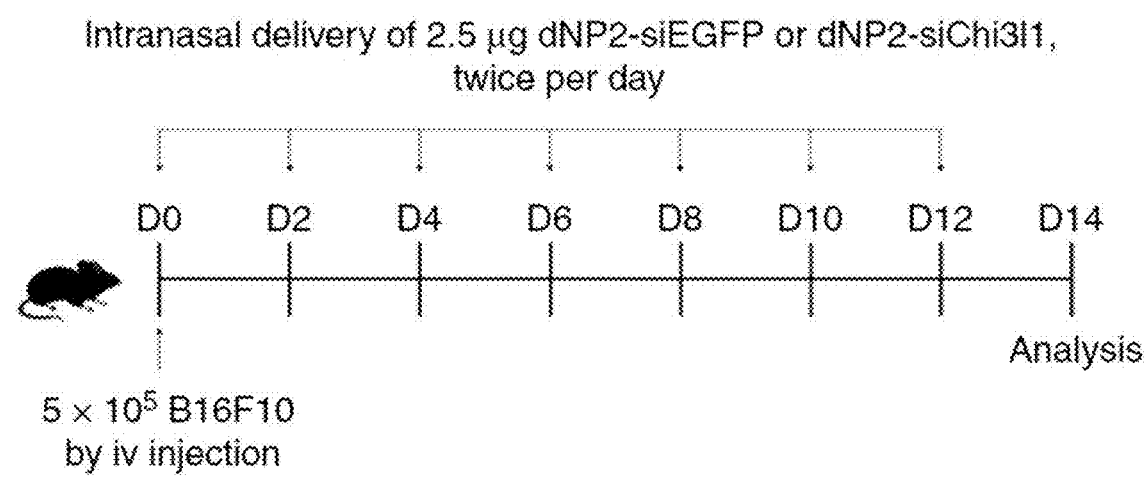
FIG. 16A schematically shows a method for preparing control and experimental groups using pulmonary melanoma metastasis animal models.
Figure 16B:
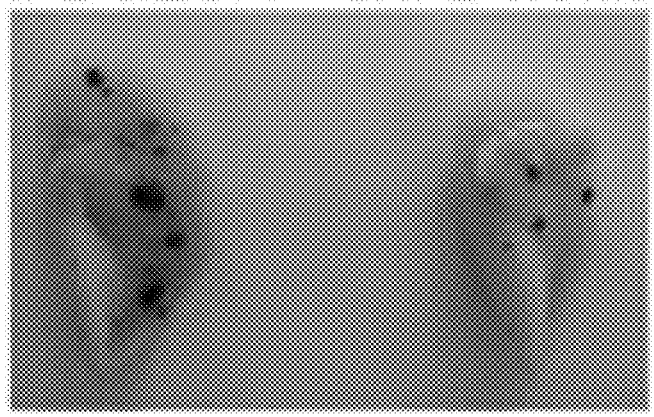
FIG. 16B is an image showing lungs excised from pulmonary melanoma metastasis animal models after treatment with dNP2-siEGFP or dNP2-siChi3l1.

FIG. 16A schematically shows a method for preparing control and experimental groups using pulmonary melanoma metastasis animal models. FIG. 16B is an image showing lungs excised from pulmonary melanoma metastasis animal models after treatment with dNP2-siEGFP or dNP2-siChi3l1. In both groups, melanoma colonies on the lung surface were observed. Specifically, the formation of melanoma colonies was significantly inhibited in the melanoma lung metastasis animal model treated with dNP2-siChi3l1 compared to in the group treated with dNP2-siEGFP.

Figure 16C:
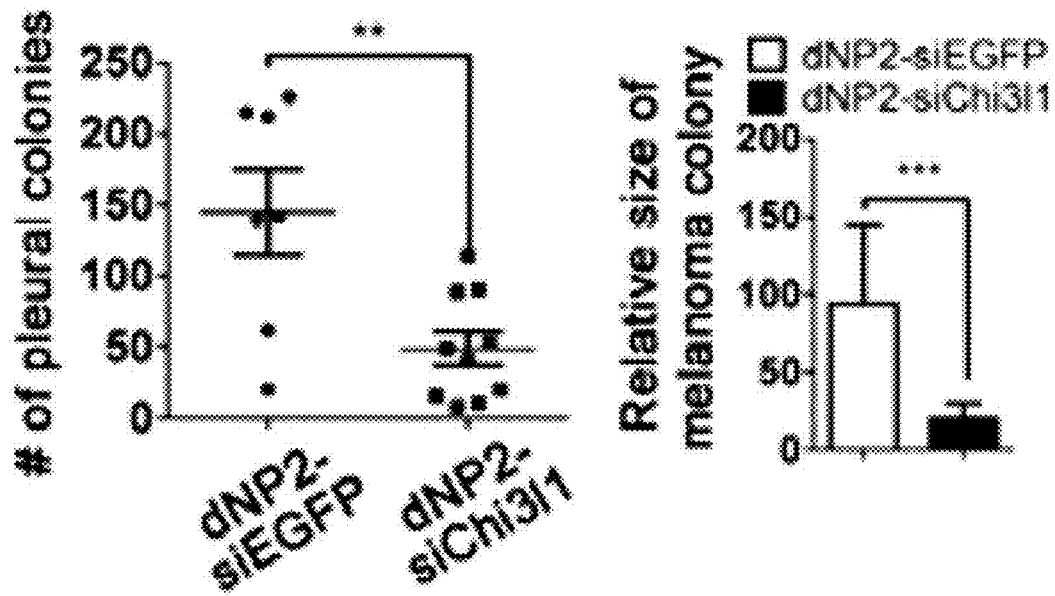
FIG. 16C shows the relative sizes and numbers of pleural colonies in the lungs of pulmonary melanoma metastasis animal models after treatment with dNP2-siEGFP or dNP2-siChi3l1.

FIG. 16C shows the relative sizes and numbers of pleural colonies in the lungs of pulmonary melanoma metastasis animal models after treatment with dNP2-siEGFP or dNP2-siChi3l1. As shown in FIG. 16C, the formation of melanoma colonies was significantly inhibited in the melanoma lung metastasis animal model treated with dNP2-siChi3l1 compared to in the group treated with dNP2-siEGFP. Data are mean±SD of at least three independent experiments. *p<0.05, p<0.01, * p<0.001.

Figure 16D:
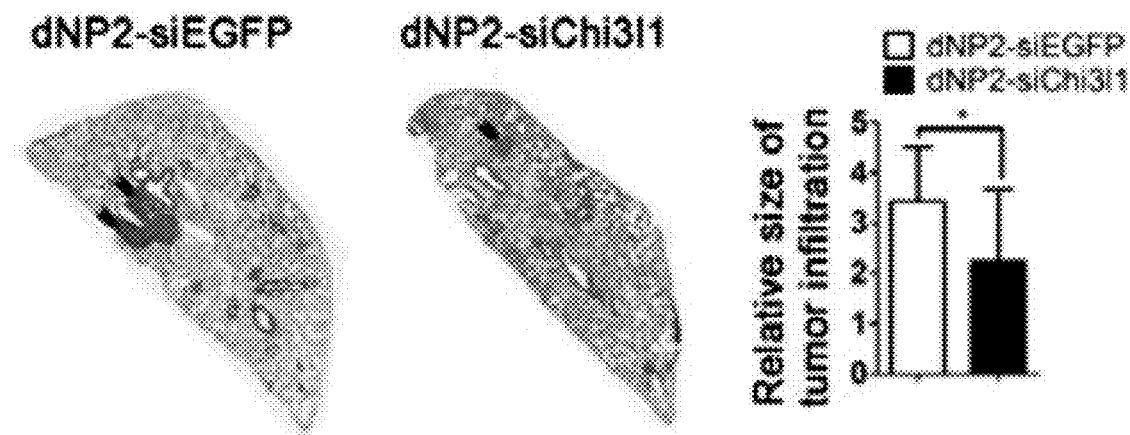
FIG. 16D shows optical microscopy images of H&E stained lung sections from an experimental group treated with dNP2-siChi3l1 complex and a control group treated with dNP2-siEGFP. Data are mean±SD of at least three independent experiments. *p<0.05, p<0.01, *p<0.001.

FIG. 16D shows optical microscopy images of H&E stained lung sections from an experimental group treated with dNP2-siChi3l1 complex and a control group treated with dNP2-siEGFP. Data are mean±SD of at least three independent experiments. *p<0.05, p<0.01, * p<0.001.

As shown in FIG. 16D, histological analysis of sectioned slides revealed that infiltrated tumors around blood vessels were significantly decreased in the experimental group received dNP2-siChi3l1 compared to in the control group received dNP2-siEGFP.

Figure 16E:
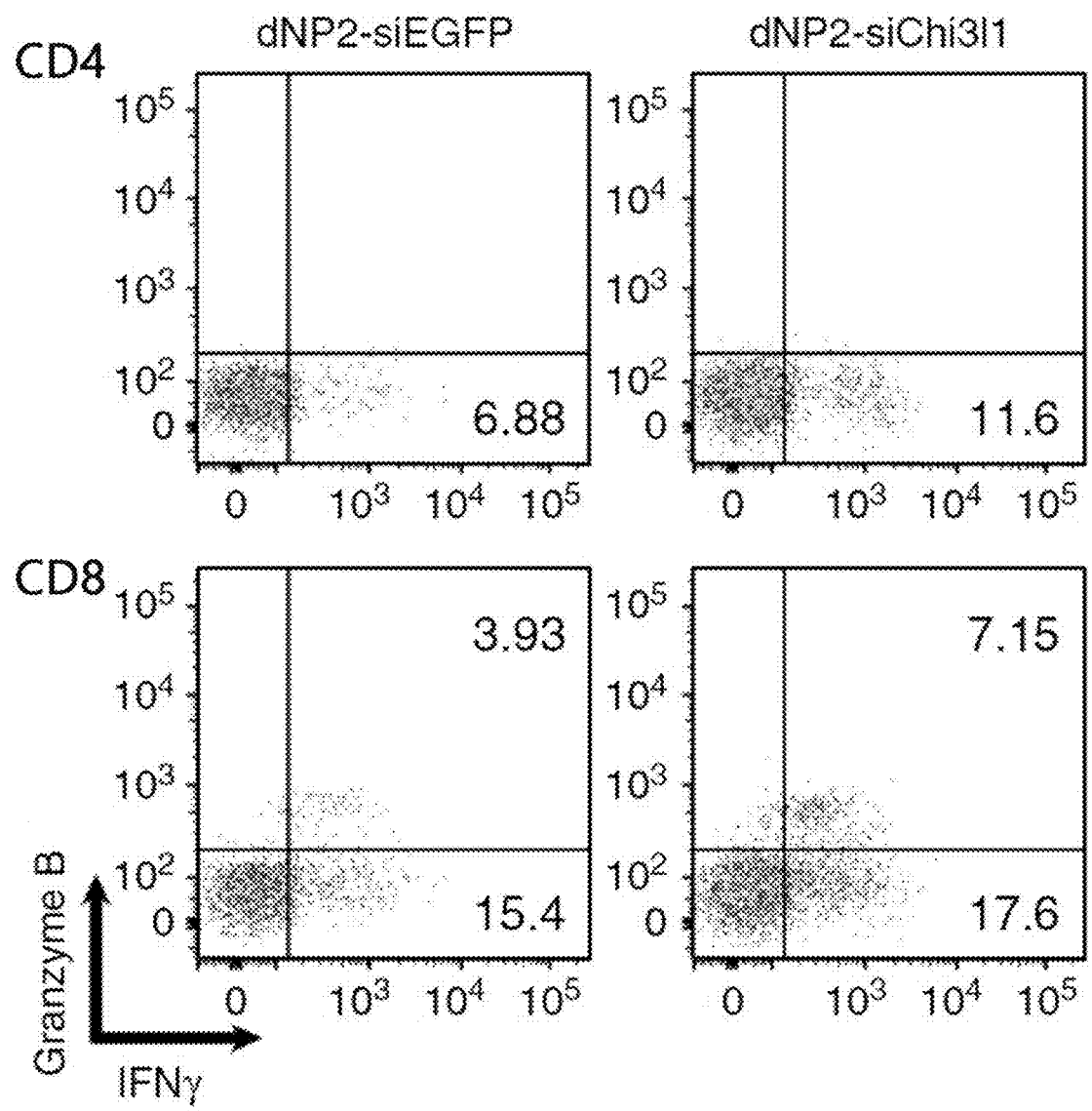
FIG. 16E shows the results of flow cytometry for lung lymphocytes isolated from an experimental group treated with dNP2-siChi3l1 complex and a control group treated with dNP2-siEGFP complex by Percoll and IFNγ and Granzyme B expression levels in CD4 and CD8 T cells.

FIG. 16E shows the results of flow cytometry for lung lymphocytes isolated from an experimental group treated with dNP2-siChi3l1 complex and a control group treated with dNP2-siEGFP complex by Percoll and IFNγ and Granzyme B expression levels in CD4 and CD8 T cells.

As shown in FIG. 16E, the numbers of IFNγ-producing CD4 T cells and CD8 T cells was increased in the experimental group treated with dNP2-siChi3l1 complex.

Figure 16F:
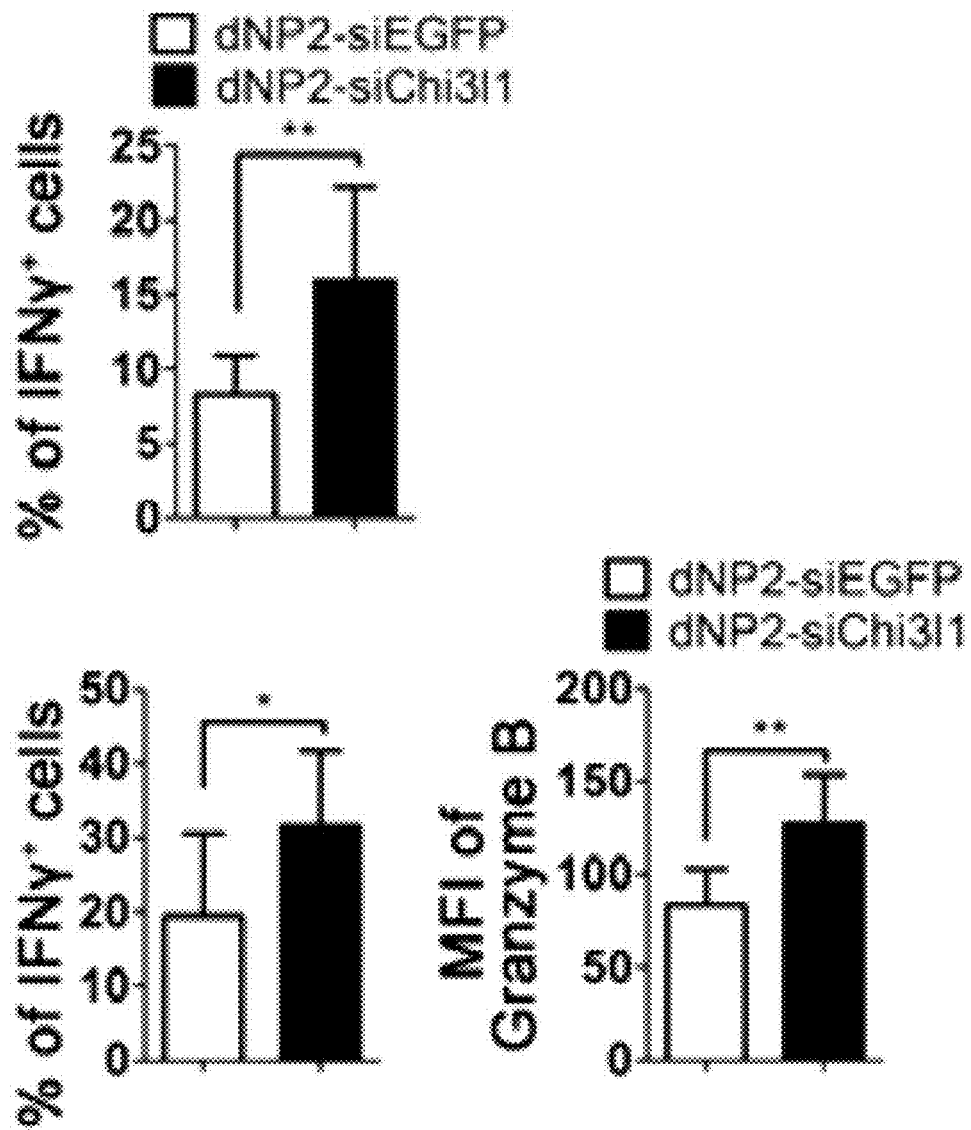
FIG. 16F shows T-bet expression levels in CD4$^+$IFNγ$^+$or CD8$^+$IFNγ$^+$population, which were analyzed by intracellular cytokine staining in lung tissues isolated from an experimental group treated with dNP2-siChi3l1 complex and a control group treated with dNP2-siEGFP.
Figure 16G:
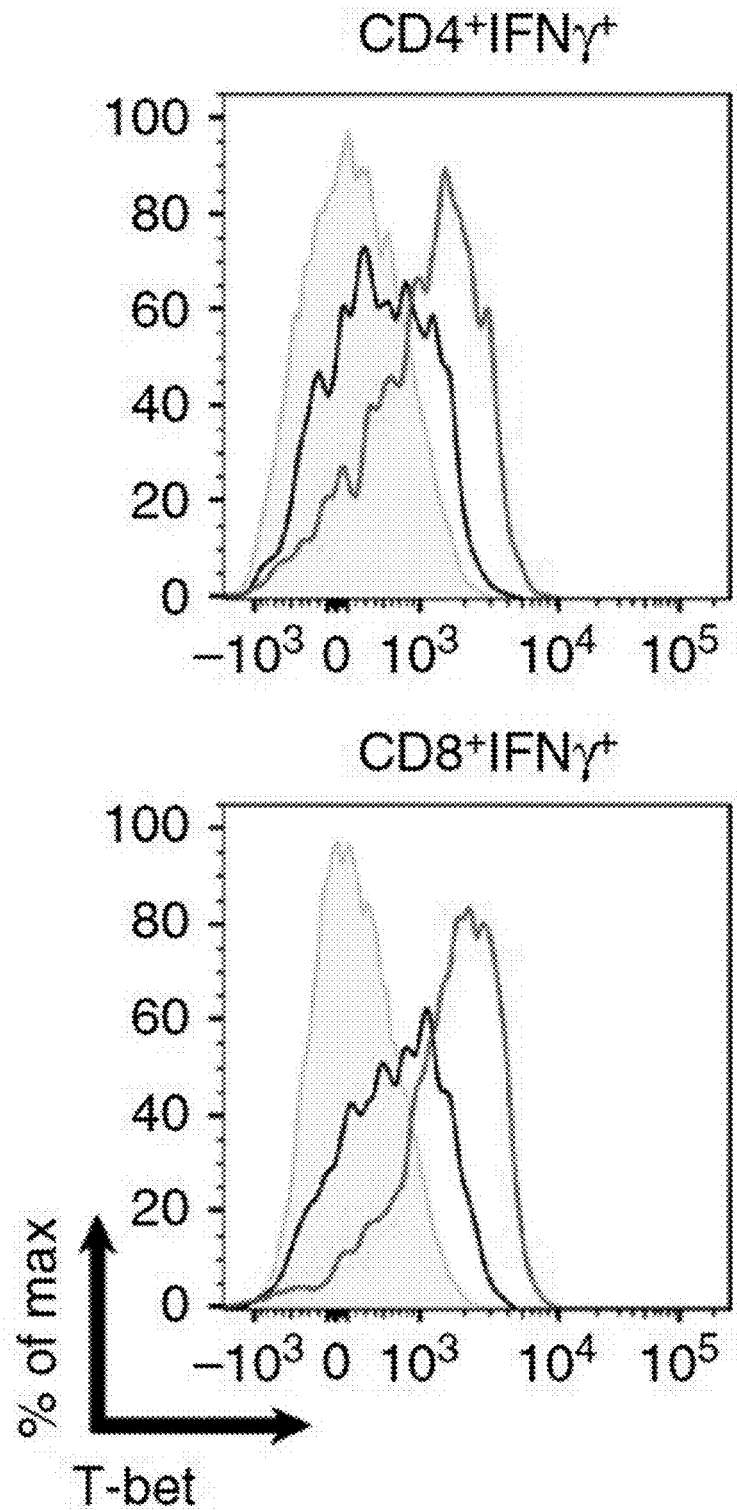
FIGS. 16G and 16H specifically show MFI analyzed in FIG. 16F. Data are mean±SD of at least three independent experiments. *p<0.05, p<0.01, *p<0.001.
Figure 16H:
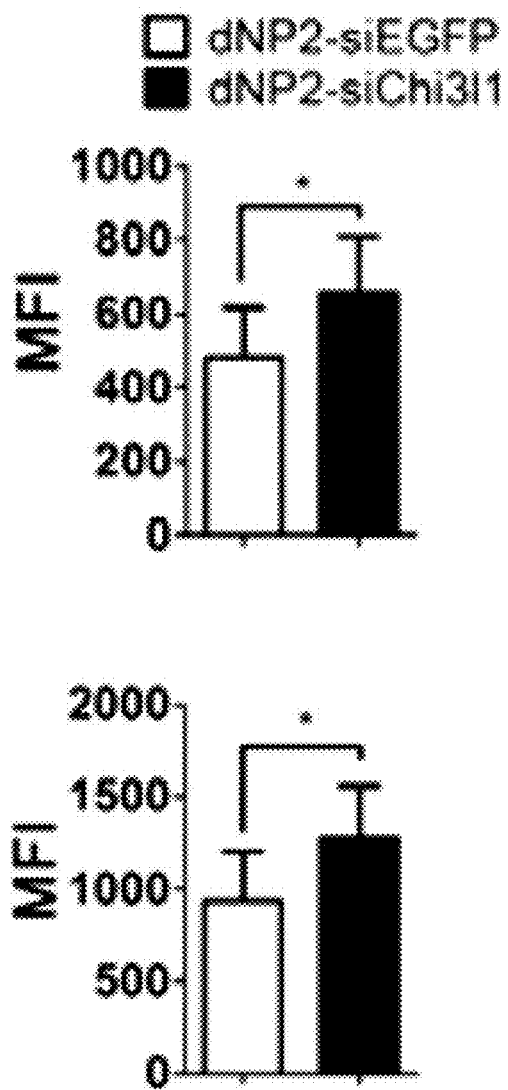

FIG. 16F shows T-bet expression levels in CD4$^+$IFN-γ$^+$ or CD8$^+$IFNγ$^+$ population, which were analyzed by intracellular cytokine staining in lung tissues isolated from an experimental group treated with dNP2-siChi3l1 complex and a control group treated with dNP2-siEGFP. FIGS. 16G and 16H specifically show MFI analyzed in FIG. 16F. Data are mean±SD of at least three independent experiments. *p<0.05, p<0.01, * p<0.001.

As shown in FIGS. 16F, 16H, and 16G, the intensities of T-bet and Granzyme B in both CD5 T cells and CD8 T cells in the experimental group treated with dNP2-siChi3l1 complex were significantly higher than those in the control group.

Figure 16I:
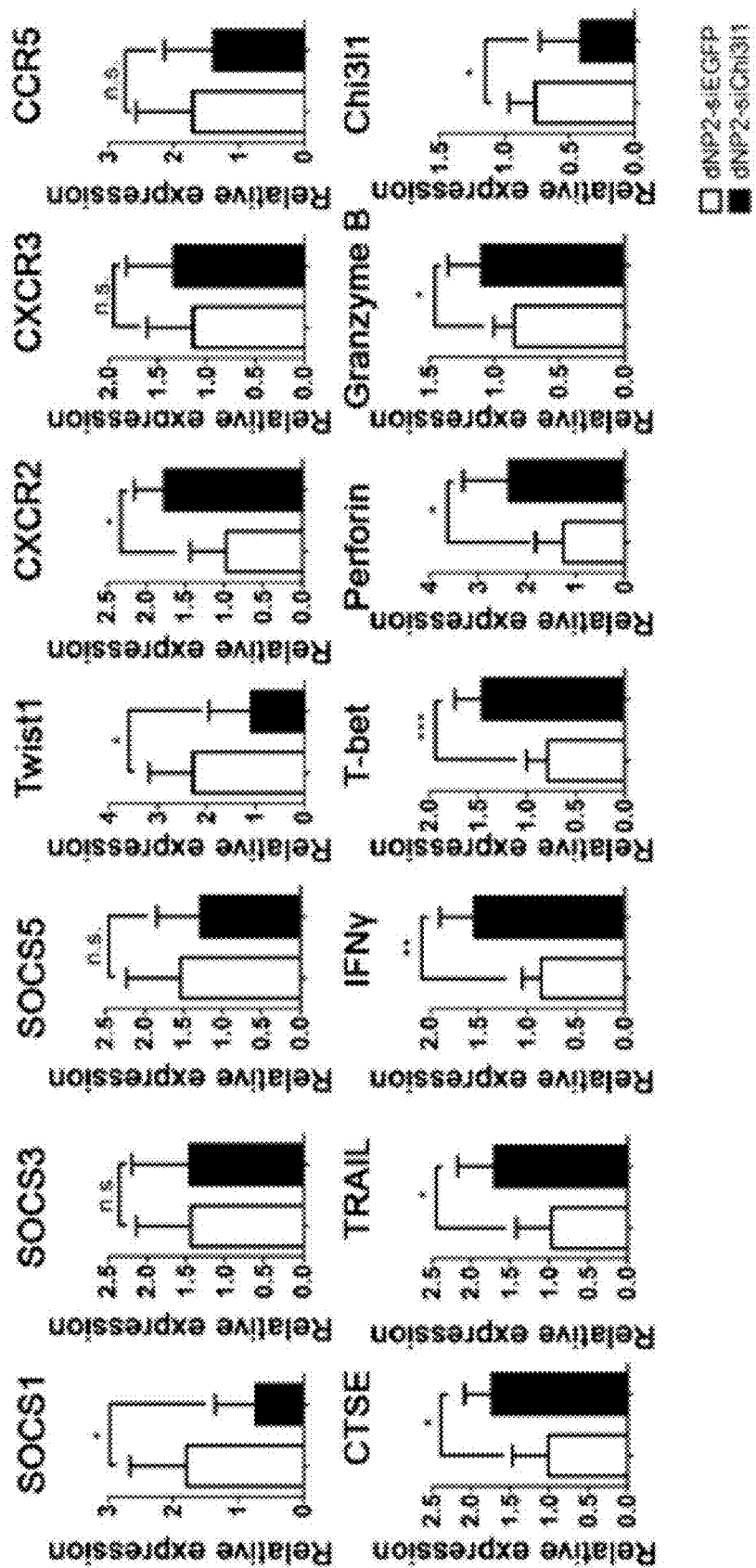
FIG. 16I shows the expression of targeting genes in lung lymphocyte fractions isolated from an experimental group treated with dNP2-siChi3l1 complex and a control group treated with dNP2-siEGFP complex by Percoll. Data are mean±SD of at least three independent experiments. *p<0.05, p<0.01, *p<0.001.

FIG. 16I shows the expression of targeting genes in lung lymphocyte fractions isolated from an experimental group treated with dNP2-siChi3l1 complex and a control group treated with dNP2-siEGFP complex by Percoll. Data are mean±SD of at least three independent experiments. *p<0.05, p<0.01, * p<0.001.

As shown in FIG. 16I, the experimental group treated with dNP2-siChi3l1 complex increased the gene expression of CTSE, TRAL, IFNγ, T-bet, Perforin, and Granzyme B related to anti-tumor immunity and decreased the expression of Th1 Twist1 and SOCS1. Taken together, these results suggest that the dNP2-siChi3l1 complex is an active ingredient that is effective in greatly preventing or treating the anti-tumor immune responses of Th1 and CTL.

Figure 17:
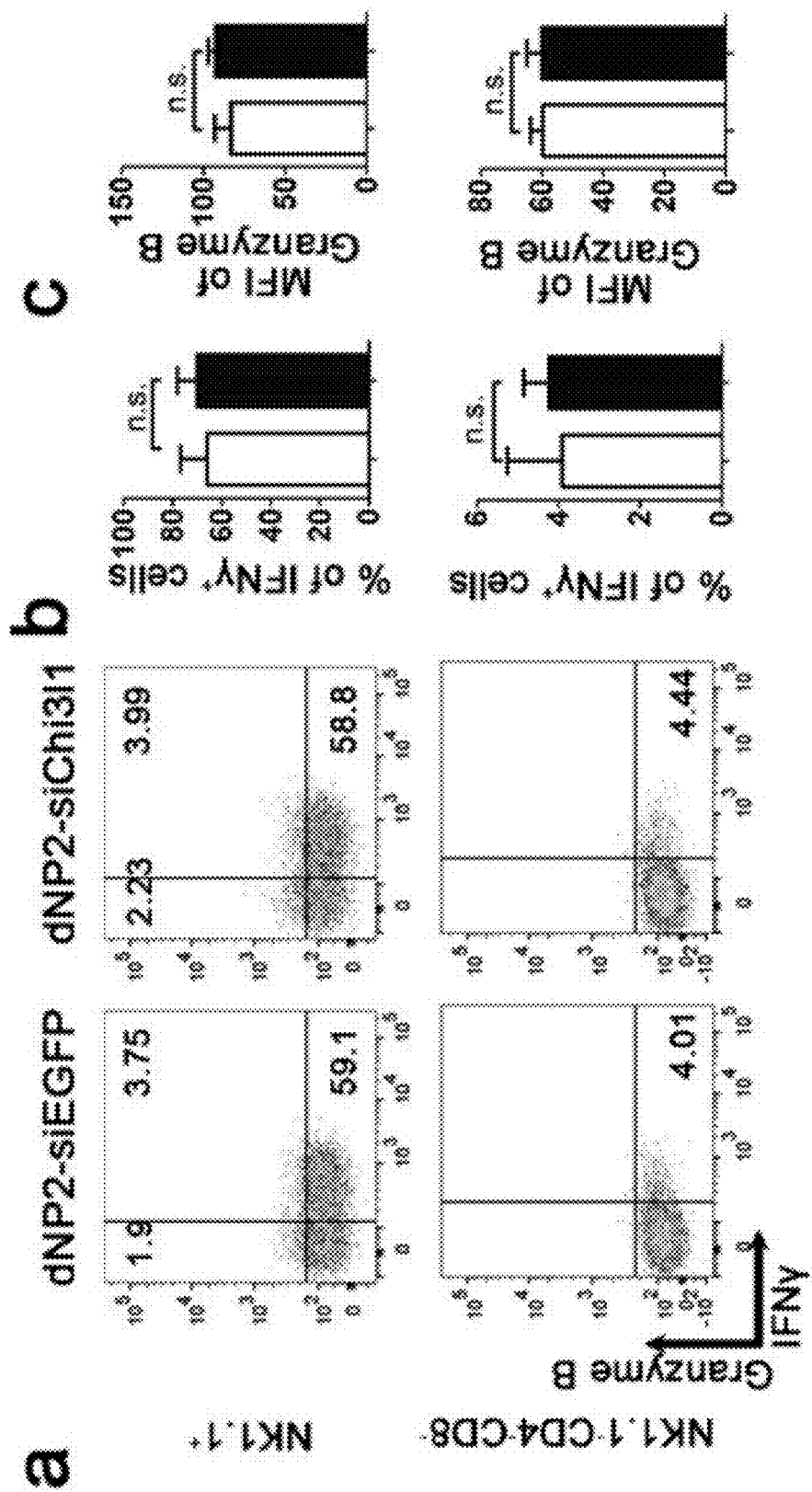
FIG. 17 shows experiments for confirming that the functions of NK cells were not affected in an experimental group treated with dNP2-siChi3l1 complex. (a) of FIG. 17 shows the results of flow cytometry for NK cells (NK1.1$^+$CD4$^-$CD8$^-$) and non-lymphocytic population (NK1.1$^-$CD4$^-$CD8$^-$) isolated from lung lymphocytes from an experimental group treated with dNP2-siChi3l1 complex and a control group treated with dNP2-siEGFP complex by Perocoll.

FIG. 17 shows experiments for confirming that the functions of NK cells were not affected in an experimental group treated with dNP2-siChi3l1 complex. (a) of FIG. 17 shows the results of flow cytometry for NK cells (NK1.1$^+$CD4$^-$CD8$^-$) and non-lymphocytic population (NK1.1$^-$CD4$^-$CD8$^-$) isolated from lung lymphocytes from an experimental group treated with dNP2-siChi3l1 complex and a control group treated with dNP2-siEGFP complex by Perocoll.

(b) of FIG. 17 shows the percentage of IFNγ$^+$ cells in each group, which were calculated from the experimental data of (a) of FIG. 17. (c) of FIG. 17 shows the mean fluorescence intensity (MFI) of Granzyme B in each group, which were calculated from the experimental data of (a) of FIG. 17. Data are mean±SD of at least five independent experiments. *p<0.05,  p<0.01, * p<0.001.

As shown in FIG. 17, no significant difference was noted in other cells or NK cells on IFNγ+ and Granzyme B expression.

EXPERIMENTAL EXAMPLE 8

Inhibitory Effect of dNP2-siChi3l1 Complex on Melanoma Lung Metastasis Depending on Route of Administration A. Intranasal Administration The mouse melanoma cell line (B16F10) established from C57BL6/J mouse melanoma was provided by HA Sang-Jun (Yonsei University). After culturing to 90% confluence in complete DMEM, cells were harvested, adjusted to $10^6$ cells/mL in pre-warmed PBS, and $5\times10^5$ cells were injected into mice via the tail vein.

2 days after melanoma cell line injection (after cell metastasis was already finished), 2.5 µg of dNP2-siChi3l1 complex (experimental group) or 2.5 µg of dNP2-siEGFP (control group) was intranasally administered every other day for 12 days. At day 14, mice were sacrificed. Thereafter, the lungs, spleens, and inguinal lymph nodes were excised from the animals and observed.

Figure 18:
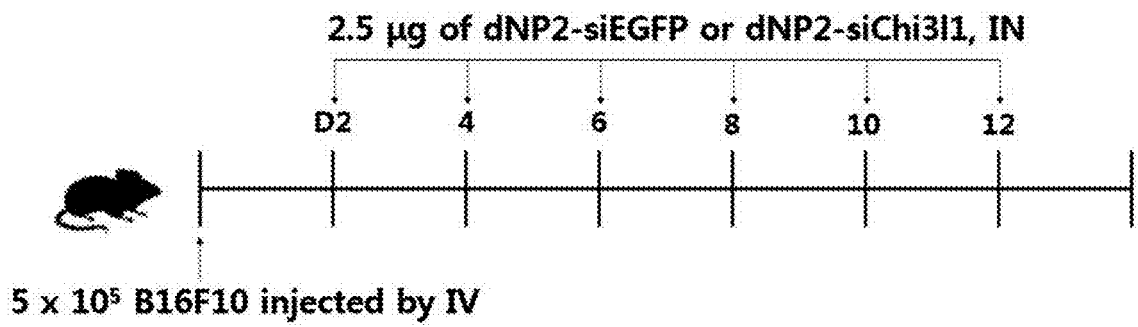
FIG. 18 is a diagram showing experimental conditions of an experimental group and a control group in Experimental Example 8.A.
Figure 19:
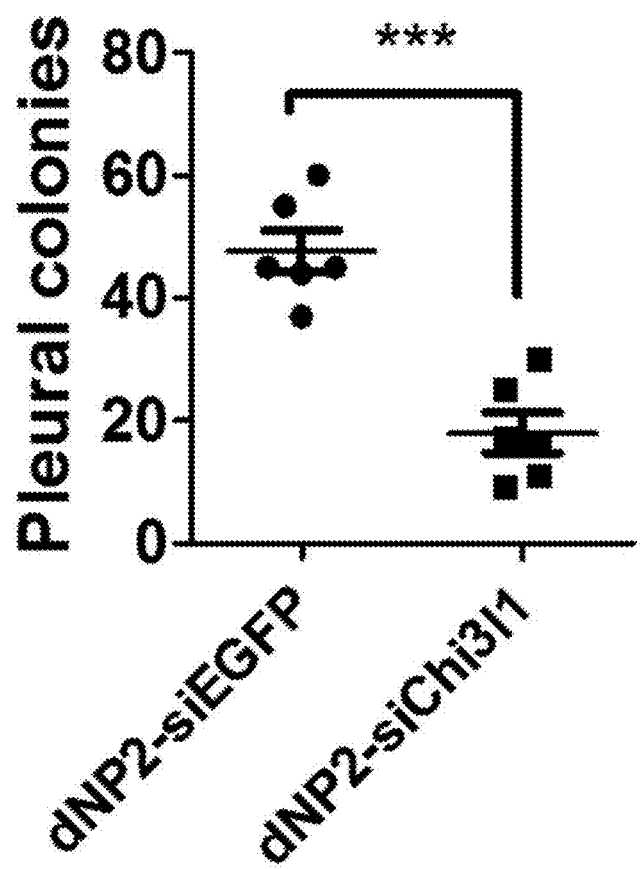
FIG. 19 shows the counted numbers of pleural colonies visualized as black dots on the lung surface in an experimental group and a control group in Experimental Example 8.A.
Figure 20:
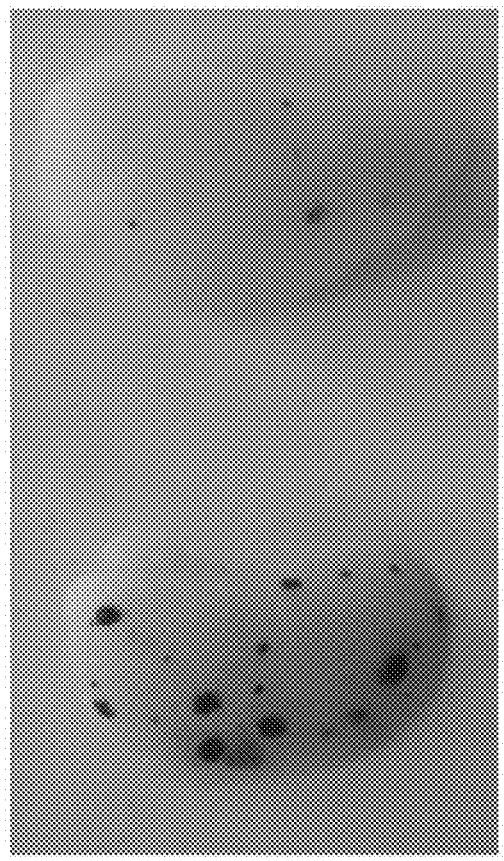
FIG. 20 is an image of the lungs excised from an experimental group and a control group in Experimental Example 8.A.

FIG. 18 is a diagram showing experimental conditions of the experimental group and the control group. FIG. 19 shows the counted numbers of pleural colonies visualized as black dots on the lung surface in the experimental group and the control group. FIG. 20 is an image of the lungs excised from the experimental group and the control group.

As shown in FIGS. 19 and 20, intranasal administration of dNP2-siChi3l1 complex decreased the number of melanoma cells metastasized to the lung by 2- to 6-fold.

Figure 21:
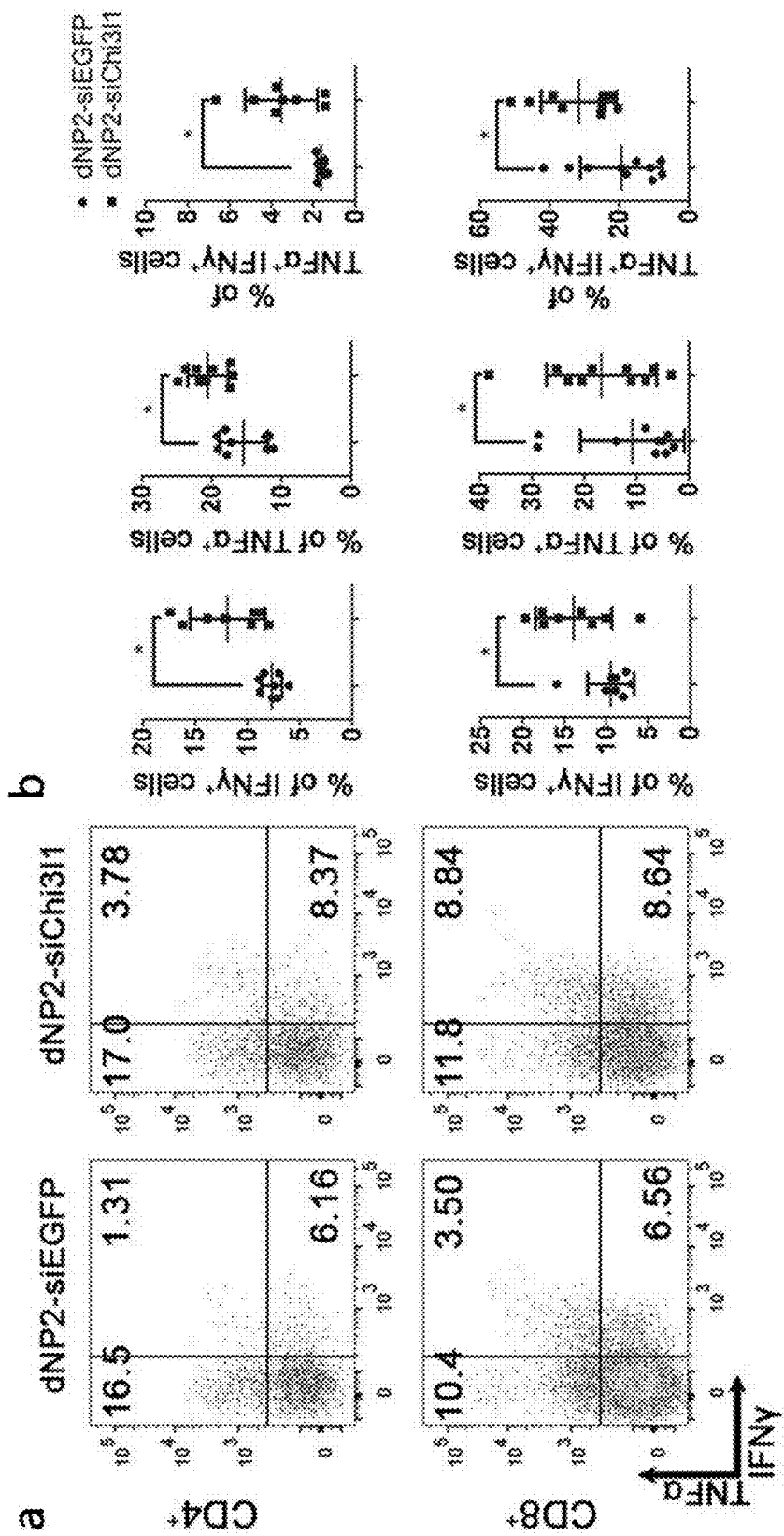
FIGS. 21 and 22 show the results of flow cytometric analysis for immune cells isolated from the lungs excised from an experimental group and a control group by Percoll gradients in Experimental Example 8.A.
Figure 22:
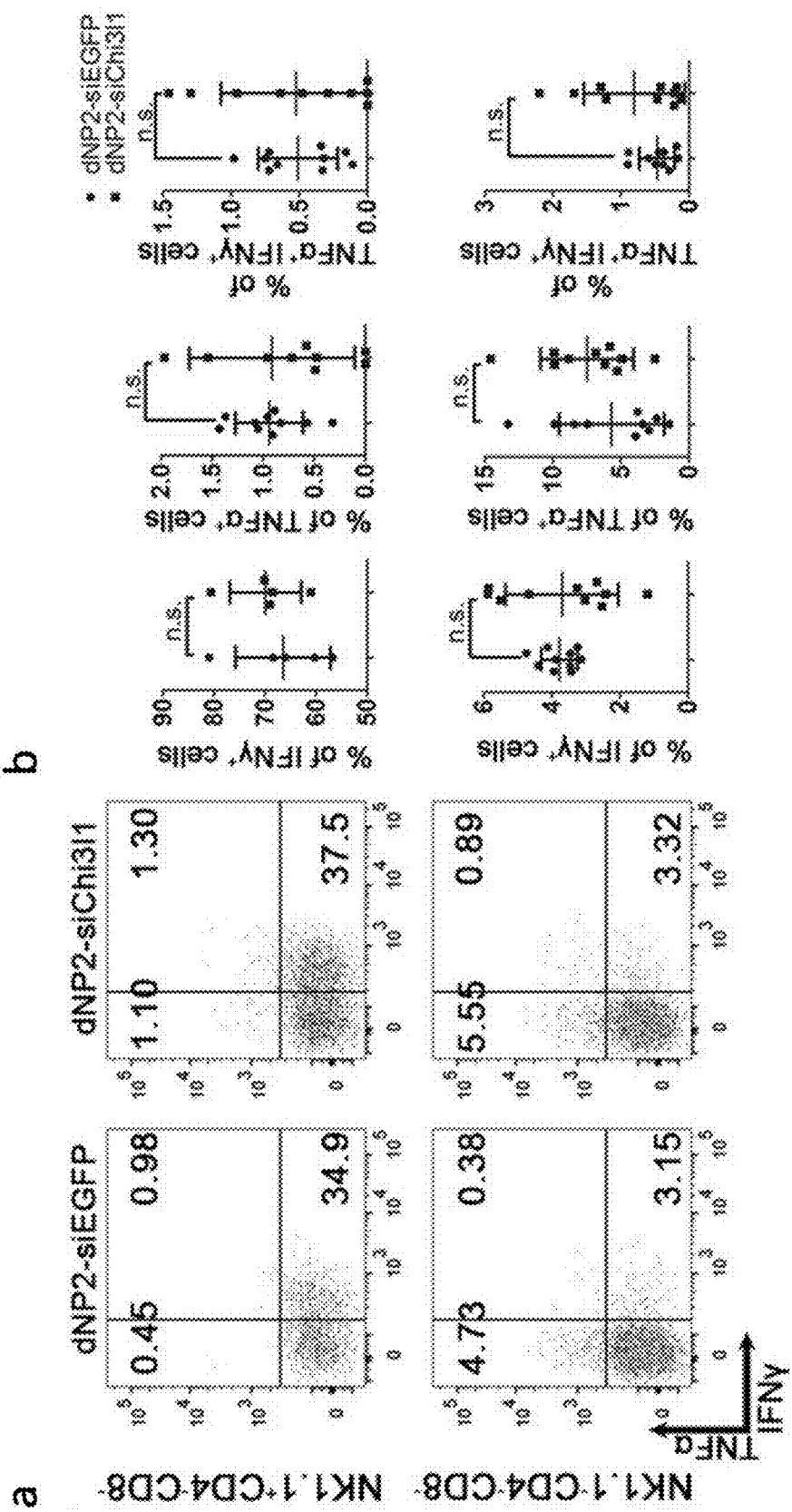

FIGS. 21 and 22 show the results of flow cytometric analysis for immune cells isolated from the lungs excised from the experimental group and the control group by Percoll gradients. a and b of FIG. 21 compare how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of a of FIG. 21 and a of FIG. 22 are graphically shown in b of FIG. 21 and b of FIG. 22, respectively.

Increased expressions of TNFα cytokine in CD4 T cells and CD8 T cells were observed in the lung of the experimental group received dNP2-siChi3l1 complex.

Figure 23:
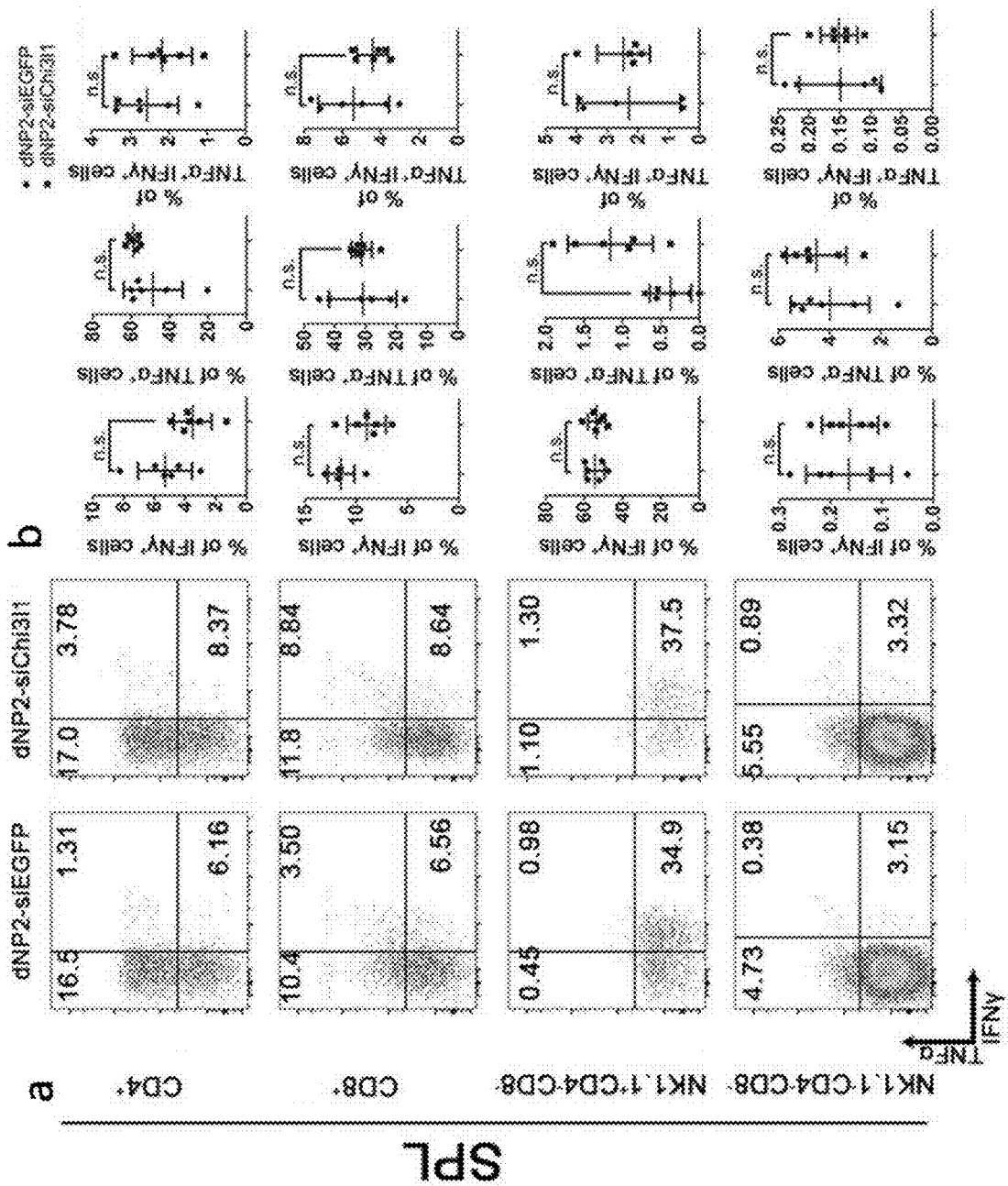
FIG. 23 shows the results of flow cytometric analysis for immune cells isolated from the spleens excised from an experimental group and a control group by Percoll gradients in Experimental Example 8.A.

FIG. 23 shows the results of flow cytometric analysis for immune cells isolated from the spleens excised from the experimental group and the control group by Percoll gradients. a of FIG. 23 compares how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of a of FIG. 23 are graphically shown in b of FIG. 23.

No significant cytokine changes from CD4 T cells and CD8 T cells were observed in the spleens of the experimental group received dNP2-siChi3l1 complex and the control group received dNP2-siEGFP.

Figure 24:
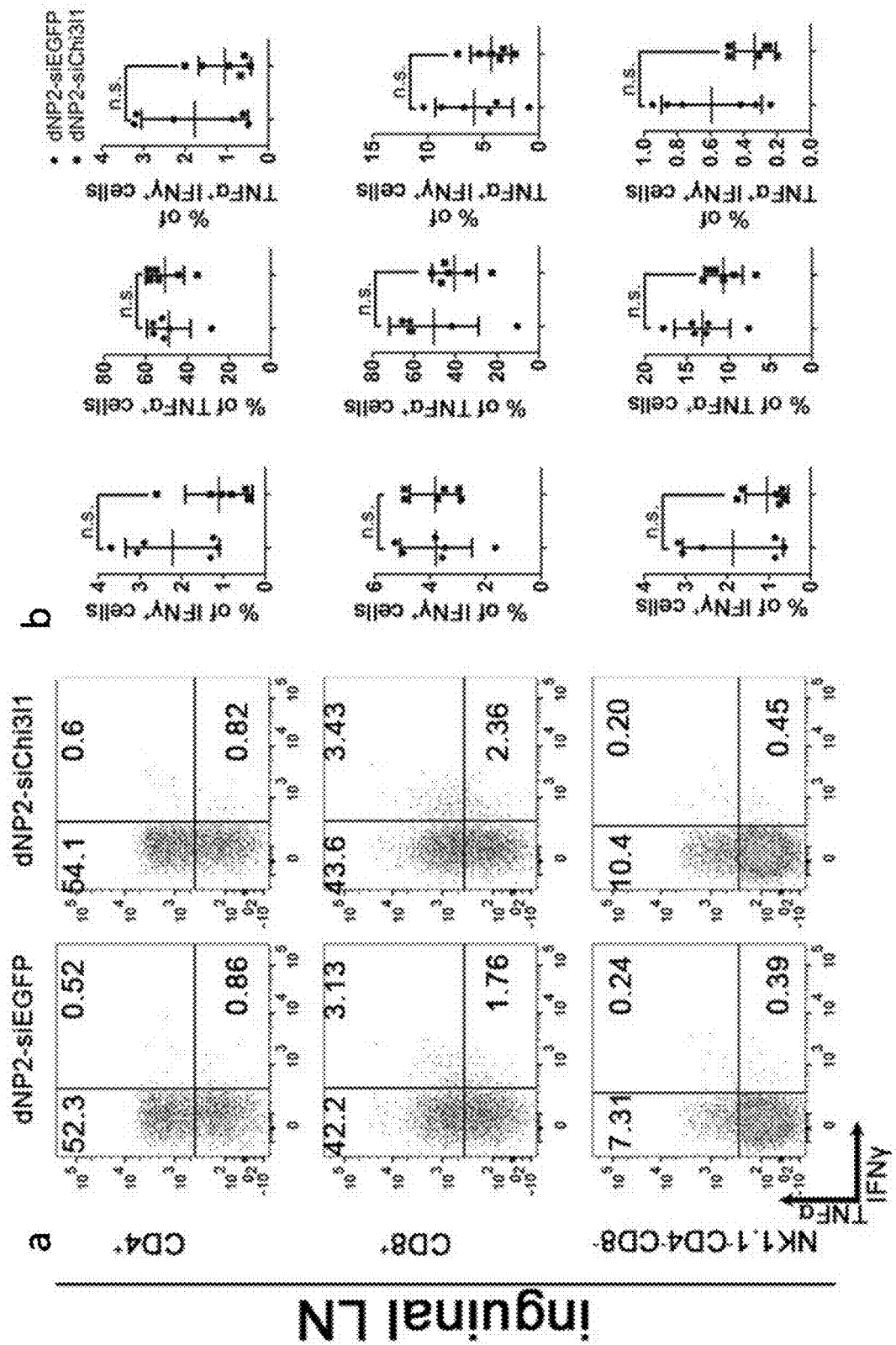
FIG. 24 shows the results of flow cytometric analysis for immune cells isolated from the inguinal lymph nodes resected from an experimental group and a control group by Percoll gradients in Experimental Example 8.A.

FIG. 24 shows the results of flow cytometric analysis for immune cells isolated from the inguinal lymph nodes resected from the experimental group and the control group by Percoll gradients. a of FIG. 24 compares how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of a of FIG. 24 are graphically shown in b of FIG. 24.

No significant cytokine changes from CD4 T cells and CD8 T cells were observed in the inguinal lymph nodes of the experimental group received dNP2-siChi3l1 complex and the control group received dNP2-siEGFP.

B. Administration Via Tail Vein

The mouse melanoma cell line (B16F10) established from C57BL6/J mouse melanoma was provided by HA Sang-Jun (Yonsei University). After culturing to 90% confluence in complete DMEM, cells were harvested, adjusted to $10^6$ cells/mL in pre-warmed PBS, and $5\times10^5$ cells were injected into mice via the tail vein.

2 days after melanoma cell line injection (after cell metastasis was already finished), 5 µg of dNP2-siChi3l1 complex (experimental group) or 5 µg of dNP2-siEGFP (control group) was administered via the tail vein every other day for 12 days. At day 14, mice were sacrificed. Thereafter, the lungs, spleens, and inguinal lymph nodes were excised from the animals and observed. The amount of each of the complexes administered via the tail vein was twice larger than that via an intranasal route.

Figure 25:
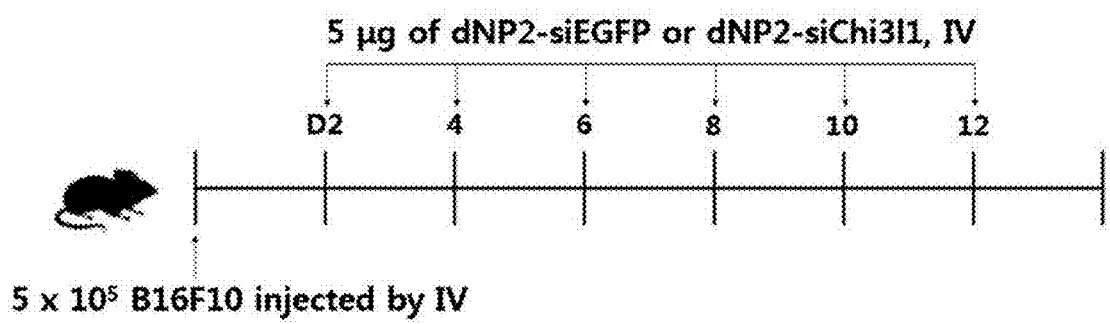
FIG. 25 is a diagram showing experimental conditions of an experimental group and a control group in Experimental Example 8.B.
Figure 26:
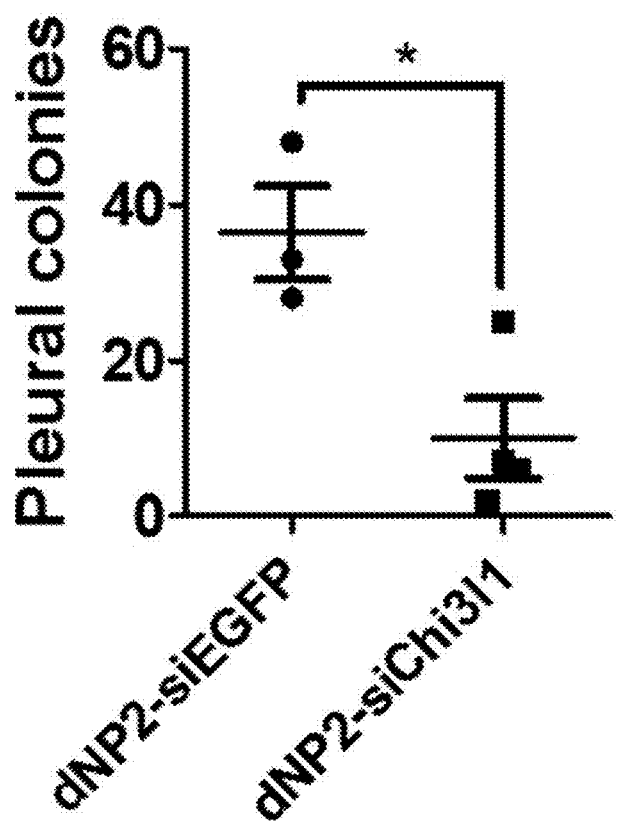
FIG. 26 shows the counted numbers of pleural colonies visualized as black dots on the lung surface in an experimental group and a control group Experimental Example 8.B.
Figure 27:
FIG. 27 is an image of the lungs excised from an experimental group and a control group in Experimental Example 8.B.

FIG. 25 is a diagram showing experimental conditions of the experimental group and the control group. FIG. 26 shows the counted numbers of pleural colonies visualized as black dots on the lung surface in the experimental group and the control group. FIG. 27 is an image of the lungs excised from the experimental group and the control group.

As shown in FIGS. 26 and 27, intranasal administration of dNP2-siChi3l1 complex decreased the number of melanoma cells metastasized to the lung by 2- to 4-fold.

Figure 28:
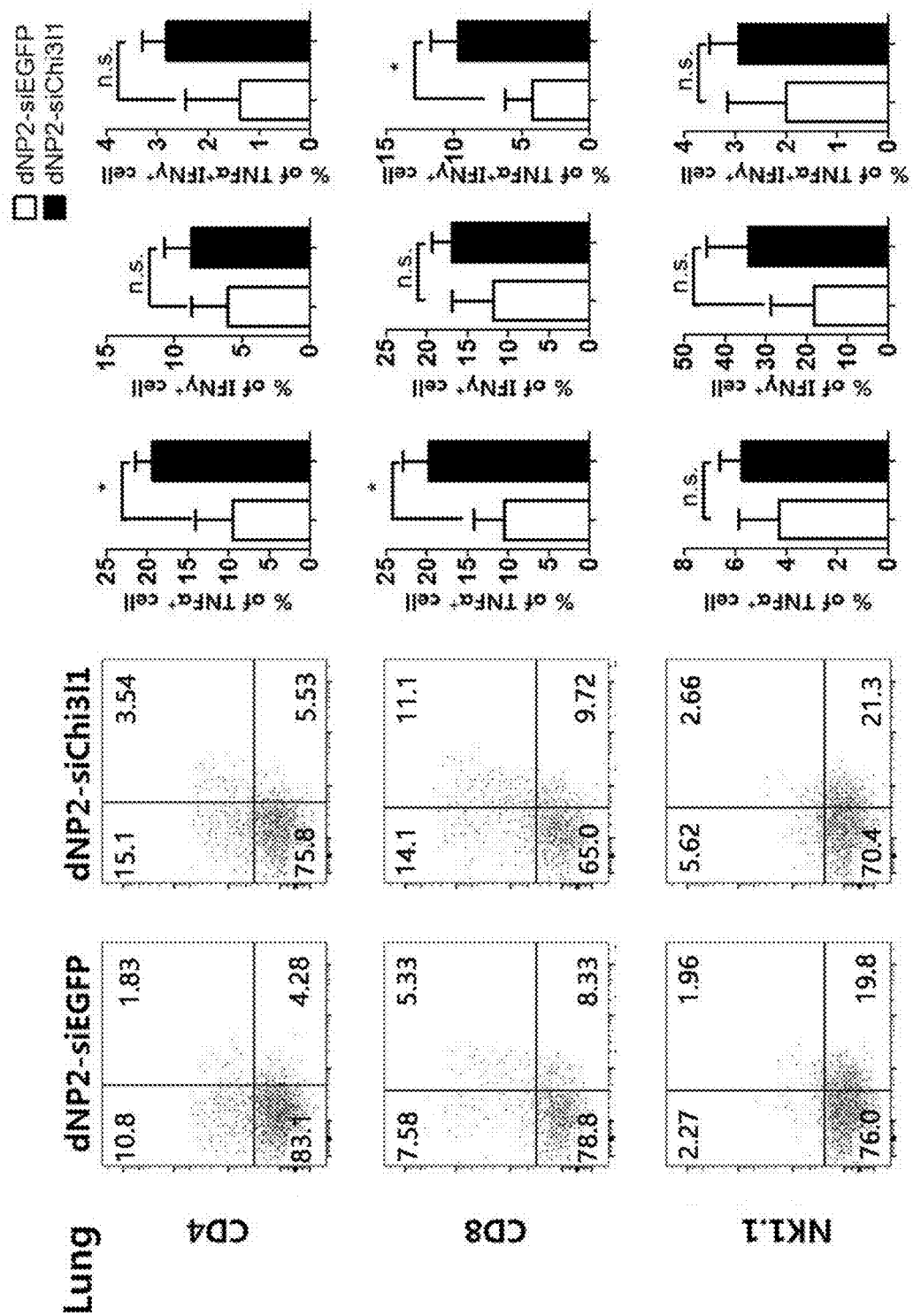
FIG. 28 shows the results of flow cytometric analysis for immune cells isolated from the lungs excised from an experimental group and a control group by Percoll gradients in Experimental Example 8.B.

FIG. 28 shows the results of flow cytometric analysis for immune cells isolated from the lungs excised from the experimental group and the control group by Percoll gradients. The left graphs compare how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of the left graphs are shown in the right graphs.

Increased expressions of TNFα cytokine in CD4 T cells and CD8 T cells were observed in the lung of the experimental group received dNP2-siChi3l1 complex. However, considering that the concentration of dNP2-Chi3l1 complex administered via the tail vein was 2-fold higher than that of the intranasally administered one in Experimental Example 8.A, the therapeutic and prophylactic effects of dNP2-Chi3l1 complex administered via the tail vein were inferior to those of the intranasal administered one.

Figure 29:
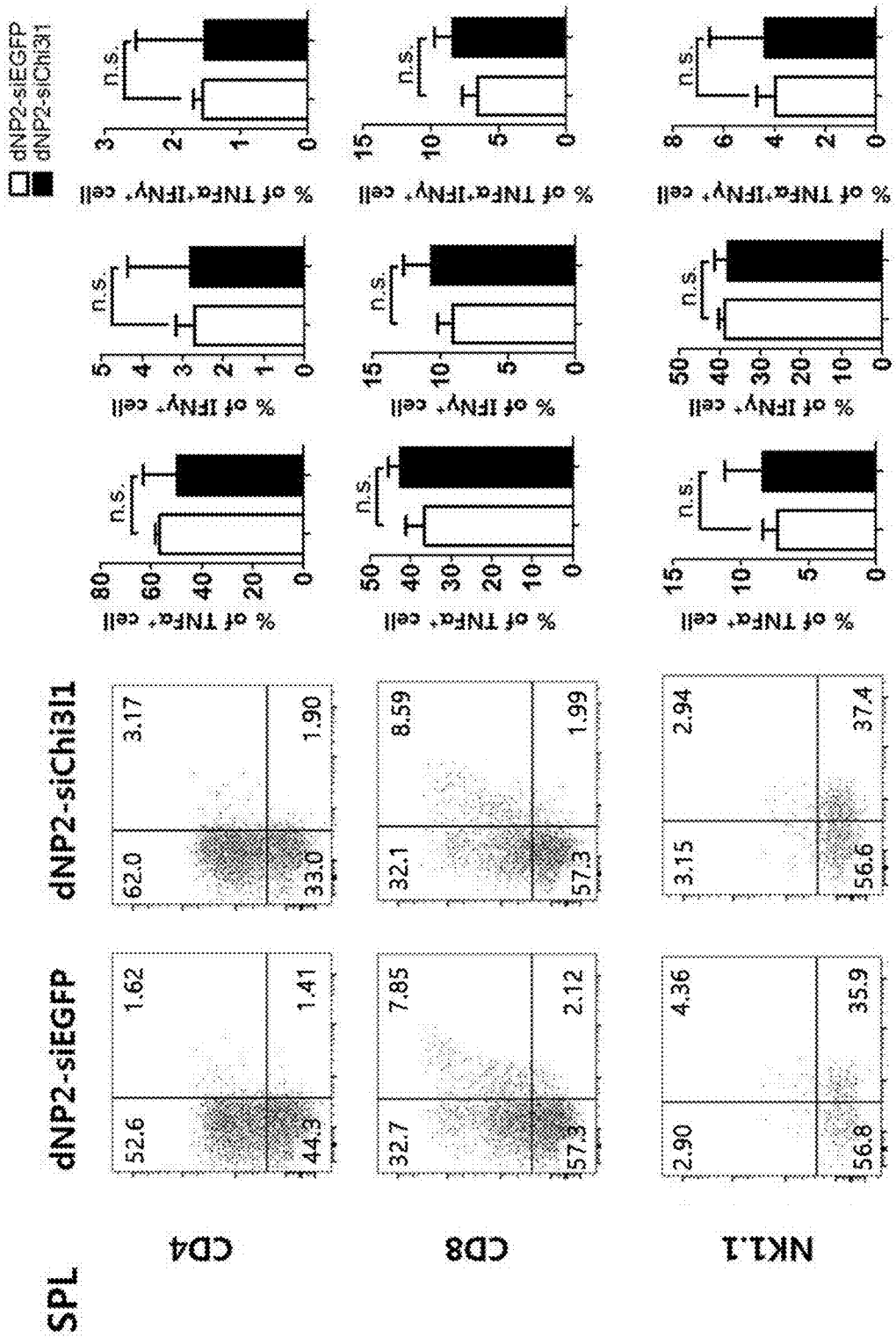
FIG. 29 shows the results of flow cytometric analysis for immune cells isolated from the spleens excised from an experimental group and a control group by Percoll gradients in Experimental Example 8.B.

FIG. 29 shows the results of flow cytometric analysis for immune cells isolated from the spleens excised from the experimental group and the control group by Percoll gradients. The left graphs compare how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of the left graphs are shown in the right graphs.

No significant cytokine changes from CD4 T cells and CD8 T cells were observed in the spleens of the experimental group received dNP2-siChi3l1 complex and the control group received dNP2-siEGFP.

Figure 30:
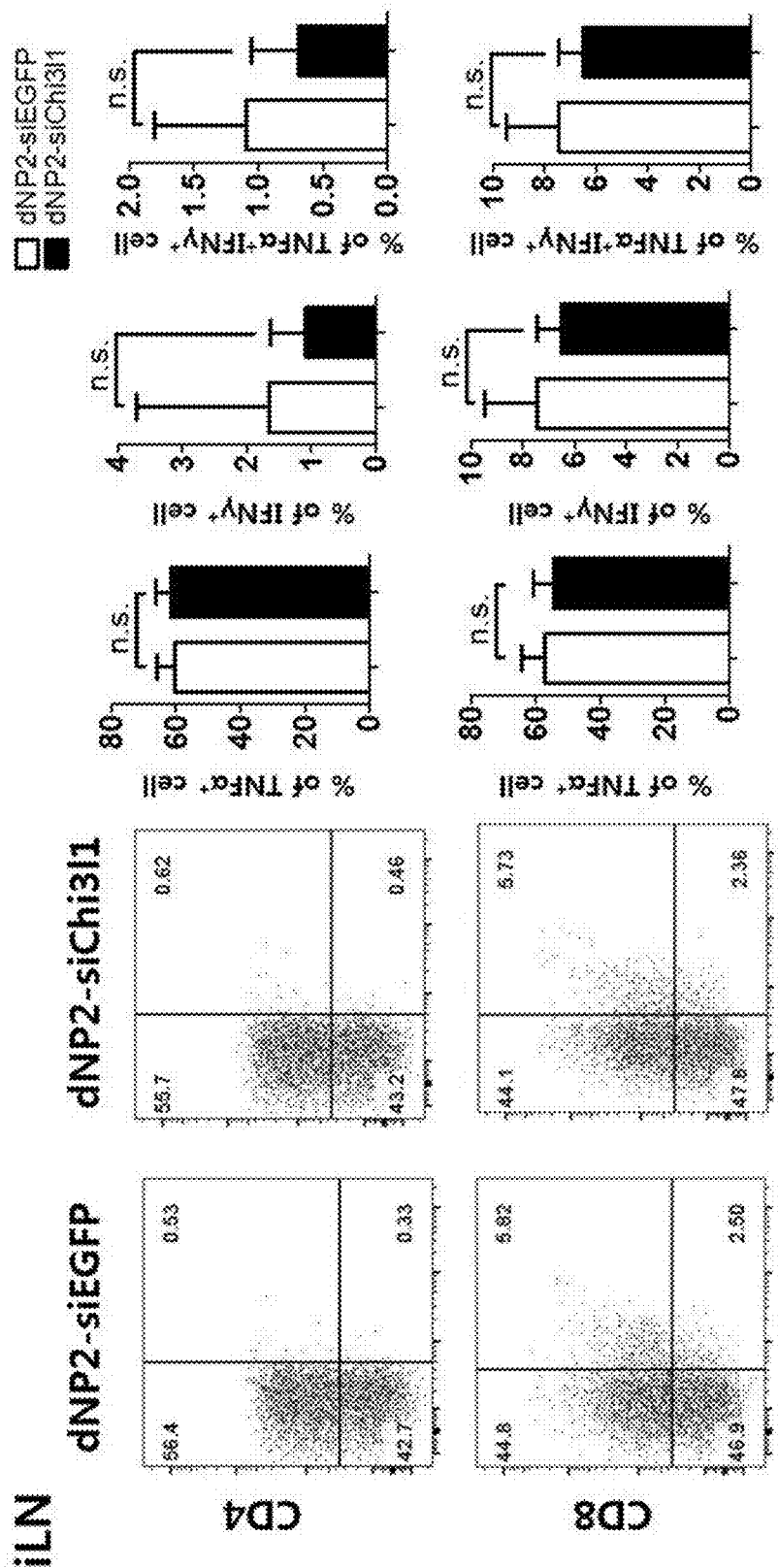
FIG. 30 shows the results of flow cytometric analysis for immune cells isolated from the inguinal lymph nodes resected from an experimental group and a control group by Percoll gradients in Experimental Example 8.B.

FIG. 30 shows the results of flow cytometric analysis for immune cells isolated from the inguinal lymph nodes resected from the experimental group and the control group by Percoll gradients. The left graphs compare how much cytokine proteins IFNγ (x axis) and TNFα (y axis) capable of inhibiting cancer were expressed from the immune cells. The first quadrant shows the expression of both IFNγ and TNFα, the second quadrant shows the expression of TNFα only, the third quadrant shows the expression of none of IFNγ and TNFα, and the fourth quadrant shows the expression of IFNγ only. The analytic results of the left graphs are shown in the right graphs.

No significant cytokine changes from CD4 T cells and CD8 T cells were observed in the inguinal lymph nodes of the experimental group received dNP2-siChi3l1 complex and the control group received dNP2-siEGFP.

---

The invention claimed is:

1. A pharmaceutical composition comprising, as an active ingredient, a complex of a cell-penetrating peptide having the sequence set forth in SEQ ID NO: 2 and a Chi3l1 siRNA having the sequence set forth in SEQ ID NO: 1.

2. The pharmaceutical composition according to claim 1, wherein the pharmaceutical composition has the ability to penetrate the nasal mucosa, the bronchial mucosa or pulmonary epithelial cells.

3. A method for preventing or treating pulmonary metastasis of cancer in a subject in need thereof, comprising administering the pharmaceutical composition according to claim 1 to the subject via an intranasal route.

4. The method for preventing or treating pulmonary metastasis of cancer according to claim 3, wherein the administering is an inhalation of a spray or powder.

* * * * *

SEQUENCE LISTING

```
<160> NUMBER OF SEQ ID NOS: 68

<210> SEQ ID NO 1
<211> LENGTH: 21
<212> TYPE: RNA
<213> ORGANISM: Artificial Sequence
<220> FEATURE:
<223> OTHER INFORMATION: siChi3l1

<400> SEQUENCE: 1
caggaguuua aucucuugca a                                              21

<210> SEQ ID NO 2
<211> LENGTH: 44
<212> TYPE: PRT
<213> ORGANISM: Artificial Sequence
<220> FEATURE:
<223> OTHER INFORMATION: dNP2-HA2

<400> SEQUENCE: 2

Lys Ile Lys Lys Val Lys Lys Lys Gly Arg Lys Gly Ser Lys Ile Lys
1               5                   10                  15

Lys Val Lys Lys Lys Gly Arg Lys Gly Leu Phe Gly Ala Ile Ala Gly
            20                  25                  30

Phe Ile Glu Asn Gly Trp Glu Gly Met Ile Asp Gly
        35                  40

<210> SEQ ID NO 3
<211> LENGTH: 20
<212> TYPE: DNA
<213> ORGANISM: Artificial Sequence
<220> FEATURE:
<223> OTHER INFORMATION: Actb

<400> SEQUENCE: 3
tgtccctgta tgcctctggt                                                20

<210> SEQ ID NO 4
<211> LENGTH: 19
<212> TYPE: DNA
<213> ORGANISM: Artificial Sequence
<220> FEATURE:
<223> OTHER INFORMATION: Actb

<400> SEQUENCE: 4
cacgcacgat ttccctctc                                                 19
```

```
<210> SEQ ID NO 5
<211> LENGTH: 22
<212> TYPE: DNA
<213> ORGANISM: Artificial Sequence
<220> FEATURE:
<223> OTHER INFORMATION: Chi3l1

<400> SEQUENCE: 5
gtacaagctg gtctgctact tc                                              22

<210> SEQ ID NO 6
<211> LENGTH: 21
<212> TYPE: DNA
<213> ORGANISM: Artificial Sequence
<220> FEATURE:
<223> OTHER INFORMATION: Chi3l1

<400> SEQUENCE: 6
atgtgctaag catgttgtcg c                                               21

<210> SEQ ID NO 7
<211> LENGTH: 19
<212> TYPE: DNA
<213> ORGANISM: Artificial Sequence
<220> FEATURE:
<223> OTHER INFORMATION: Tbx21

<400> SEQUENCE: 7
agcaaggacg gcgaatgtt                                                  19

<210> SEQ ID NO 8
<211> LENGTH: 21
<212> TYPE: DNA
<213> ORGANISM: Artificial Sequence
<220> FEATURE:
<223> OTHER INFORMATION: Tbx21

<400> SEQUENCE: 8
gggtggacat ataagcggtt c                                               21

<210> SEQ ID NO 9
<211> LENGTH: 23
<212> TYPE: DNA
<213> ORGANISM: Artificial Sequence
<220> FEATURE:
<223> OTHER INFORMATION: Runx3

<400> SEQUENCE: 9
gactccttcc ccaactatac acc                                             23

<210> SEQ ID NO 10
<211> LENGTH: 20
<212> TYPE: DNA
<213> ORGANISM: Artificial Sequence
<220> FEATURE:
<223> OTHER INFORMATION: Runx3

<400> SEQUENCE: 10
gtgctcgggt ctcgtatgaa                                                 20

<210> SEQ ID NO 11
<211> LENGTH: 21
<212> TYPE: DNA
<213> ORGANISM: Artificial Sequence
<220> FEATURE:
<223> OTHER INFORMATION: Ifng
```

<400> SEQUENCE: 11
atgaacgcta cacactgcat c 21

<210> SEQ ID NO 12
<211> LENGTH: 21
<212> TYPE: DNA
<213> ORGANISM: Artificial Sequence
<220> FEATURE:
<223> OTHER INFORMATION: Ifng
<400> SEQUENCE: 12
ccatcctttt gccagttcct c 21

<210> SEQ ID NO 13
<211> LENGTH: 21
<212> TYPE: DNA
<213> ORGANISM: Artificial Sequence
<220> FEATURE:
<223> OTHER INFORMATION: Gata3

<400> SEQUENCE: 13
gaaggcatcc agacccgaaa c 21

<210> SEQ ID NO 14
<211> LENGTH: 20
<212> TYPE: DNA
<213> ORGANISM: Artificial Sequence
<220> FEATURE:
<223> OTHER INFORMATION: Gata3

<400> SEQUENCE: 14
acccatggcg gtgaccatgc 20

<210> SEQ ID NO 15
<211> LENGTH: 20
<212> TYPE: DNA
<213> ORGANISM: Artificial Sequence
<220> FEATURE:
<223> OTHER INFORMATION: Il4

<400> SEQUENCE: 15
ggtctcaacc cccagctagt 20

<210> SEQ ID NO 16
<211> LENGTH: 23
<212> TYPE: DNA
<213> ORGANISM: Artificial Sequence
<220> FEATURE:
<223> OTHER INFORMATION: Il4

<400> SEQUENCE: 16
gccgatgatc tctctcaagt gat 23

<210> SEQ ID NO 17
<211> LENGTH: 21
<212> TYPE: DNA
<213> ORGANISM: Artificial Sequence
<220> FEATURE:
<223> OTHER INFORMATION: Il13

<400> SEQUENCE: 17
cagcctcccc gataccaaaa t 21

<210> SEQ ID NO 18
<211> LENGTH: 21

<212> TYPE: DNA
<213> ORGANISM: Artificial Sequence
<220> FEATURE:
<223> OTHER INFORMATION: Il13

<400> SEQUENCE: 18
gcgaaacagt tgctttgtgt a                                         21

<210> SEQ ID NO 19
<211> LENGTH: 23
<212> TYPE: DNA
<213> ORGANISM: Artificial Sequence
<220> FEATURE:
<223> OTHER INFORMATION: Il5

<400> SEQUENCE: 19
ctctgttgac aagcaatgag acg                                       23

<210> SEQ ID NO 20
<211> LENGTH: 22
<212> TYPE: DNA
<213> ORGANISM: Artificial Sequence
<220> FEATURE:
<223> OTHER INFORMATION: Il5

<400> SEQUENCE: 20
tcttcagtat gtctagcccc tg                                        22

<210> SEQ ID NO 21
<211> LENGTH: 21
<212> TYPE: DNA
<213> ORGANISM: Artificial Sequence
<220> FEATURE:
<223> OTHER INFORMATION: Il10

<400> SEQUENCE: 21
gctcttactg actggcatga g                                         21

<210> SEQ ID NO 22
<211> LENGTH: 19
<212> TYPE: DNA
<213> ORGANISM: Artificial Sequence
<220> FEATURE:
<223> OTHER INFORMATION: Il10

<400> SEQUENCE: 22
cgcagctcta ggagcatgt                                            19

<210> SEQ ID NO 23
<211> LENGTH: 20
<212> TYPE: DNA
<213> ORGANISM: Artificial Sequence
<220> FEATURE:
<223> OTHER INFORMATION: Junb

<400> SEQUENCE: 23
tcacgacgac tcttacgcag                                           20

<210> SEQ ID NO 24
<211> LENGTH: 20
<212> TYPE: DNA
<213> ORGANISM: Artificial Sequence
<220> FEATURE:
<223> OTHER INFORMATION: Junb

<400> SEQUENCE: 24
ccttgagacc ccgatagggα                                                  20

<210> SEQ ID NO 25
<211> LENGTH: 21
<212> TYPE: DNA
<213> ORGANISM: Artificial Sequence
<220> FEATURE:
<223> OTHER INFORMATION: Rorgt

<400> SEQUENCE: 25
gacccacacc tcacaaattg a                                                21

<210> SEQ ID NO 26
<211> LENGTH: 21
<212> TYPE: DNA
<213> ORGANISM: Artificial Sequence
<220> FEATURE:
<223> OTHER INFORMATION: Rorgt

<400> SEQUENCE: 26
agtaggccac attacactgc t                                                21

<210> SEQ ID NO 27
<211> LENGTH: 21
<212> TYPE: DNA
<213> ORGANISM: Artificial Sequence
<220> FEATURE:
<223> OTHER INFORMATION: Il17

<400> SEQUENCE: 27
tttaactccc ttggcgcaaa a                                                21

<210> SEQ ID NO 28
<211> LENGTH: 20
<212> TYPE: DNA
<213> ORGANISM: Artificial Sequence
<220> FEATURE:
<223> OTHER INFORMATION: Il17

<400> SEQUENCE: 28
ctttccctcc gcattgacac                                                  20

<210> SEQ ID NO 29
<211> LENGTH: 21
<212> TYPE: DNA
<213> ORGANISM: Artificial Sequence
<220> FEATURE:
<223> OTHER INFORMATION: Il21

<400> SEQUENCE: 29
ggacccttgt ctgtctggta g                                                21

<210> SEQ ID NO 30
<211> LENGTH: 23
<212> TYPE: DNA
<213> ORGANISM: Artificial Sequence
<220> FEATURE:
<223> OTHER INFORMATION: Il21

<400> SEQUENCE: 30
tgtggagctg atagaagttc agg                                              23

<210> SEQ ID NO 31
<211> LENGTH: 21
<212> TYPE: DNA
<213> ORGANISM: Artificial Sequence

```
<220> FEATURE:
<223> OTHER INFORMATION: Gmcsf

<400> SEQUENCE: 31
ggccttggaa gcatgtagag g                                              21

<210> SEQ ID NO 32
<211> LENGTH: 23
<212> TYPE: DNA
<213> ORGANISM: Artificial Sequence
<220> FEATURE:
<223> OTHER INFORMATION: Gmcsf

<400> SEQUENCE: 32
ggagaactcg ttagagacga ctt                                            23

<210> SEQ ID NO 33
<211> LENGTH: 19
<212> TYPE: DNA
<213> ORGANISM: Artificial Sequence
<220> FEATURE:
<223> OTHER INFORMATION: Batf

<400> SEQUENCE: 33
gttctgtttc tccaggtcc                                                 19

<210> SEQ ID NO 34
<211> LENGTH: 17
<212> TYPE: DNA
<213> ORGANISM: Artificial Sequence
<220> FEATURE:
<223> OTHER INFORMATION: Batf

<400> SEQUENCE: 34
gaagaatcgc atcgctg                                                   17

<210> SEQ ID NO 35
<211> LENGTH: 20
<212> TYPE: DNA
<213> ORGANISM: Artificial Sequence
<220> FEATURE:
<223> OTHER INFORMATION: Socs1

<400> SEQUENCE: 35
ctgcggcttc tattggggac                                                20

<210> SEQ ID NO 36
<211> LENGTH: 21
<212> TYPE: DNA
<213> ORGANISM: Artificial Sequence
<220> FEATURE:
<223> OTHER INFORMATION: Socs1

<400> SEQUENCE: 36
aaaaggcagt cgaaggtctc g                                              21

<210> SEQ ID NO 37
<211> LENGTH: 21
<212> TYPE: DNA
<213> ORGANISM: Artificial Sequence
<220> FEATURE:
<223> OTHER INFORMATION: Socs3

<400> SEQUENCE: 37
atggtcaccc acagcaagtt t                                              21
```

<210> SEQ ID NO 38
<211> LENGTH: 21
<212> TYPE: DNA
<213> ORGANISM: Artificial Sequence
<220> FEATURE:
<223> OTHER INFORMATION: Socs3

<400> SEQUENCE: 38
tccagtagaa tccgctctcc t                                              21

<210> SEQ ID NO 39
<211> LENGTH: 21
<212> TYPE: DNA
<213> ORGANISM: Artificial Sequence
<220> FEATURE:
<223> OTHER INFORMATION: Socs5

<400> SEQUENCE: 39
gagggaggaa gccgtaatga g                                              21

<210> SEQ ID NO 40
<211> LENGTH: 19
<212> TYPE: DNA
<213> ORGANISM: Artificial Sequence
<220> FEATURE:
<223> OTHER INFORMATION: Socs5

<400> SEQUENCE: 40
cggcacagtt ttggttccg                                                 19

<210> SEQ ID NO 41
<211> LENGTH: 20
<212> TYPE: DNA
<213> ORGANISM: Artificial Sequence
<220> FEATURE:
<223> OTHER INFORMATION: Perforin

<400> SEQUENCE: 41
gagaagacct atcaggacca                                                20

<210> SEQ ID NO 42
<211> LENGTH: 17
<212> TYPE: DNA
<213> ORGANISM: Artificial Sequence
<220> FEATURE:
<223> OTHER INFORMATION: Perforin

<400> SEQUENCE: 42
agcctgtggt aagcatg                                                   17

<210> SEQ ID NO 43
<211> LENGTH: 18
<212> TYPE: DNA
<213> ORGANISM: Artificial Sequence
<220> FEATURE:
<223> OTHER INFORMATION: Gzmb

<400> SEQUENCE: 43
cctcctgcta ctgctgac                                                  18

<210> SEQ ID NO 44
<211> LENGTH: 18
<212> TYPE: DNA
<213> ORGANISM: Artificial Sequence
<220> FEATURE:
<223> OTHER INFORMATION: Gzmb

```
<400> SEQUENCE: 44
gtcagcacaa agtcctct                                                  18

<210> SEQ ID NO 45
<211> LENGTH: 22
<212> TYPE: DNA
<213> ORGANISM: Artificial Sequence
<220> FEATURE:
<223> OTHER INFORMATION: Il13ra2

<400> SEQUENCE: 45
accgaaatgt tgatagcgac ag                                             22

<210> SEQ ID NO 46
<211> LENGTH: 22
<212> TYPE: DNA
<213> ORGANISM: Artificial Sequence
<220> FEATURE:
<223> OTHER INFORMATION: Il13ra2

<400> SEQUENCE: 46
acaatgctct gacaaatgcg ta                                             22

<210> SEQ ID NO 47
<211> LENGTH: 20
<212> TYPE: DNA
<213> ORGANISM: Artificial Sequence
<220> FEATURE:
<223> OTHER INFORMATION: Chit1

<400> SEQUENCE: 47
tgggcaggtg tgatgactct                                                20

<210> SEQ ID NO 48
<211> LENGTH: 21
<212> TYPE: DNA
<213> ORGANISM: Artificial Sequence
<220> FEATURE:
<223> OTHER INFORMATION: Chit1

<400> SEQUENCE: 48
ccctgggaaa gaaccgaact g                                              21

<210> SEQ ID NO 49
<211> LENGTH: 21
<212> TYPE: DNA
<213> ORGANISM: Artificial Sequence
<220> FEATURE:
<223> OTHER INFORMATION: Amcase

<400> SEQUENCE: 49
ctgcgtcagt atgggtttga t                                              21

<210> SEQ ID NO 50
<211> LENGTH: 21
<212> TYPE: DNA
<213> ORGANISM: Artificial Sequence
<220> FEATURE:
<223> OTHER INFORMATION: Amcase

<400> SEQUENCE: 50
tgggcctgtt gctctcaata g                                              21

<210> SEQ ID NO 51
```

```
<211> LENGTH: 21
<212> TYPE: DNA
<213> ORGANISM: Artificial Sequence
<220> FEATURE:
<223> OTHER INFORMATION: Ym-1

<400> SEQUENCE: 51
acctgccccg ttcagtgcca t                                          21

<210> SEQ ID NO 52
<211> LENGTH: 23
<212> TYPE: DNA
<213> ORGANISM: Artificial Sequence
<220> FEATURE:
<223> OTHER INFORMATION: Ym-1

<400> SEQUENCE: 52
ccttggaatg tctttctcca cag                                        23

<210> SEQ ID NO 53
<211> LENGTH: 19
<212> TYPE: DNA
<213> ORGANISM: Artificial Sequence
<220> FEATURE:
<223> OTHER INFORMATION: Foxp3

<400> SEQUENCE: 53
cccatcccca ggagtcttg                                             19

<210> SEQ ID NO 54
<211> LENGTH: 20
<212> TYPE: DNA
<213> ORGANISM: Artificial Sequence
<220> FEATURE:
<223> OTHER INFORMATION: Foxp3

<400> SEQUENCE: 54
accatgacta ggggcactgt                                            20

<210> SEQ ID NO 55
<211> LENGTH: 22
<212> TYPE: DNA
<213> ORGANISM: Artificial Sequence
<220> FEATURE:
<223> OTHER INFORMATION: Eomes

<400> SEQUENCE: 55
tcatcgctgt gacggcctac ca                                         22

<210> SEQ ID NO 56
<211> LENGTH: 22
<212> TYPE: DNA
<213> ORGANISM: Artificial Sequence
<220> FEATURE:
<223> OTHER INFORMATION: Eomes

<400> SEQUENCE: 56 gggaatccg tgggagatgg ag                                          22

<210> SEQ ID NO 57
<211> LENGTH: 22
<212> TYPE: DNA
<213> ORGANISM: Artificial Sequence
<220> FEATURE:
<223> OTHER INFORMATION: Tnfsf10

<400> SEQUENCE: 57
```

```
atggtgattt gcatagtgct cc                                              22
```

<210> SEQ ID NO 58
<211> LENGTH: 21
<212> TYPE: DNA
<213> ORGANISM: Artificial Sequence
<220> FEATURE:
<223> OTHER INFORMATION: Tnfsf10

<400> SEQUENCE: 58

```
gcaagcaggg tctgttcaag a                                               21
```

<210> SEQ ID NO 59
<211> LENGTH: 20
<212> TYPE: DNA
<213> ORGANISM: Artificial Sequence
<220> FEATURE:
<223> OTHER INFORMATION: Ccr5

<400> SEQUENCE: 59

```
ttttcaaggg tcagttccga                                                 20
```

<210> SEQ ID NO 60
<211> LENGTH: 22
<212> TYPE: DNA
<213> ORGANISM: Artificial Sequence
<220> FEATURE:
<223> OTHER INFORMATION: Ccr5

<400> SEQUENCE: 60

```
ggaagaccat catgttaccc ac                                              22
```

<210> SEQ ID NO 61
<211> LENGTH: 23
<212> TYPE: DNA
<213> ORGANISM: Artificial Sequence
<220> FEATURE:
<223> OTHER INFORMATION: Cxcr3

<400> SEQUENCE: 61

```
taccttgagg ttagtgaacg tca                                             23
```

<210> SEQ ID NO 62
<211> LENGTH: 21
<212> TYPE: DNA
<213> ORGANISM: Artificial Sequence
<220> FEATURE:
<223> OTHER INFORMATION: Cxcr3

<400> SEQUENCE: 62

```
cgctctcgtt ttccccataa t                                               21
```

<210> SEQ ID NO 63
<211> LENGTH: 21
<212> TYPE: DNA
<213> ORGANISM: Artificial Sequence
<220> FEATURE:
<223> OTHER INFORMATION: Cxcr2

<400> SEQUENCE: 63

```
atgccctcta ttctgccaga t                                               21
```

<210> SEQ ID NO 64
<211> LENGTH: 23
<212> TYPE: DNA

```
<213> ORGANISM: Artificial Sequence
<220> FEATURE:
<223> OTHER INFORMATION: Cxcr2

<400> SEQUENCE: 64
gtgctccggt tgtataagat gac                                              23

<210> SEQ ID NO 65
<211> LENGTH: 21
<212> TYPE: DNA
<213> ORGANISM: Artificial Sequence
<220> FEATURE:
<223> OTHER INFORMATION: Ctse

<400> SEQUENCE: 65
gacatcagtc ccttcggaag a                                                21

<210> SEQ ID NO 66
<211> LENGTH: 23
<212> TYPE: DNA
<213> ORGANISM: Artificial Sequence
<220> FEATURE:
<223> OTHER INFORMATION: Ctse

<400> SEQUENCE: 66
aggggttcat tgacactcga ata                                              23

<210> SEQ ID NO 67
<211> LENGTH: 21
<212> TYPE: DNA
<213> ORGANISM: Artificial Sequence
<220> FEATURE:
<223> OTHER INFORMATION: Twist1

<400> SEQUENCE: 67
ggacaagctg agcaagattc a                                                21

<210> SEQ ID NO 68
<211> LENGTH: 19
<212> TYPE: DNA
<213> ORGANISM: Artificial Sequence
<220> FEATURE:
<223> OTHER INFORMATION: Twist1

<400> SEQUENCE: 68
cggagaaggc gtagctgag                                                   19
```